United States Patent
Chen et al.

(10) Patent No.: US 10,752,595 B2
(45) Date of Patent: Aug. 25, 2020

(54) CRYSTALLINE FORMS OF A BROMODOMAIN AND EXTRATERMINAL PROTEIN INHIBITOR DRUG, PROCESSES FOR PREPARATION THEREOF, AND USE THEREOF

(71) Applicant: Crystal Pharmaceutical (Suzhou) Co., Ltd., Suzhou, Jiangsu (CN)

(72) Inventors: Minhua Chen, Suzhou (CN); Yanfeng Zhang, Suzhou (CN); Xiaoting Zhai, Suzhou (CN); Kaiqiang Yan, Suzhou (CN); Xiaoyu Zhang, Suzhou (CN)

(73) Assignee: CRYSTAL PHARMACEUTICAL (SUZHOU) CO., LTD., Suzhou, Jiangsu (CN)

( * ) Notice: Subject to any disclaimer, the term of this patent is extended or adjusted under 35 U.S.C. 154(b) by 0 days.

(21) Appl. No.: 16/467,774

(22) PCT Filed: Dec. 8, 2017

(86) PCT No.: PCT/CN2017/115143
§ 371 (c)(1),
(2) Date: Jun. 7, 2019

(87) PCT Pub. No.: WO2018/103726
PCT Pub. Date: Jun. 14, 2018

(65) Prior Publication Data
US 2019/0330161 A1    Oct. 31, 2019

(30) Foreign Application Priority Data

Dec. 9, 2016 (CN) .......................... 2016 1 1131698
Dec. 27, 2016 (CN) .......................... 2016 1 1229263

(51) Int. Cl.
*C07D 239/91* (2006.01)
*C07D 413/06* (2006.01)
*C07D 471/04* (2006.01)
*A61K 31/517* (2006.01)

(52) U.S. Cl.
CPC .......... *C07D 239/91* (2013.01); *A61K 31/517* (2013.01); *C07D 413/06* (2013.01); *C07D 471/04* (2013.01); *C07B 2200/13* (2013.01)

(58) Field of Classification Search
CPC .. C07D 239/91; C07D 413/06; C07D 471/04; A61K 31/517
See application file for complete search history.

(56) References Cited

U.S. PATENT DOCUMENTS 8,053,440 B2 * 11/2011 Hansen ................ A61K 31/695
514/266.1
8,114,995 B2 * 2/2012 Hansen ................ C07D 239/91
544/289
2018/0104245 A1    4/2018 Hansen

FOREIGN PATENT DOCUMENTS

CN    101641339 A    2/2010
CN    101970416 A    2/2011
EP    2346837 A1     7/2011

OTHER PUBLICATIONS

McLure et al., RVX-208, an Inducer of ApoA-I in Humans, Is a BET Bromodomain Antagonist, PLOS One, vol. 8, Issue 12, pp. 1-12, 2013.*
Picaud et al., RVX-208, an inhibitor of BET transcriptional regulators with selectivity for the second bromodomain. Proc Natl Acad Sci U S A. Dec. 3, 2013;110(49):19754-9.
International Search Report and Written Opinion for Application No. PCT/CN2017/115143, dated Feb. 24, 2018, 14 pages.

* cited by examiner

*Primary Examiner* — Deepak R Rao
(74) *Attorney, Agent, or Firm* — McCarter & English LLP; Steven G. Davis; Wei Song

(57) ABSTRACT

The present disclosure relates to novel crystalline forms of a bromodomain protein inhibitor 2-[4-(2-hydroxyethoxy)-3,5-dimethylphenyl]-5,7-dimethoxyquinazolin-4(3H)-one and processes for preparation and use thereof, relating to pharmaceutical industry. Form CS2, Form CS8, Form CS13, Form CS20, Form CS1, Form CS7, Form CS9, Form CS11 and Form CS4 of the present disclosure can be used for preparing drugs treating cardiovascular, cholesterol or lipid-related disorders.

22 Claims, 27 Drawing Sheets

(I)

CRYSTALLINE FORMS OF A BROMODOMAIN AND EXTRATERMINAL PROTEIN INHIBITOR DRUG, PROCESSES FOR PREPARATION THEREOF, AND USE THEREOF

CROSS-REFERENCE TO RELATED APPLICATIONS

This application is a U.S. national stage application, filed under 35 U.S.C. § 371(c), of PCT International Application No. PCT/CN2017/115143 filed on Dec. 8, 2017, which claims the benefit of foreign priority of Chinese patent application No. 201611131698.6 filed on Dec. 9, 2016 and Chinese patent application No. 201611229263.5 filed on Dec. 27, 2016. The entire contents of the aforementioned applications are incorporated herein by reference.

TECHNICAL FIELD

The present disclosure relates to the field of pharmaceutical chemistry, particularly relates to novel crystalline forms of 2-[4-(2-hydroxyethoxy)-3,5-dimethylphenyl]-5,7-dimethoxyquinazolin-4(3H)-one, processes for preparation and use thereof.

BACKGROUND

2-[4-(2-hydroxyethoxy)-3,5-dimethylphenyl]-5,7-dimethoxyquinazolin-4(3H)-one, also known as apabetalone, is a bromodomain and extraterminal (BET) protein inhibitor developed by Resverlogix in Canada. Apabetalone can be used in the treatment of cardiovascular, cholesterol or lipid-related disorders. Especially in the treatment of atherosclerosis, acute coronary syndrome and predecessor diabetes, apabetalone has shown significant curative effect. The structure of apabetalone is shown as follows:

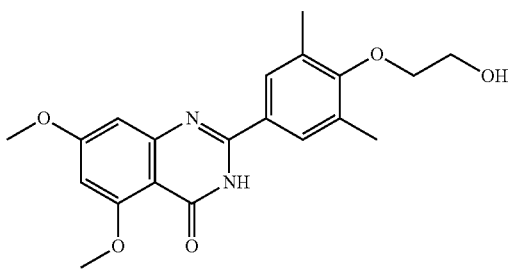 [SMILES: COc1cc(OC)c2c(=O)[nH]c(-c3cc(C)c(OCCO)c(C)c3)nc2c1]

Cardiovascular diseases, also known as circulatory system diseases, can be subdivided into acute diseases and chronic diseases and generally relate to atherosclerosis. Cardiovascular disease is one of the most serious diseases threatening human life worldwide. Its morbidity and mortality rate have surpassed that of tumour diseases and ranked first. In China, there are about 290 million patients suffering from cardiovascular diseases, and the number of patients is increasing year by year. However, people's need for drugs of cardiovascular diseases have not been fulfilled, and new drugs still need to be developed continuously. Studies have shown that apabetalone can inhibit BRD4 of BET family, thereby regulating the expression of apolipoprotein A-1 (ApoA-1) and the synthesis of high density lipoprotein cholesterol, and realizing the treatment of cardiovascular related diseases. No patent or literature about apabetalone crystalline forms is found after searching patents and literatures published locally and abroad.

Different crystalline forms of solid chemical drugs have different solubility and stability, and can affect drug's in vivo dissolution and absorption, which will further affect drug's clinical efficacy. The inventors of the present disclosure surprisingly discovered crystalline form CS2, form CS8, form CS13, form CS20, form CS1, form CS7, form CS9, form CS11 and form CS4 after conducting a large number of experiments, which provides a new and better choice for the preparation of pharmaceutical preparations containing apabetalone and is of great significance for drug development.

SUMMARY

Form CS2, Form CS8, Form CS13, Form CS20, Form CS1, Form CS7, Form CS9, Form CS11 and Form CS4 were discovered by the inventors of the present disclosure after a lot of experiments and research. The above polymorphs have good stability. The polymorphs are stable for at least two weeks under the conditions of 25° C./60% RH and/or 40° C./75% RH, preferably at least 6 weeks, and more preferably at least 10 months. The novel polymorphs discovered by the inventors of the present disclosure have advantages in simple and repeatable preparation method, high purity, good solubility and low hygroscopicity, which makes the polymorphs meet the requirements of medical use and is suitable for production and application.

The main objective of the present disclosure is to provide novel crystalline forms of apabetalone, processes for preparation and use thereof.

According to the objective of the present disclosure, crystalline form CS2 is provided (hereinafter referred to as "Form C52"). Said Form CS2 is a hydrate.

The X-ray powder diffraction pattern of Form CS2 shows characteristic peaks at 2theta values of 11.5°±0.2°, 6.6°±0.2° and 8.8°±0.2° using CuKα radiation.

Furthermore, the X-ray powder diffraction pattern of Form CS2 shows one or two characteristic peaks at 2theta values of 5.1°±0.2° and 15.3°±0.2°. Preferably, the X-ray powder diffraction pattern of Form CS2 shows characteristic peaks at 2theta values of 5.1°±0.2° and 15.3°±0.2°.

In a preferred embodiment, the X-ray powder diffraction pattern of Form CS2 shows characteristic peaks at 2theta values of 11.5°±0.2°, 6.6°±0.2°, 8.8°±0.2°, 5.1°±0.2°, 15.3°±0.2°, 13.3°±0.2°, 20.2°±0.2°, 23.1°±0.2° and 25.3°±0.2° using CuKα radiation.

Without any limitation being implied, in a specific embodiment, the X-ray powder diffraction pattern of Form CS2 is substantially as depicted in FIG. 1A.

According to the objective of the present disclosure, a process for preparing Form CS2 of apabetalone is also provided. The process comprises: Adding apabetalone solid into alcohols, a mixture of alcohols and ethers, a mixture of alcohols and ketones or a mixture of alcohols and arenes. Heating to dissolve the solid, filtering and cooling the solution to obtain a solid. The obtained solid is Form CS2 of apabetalone.

Furthermore, said alcohol includes methanol; said ether includes 2-methyltetrahydrofuran; said arene includes toluene; said ketone includes methyl isobutyl ketone; said heating temperature is 50-100° C.; said cooling temperature is −20-5° C.

Form CS2 of the present disclosure has following advantages:

1) At present, there is no patent or literature about crystalline forms of apabetalone. The inventor of the present disclosure has solved this difficult problem after a lot of experimental research and found Form CS2, which is suitable for drug development.

2) Form CS2 of the present disclosure has good solubility in SGF (simulated gastric fluids) and FeSSIF (fed state simulated intestinal fluids). Especially in SGF, the solubility of the Form CS2 is as high as 0.61 mg/mL at 24 hours. Higher solubility is beneficial to improve drug's blood concentration and bioavailability, which is of great significance for drug research.

According to the objective of the present disclosure, crystalline form CS8 of apabetalone is provided (hereinafter referred to as Form CS8). Said Form CS8 is an anhydrate.

The X-ray powder diffraction pattern of Form CS8 shows characteristic peaks at 2theta values of 13.5°±0.2°, 7.8°±0.2°, 22.5°±0.2° and 11.4°±0.2° using CuKα radiation.

Furthermore, the X-ray powder diffraction pattern of Form CS8 shows one or two characteristic peaks at 2theta values of 25.9°±0.2° and 13.1°±0.2°. Preferably, the X-ray powder diffraction pattern of Form CS8 shows characteristic peaks at 2theta values of 25.9°±0.2° and 13.1°±0.2°.

Furthermore, the X-ray powder diffraction pattern of Form CS8 shows one or two characteristic peaks at 2theta values of 28.1°±0.2° and 20.2°±0.2°. Preferably, the X-ray powder diffraction pattern of Form CS8 shows characteristic peaks at 2theta values of 28.1°±0.2° and 20.2°±0.2°.

In a preferred embodiment, the X-ray powder diffraction pattern of Form CS8 shows characteristic peaks at 2theta values of 23.9°±0.2°, 13.5°±0.2°, 7.8°±0.2°, 22.5°±0.2°, 11.4°±0.2°, 25.9°±0.2°, 13.1°±0.2°, 28.1°±0.2°, 20.2°±0.2° and 9.7°±0.2° using CuKα radiation.

Without any limitation being implied, in a specific embodiment the X-ray powder diffraction pattern of Form CS8 is substantially as depicted in FIG. 2A.

According to the objective of the present disclosure, a process for preparing Form CS8 of apabetalone is also provided. The process comprises: Adding apabetalone solid into a single solvent of halohydrocarbons or a mixture of solvents of halohydrocarbons and alcohols. Heating to dissolve the solid, filtering and cooling the solution to obtain a solid. The obtained solid is Form CS8 of apabetalone.

Furthermore, said halohydrocarbon includes dichloromethane; said alcohol includes isopropanol; said volume ratio of halohydrocarbon and isopropanol is preferably 4:1; said heating temperature is 40-60° C., preferably 50° C.; said cooling temperature is −20-5° C.

Form CS8 of the present disclosure has following advantages:

1) At present, there is no patent or literature about crystalline forms of apabetalone. The inventor of the present disclosure has solved this difficult problem after a lot of experimental research and found Form CS8, which is suitable for drug development.

2) Form CS8 of the present disclosure has good long-term stability. Form CS8 is stable for at least 2 weeks when stored under the condition of 25° C./60% RH, which is conducive to long-term storage. Form CS8 has excellent stability, which can ensure the quality of the drug will not be affected aspolymorphic transition will not occur in the process of preparation, transportation and storage. It is of great significance to ensure the efficacy and safety of the drug and prevent the occurrence of adverse drug reactions.

3) Form CS8 of the present disclosure has low hygroscopicity. The weight gain of Form CS8 of the present disclosure at 80% RH is 0.34%. Form CS8 is slightly hygroscopic. Due to the low hygroscopicity, it is not necessary to control the environmental humidity in preparation processes, and no strict requirement is needed for packaging and storage, which is beneficial to long-term storage and industrial production of drugs and reduces the cost. Due to the unstrict requirement on the storage conditions, the cost of storage and quality control will be greatly reduced, which has strong economic value and is more suitable for medicinal use. According to the objective of the present disclosure, crystalline form CS13 is provided (hereinafter referred to as "Form CS13"). Said Form CS13 is a hydrate.

The X-ray powder diffraction pattern of Form CS13 shows characteristic peaks at 2theta values of 5.1°±0.2°, 12.5°±0.2° and 17.1°±0.2° using CuKα radiation.

Furthermore, the X-ray powder diffraction pattern of Form CS13 shows one or two or three characteristic peaks at 2theta values of 6.4°±0.2°, 8.5°±0.2° and 25.7°±0.2°. Preferably, the X-ray powder diffraction pattern of Form CS13 shows characteristic peaks at 2theta values of 6.4°±0.2°, 8.5°±0.2° and 25.7°±0.2°.

Furthermore, the X-ray powder diffraction pattern of Form CS13 shows one or two characteristic peaks at 2theta values of 7.8°±0.2° and 16.0°±0.2°. Preferably, the X-ray powder diffraction pattern of Form CS13 shows characteristic peaks at 2theta values of 7.8°±0.2° and 16.0°±0.2°.

In a preferred embodiment, the X-ray powder diffraction pattern of Form CS13 shows characteristic peaks at 2theta values of 5.1°±0.2°, 12.5°±0.2°, 17.1°±0.2°, 6.4°±0.2°, 8.5°±0.2°, 25.7°±0.2°, 7.8°±0.2° and 16.0°±0.2° using CuKα radiation.

Without any limitation being implied, in a specific embodiment the X-ray powder diffraction pattern of Form CS13 is substantially as depicted in FIG. 3A.

According to the objective of the present disclosure, a process for preparing Form CS13 of apabetalone is also provided. The process comprises: Dissolving apabetalone solid in a mixture of ethers and water or a mixture of ketones and water. Filtering the solution and then evaporating the filtrate at room temperature to obtain a solid. The obtained solid is Form CS13 of apabetalone.

Furthermore, said ether includes tetrahydrofuran; said ketone includes acetone; said volume ratio of ether and water is preferably 4:1; said volume ratio of ketone and water is preferably 9:1.

Form CS13 of the present disclosure has following advantages:

1) At present, there is no patent or literature about crystalline forms of apabetalone. The inventor of the present disclosure has solved this difficult problem after a lot of experimental research and found Form CS13, which is suitable for drug development.

2) Form CS13 of the present disclosure has good solubility in SGF and FeSSIF. Highly soluble crystalline forms are conducive to improving drug's plasma concentration and bioavailability.

According to the objective of the present disclosure, crystalline form CS20 of apabetalone is provided (hereinafter referred to as Form CS20). Said Form CS20 is an acetic acid solvate.

The X-ray powder diffraction pattern of Form CS20 shows characteristic peaks at 2theta values of 8.4°±0.2°, 18.9°±0.2° and 13.5°±0.2° using CuKα radiation.

Furthermore, the X-ray powder diffraction pattern of Form CS20 shows one or two or three characteristic peaks at 2theta values of 11.3°±0.2°, 9.4°±0.2° and 5.6°±0.2°. Preferably, the X-ray powder diffraction pattern of Form CS20 shows characteristic peaks at 2theta values of 11.3°±0.2°, 9.4°±0.2° and 5.6°±0.2°.

Furthermore, the X-ray powder diffraction pattern of Form CS20 shows one or more characteristic peaks at 2theta values of 26.3°±0.2°, 20.1°±0.2°, 20.6°±0.2° and 24.4°±0.2°. Preferably, the X-ray powder diffraction pattern of Form CS20 shows characteristic peaks at 2theta values of 26.3°±0.2°, 20.1°±0.2°, 20.6°±0.2° and 24.4°±0.2°.

Furthermore, the X-ray powder diffraction pattern of Form CS20 shows one or two or three characteristic peaks at 2theta values of 14.5°±0.2°, 16.9°±0.2° and 22.8°±0.2°. Preferably, the X-ray powder diffraction pattern of Form CS20 shows characteristic peaks at 2theta values of 14.5°±0.2°, 16.9°±0.2° and 22.8°±0.2°.

In a preferred embodiment, the X-ray powder diffraction pattern of Form CS20 shows characteristic peaks at 2theta values of 8.4°±0.2°, 18.9°±0.2°, 13.5°±0.2°, 11.3°±0.2°, 9.4°±0.2°, 5.6°±0.2°, 26.3°±0.2°, 20.1°±0.2°, 20.6°±0.2°, 24.4°±0.2°, 14.5°±0.2°, 16.9°±0.2° and 22.8°±0.2° using CuKα radiation.

Without any limitation being implied, in a specific embodiment the X-ray powder diffraction pattern of Form CS20 is substantially as depicted in FIG. 4A.

According to the objective of the present disclosure, a process for preparing Form CS20 of apabetalone is also provided. The process comprises: Dissolving apabetalone solid in a mixture of acetic acid and nitriles or a mixture of acetic acid and esters. Filtering the solution and then evaporating the filtrate at room temperature to obtain a solid. The obtained solid is Form CS20 of apabetalone.

Furthermore, said nitrile includes acetonitrile; said ester includes ethyl acetate; said volume ratio of nitrile and acetic acid is 9:1; said volume ratio of ester and acetic acid is 4:1.

Form CS20 of the present disclosure has following advantages:

1) At present, there is no patent or literature about crystalline forms of apabetalone. The inventor of the present disclosure has solved this difficult problem after a lot of experimental research and found Form CS20, which is suitable for drug development.

2) Form CS20 has good long-term stability. Form CS20 is stable for at least 2 weeks when stored under the conditions of 25° C./60% RH and 40° C./75% RH. Form CS20 has excellent stability, which can ensure that the quality of the drug will be affected as polymorphic transition will not occur in the process of preparation, transportation and storage. It is of great significance to ensure the efficacy and safety of the drug and prevent the occurrence of adverse drug reactions.

3) Form CS20 of the present disclosure has good solubility in SGF and FeSSIF. Highly soluble crystalline forms are conducive to improving drug's blood concentration and bioavailability.

According to the objective of the present disclosure, crystalline form CS1 of apabetalone is provided (hereinafter referred to as Form CS1). Said Form CS1 is an anhydrate.

The X-ray powder diffraction pattern of Form CS1 shows characteristic peaks at 2theta values of 6.1°±0.2°, 12.3°±0.2°, 26.1°±0.2° and 26.8°±0.2° using CuKα radiation.

Furthermore, the X-ray powder diffraction pattern of Form CS1 shows one or two or three characteristic peaks at 2theta values of 16.4°±0.2°, 18.5°±0.2° and 23.2°±0.2°. Preferably, the X-ray powder diffraction pattern of Form CS1 shows characteristic peaks at 2theta values of 16.4°±0.2°, 18.5°±0.2° and 23.2°±0.2°.

Furthermore, the X-ray powder diffraction pattern of Form CS1 shows one or more characteristic peaks at 2theta values of 13.0°±0.2°, 14.1°±0.2°, 17.1°±0.2° and 24.5°±0.2°. Preferably, the X-ray powder diffraction pattern of Form CS1 shows characteristic peaks at 2theta values of 13.0°±0.2°, 14.1°±0.2°, 17.1°±0.2° and 24.5°±0.2°.

In a preferred embodiment, the X-ray powder diffraction pattern of Form CS1 shows characteristic peaks at 2theta values of 6.1°±0.2°, 12.3°±0.2°, 26.1°±0.2°, 26.8°±0.2°, 16.4°±0.2°, 18.5°±0.2°, 23.2°±0.2°, 13.0°±0.2°, 14.1°±0.2°, 17.1°±0.2°, 24.5°±0.2° and 20.5°±0.2° using CuKα radiation.

Without any limitation being implied, in a specific embodiment the X-ray powder diffraction pattern of Form CS1 is substantially as depicted in FIG. 5A.

According to the objective of the present disclosure, a process for preparing Form CS1 of apabetalone is also provided. The process comprises:

Method 1: Dissolving step: Dissolving apabetalone solid in a solvent to obtain a clear solution.

Precipitation step: Adding the prepared solution to an anti-solvent or adding an anti-solvent to the prepared solution to obtain a solid. The obtained solid is Form CS1 of apabetalone.

Furthermore, said solvent is a single solvent or a mixture of solvents selected from the group consisting of tetrahydrofuran, chloroform, dimethyl sulfoxide and dimethyl acetamide; said anti-solvent is a single solvent or a mixture of solvents selected from the group consisting of n-heptane, methyl tert-butyl ether, toluene, water and acetonitrile.

Method 2: Dissolving step: Dissolving apabetalone solid in solvent at 40-60° C. to obtain a clear solution.

Precipitation step: Cooling the prepared solution to −20-5° C. to obtain a solid. The obtained solid is Form CS1 of apabetalone.

Furthermore, said solvent is tetrahydrofuran, acetone, a mixture of tetrahydrofuran and methyl tert-butyl ether, a mixture of ethyl acetate and acetone, a mixture of acetonitrile and N, N-dimethyl formamide.

Preferably, said volume ratio of tetrahydrofuran and methyl tert-butyl ether is 2:1; said volume ratio of ethyl acetate and acetone is 1:1; said volume ratio of acetonitrile and N, N-dimethyl formamide is 9:1.

Form CS1 of the present disclosure has following advantages:

1) At present, there is no patent or literature about apabetalone's crystalline forms. The inventor of the present disclosure has solved his difficult problem after a lot of experimental research and found Form CS1, which is suitable for drug development.

2) Form CS1 has good long-term stability and mechanical stability. Form CS1 is stable for at least 10 months when stored under the conditions of 25° C./60% RH and 40° C./75% RH. The stability of crystalline form is very important for drug development. Form CS1 has excellent stability, which can ensure that the quality of the drug will not be affected as the polymorphic transition will not occur in the process of preparation, transportation and storage. It is of great significance to ensure the efficacy and safety of the drug and prevent the occurrence of adverse drug reactions. In addition, Form CS1 doesn't change after manual grinding, which indicates that Form CS1 has good mechanical stability. The grinding of APIs is usually needed in production process. Good grinding stability can reduce the risk of crystallinity change and polymorphic transition of APIs during production process.

3) Form CS1 of the present disclosure is almost non hygroscopic. The weight gain of Form CS1 of the present disclosure at 80% RH is 0.13% and the crystalline form doesn't change after DVS test. For almost non-hygroscopic crystalline form, it is not necessary to control the environmental humidity in production process. There is no special strict requirements for packaging and storage conditions, which saves costs and is suitable for industrial production and long-term storage of drugs. Due to the unstrict requirement on the storage conditions, the cost of material storage and quality control will be greatly reduced, which has strong economic value and is more suitable for medicinal use.

4) Form CS1 of the present disclosure has a good dissolution rate. In drug development, Form CS1 with fast dissolution rate can accelerate drug's in vivo dissolution. By adjusting the excipients, it is possible to control the rapid action of drugs in specific parts and get a short onset of action of the drugs.

According to the objective of the present disclosure, crystalline form CS7 of apabetalone is provided (hereinafter referred to as Form CS7). Said Form CS7 is an anhydrate.

The X-ray powder diffraction pattern of Form CS7 shows characteristic peaks at 2theta values of 5.9°±0.2°, 6.7°±0.2°, 10.7°±0.2° and 12.5°±0.2° using CuKα radiation.

Furthermore, the X-ray powder diffraction pattern of Form CS7 shows one or two or three characteristic peaks at 2theta values of 8.4°±0.2°, 16.9°±0.2 and 13.3°±0.2°. Preferably, the X-ray powder diffraction pattern of Form CS7 shows characteristic peaks at 2theta values of 8.4°±0.2°, 16.9°±0.2 and 13.3°±0.2°.

Furthermore, the X-ray powder diffraction pattern of Form CS7 shows one or more characteristic peaks at 2theta values of 16.0°±0.2°, 25.1°±0.2°, 15.0°±0.2° and 21.8°±0.2°. Preferably, the X-ray powder diffraction pattern of Form CS7 shows characteristic peaks at 2theta values of 16.0°±0.2°, 25.1°±0.2°, 15.0°±0.2° and 21.8°±0.2°.

In a preferred embodiment, the X-ray powder diffraction pattern of Form CS7 shows characteristic peaks at 2theta values of 5.9°±0.2°, 6.7°±0.2°, 10.7°±0.2°, 12.5°±0.2°, 8.4°±0.2°, 16.9°±0.2, 13.3°±0.2°, 16.0°±0.2°, 25.1°±0.2°, 15.0°±0.2°, 21.8°±0.2° and 24.5°±0.2° using CuKα radiation.

Without any limitation being implied, in a specific embodiment the X-ray powder diffraction pattern of Form CS7 is substantially as depicted in FIG. 6A.

According to the objective of the present disclosure, a process for preparing Form CS7 of apabetalone is also provided. The process comprises:

Dissolving step: Dissolving apabetalone solid in a solvent of halohydrocarbons to obtain a clear solution.

Precipitation step: The solid is induced by liquid vapor diffusion. The obtained solid is Form CS7 of apabetalone.

Said precipitation step comprises: Storing the prepared solution in an open glass vial. And then putting the vial into another vial containing a solvent of ketones to obtain a solid. The obtained solid is Form CS7 of apabetalone.

Preferably, said halohydrocarbon includes chloroform, and said ketone includes methyl isobutyl ketone.

Form CS7 of the present disclosure has the following advantages:

1) At present, there is no patent or literature about apabetalone's crystalline forms. The inventor of the present disclosure has solved this difficult problem after a lot of experimental research and found Form CS7, which is suitable for drug development.

2) Form CS7 has good stability. Form CS7 is stable for at least 4 weeks when stored under the conditions of 25° C./60% RH and 40° C./75% RH. The stability of crystalline form is very important for drug development. Form CS7 has excellent stability, which can ensure that the quality of the drug will not be affected as polymorphic transition will not occur in the process of preparation, transportation and storage. It is of great significance to ensure the efficacy and safety of the drug and prevent the occurrence of adverse drug reactions.

According to the objective of the present disclosure, crystalline form CS9 of apabetalone is provided (hereinafter referred to as Form CS9). Said Form CS9 is an anhydrate.

The X-ray powder diffraction pattern of Form CS9 shows characteristic peaks at 2theta values of 7.3°±0.2°, 9.9°±0.2° and 17.0°±0.2° using CuKα radiation.

Furthermore, the X-ray powder diffraction pattern of Form CS9 shows one or two or three characteristic peaks at 2theta values of 13.4°±0.2°, 3.9°±0.2° and 12.8°±0.2°. Preferably, the X-ray powder diffraction pattern of Form CS9 shows characteristic peaks at 2theta values of 13.4°±0.2°, 3.9°±0.2° and 12.8°±0.2°.

Furthermore, the X-ray powder diffraction pattern of Form CS9 shows one or more characteristic peaks at 2theta values of 12.1°±0.2°, 24.9°±0.2°, 22.5°±0.2° and 24.2°±0.2°. Preferably, the X-ray powder diffraction pattern of Form CS9 shows characteristic peaks at 2theta values of 12.1°±0.2°, 24.9°±0.2°, 22.5°±0.2° and 24.2°±0.2°.

In a preferred embodiment, the X-ray powder diffraction pattern of Form CS9 shows characteristic peaks at 2theta values of 7.3°±0.2°, 9.9°±0.2°, 17.0°±0.2°, 13.4°±0.2°, 3.9°±0.2°, 12.8°±0.2°, 12.1°±0.2°, 24.9°±0.2°, 22.5°±0.2°, 24.2°±0.2° and 6.0°±0.2° using CuKα radiation.

Without any limitation being implied, in a specific embodiment the X-ray powder diffraction pattern of Form CS9 is substantially as depicted in FIG. 7A.

According to the objective of the present disclosure, a process for preparing Form CS9 of apabetalone is also provided. The process comprises:

Dissolving step: Dissolving apabetalone solid in a mixture of ethers and alcohols or a mixture of halohydrocarbons and alcohols to obtain a clear solution.

Precipitation step: Evaporating the prepared solution at room temperature to obtain a solid. The obtained solid is Form CS9 of apabetalone.

Furthermore, said ether includes tetrahydrofuran, said alcohol includes isopropanol; said halohydrocarbons include dichloromethane and chloroform. Said volume ratio of ether and alcohol is 1:1; said volume ratio of halohydrocarbon and alcohol is 4:1.

Form CS9 of the present disclosure has the following advantages:

1) At present, there is no patent or literature about apabetalone's crystalline forms. The inventor of the present disclosure has solved this difficult problem after a lot of experimental research and found Form CS9, which is suitable for drug development.

2) Form CS9 has good stability. Form CS9 is stable for at least 10 months when stored under the condition of 25° C./60% RH and 40° C./75% RH. The stability of crystalline form is very important for drug development. Form CS9 has excellent stability, which can ensure that the quality of the drug will not be affected as polymorphic transition will not occur in the process of preparation, transportation and storage. It is of great significance to ensure the efficacy and safety of the drug and prevent the occurrence of adverse drug reactions.

3) Form CS9 of the present disclosure is almost non hygroscopic. The weight gain of Form CS9 of the present disclosure at 80% RH is 0.18% and the crystalline form doesn't change after DVS test. For almost non hygroscopic crystalline forms, it is not necessary to control the environmental humidity in production process. There is no special strict requirements for packaging and storage conditions. It saves costs and is easy to industrialize production and long-term storage of drugs. Because the storage conditions are not demanding, the cost of material storage and quality control will be greatly reduced, which has strong economic value and is more suitable for medicinal use.

According to the objective of the present disclosure, crystalline form CS11 of apabetalone is provided (hereinafter referred to as Form CS11). Said Form CS11 is a hydrate.

The X-ray powder diffraction pattern of Form CS11 shows characteristic peaks at 2theta values of 7.8°±0.2°, 8.8°±0.2°, 9.7°±0.2° and 13.6°±0.2° using CuKα radiation.

Furthermore, the X-ray powder diffraction pattern of Form CS11 shows one or two or three characteristic peaks at 2theta values of 4.4°±0.2°, 16.9°±0.2° and 21.6°±0.2°. Preferably, the X-ray powder diffraction pattern of Form CS11 shows characteristic peaks at 2theta values of 4.4°±0.2°, 16.9°±0.2° and 21.6°±0.2°.

Furthermore, the X-ray powder diffraction pattern of Form CS11 shows one or two characteristic peaks at 2theta values of 13.0°±0.2° and 15.3°±0.2°. Preferably, the X-ray powder diffraction pattern of Form CS11 shows characteristic peaks at 2theta values of 13.0°±0.2° and 15.3°±0.2°.

In a preferred embodiment, the X-ray powder diffraction pattern of Form CS11 shows characteristic peaks at 2theta values of 7.8°±0.2°, 8.8°±0.2°, 9.7°±0.2°, 13.6°±0.2°, 4.4°±0.2°, 16.9°±0.2°, 21.6°±0.2°, 13.0°±0.2°, 15.3°±0.2°, 22.7°±0.2°, 7.6°±0.2° and 17.6°±0.2° using CuKα radiation.

Without any limitation being implied, in a specific embodiment the X-ray powder diffraction pattern of Form CS11 is substantially as depicted in FIG. 8A.

According to the objective of the present disclosure, a process for preparing Form CS11 of apabetalone is also provided. The process comprises:

Method 1: Dissolving step: Dissolving apabetalone solid in a solvent of alcohols to obtain a clear solution.

Precipitation step: Adding the prepared solution to water or adding water to the prepared solution to obtain a solid. The obtained solid is Form CS11 of apabetalone.

Method 2: Dissolving step: Dissolving apabetalone solid in a solvent of halohydrocarbons or a mixture of alcohols and ketones or a mixture of alcohols and arenes to obtain a clear solution.

Precipitation step: Evaporating the prepared solution at room temperature to obtain a solid. The obtained solid is Form CS11 of apabetalone.

Furthermore, said alcohol of method 1 includes methanol, said alcohol of method 2 includes methanol; said ketones include acetone and methyl isobutyl ketone. Said volume ratio of alcohol and ketone is 1:1 to 2:1; said volume ratio of alcohol and arene is 4:1.

Form CS11 of the present disclosure has following advantages:

1) At present, there is no patent or literature about apabetalone's crystalline forms. The inventor of the present disclosure has solved this difficult problem after a lot of experimental research and found Form CS11, which is suitable for drug development.

2) Form CS11 has good stability. Form CS11 is stable for at least 6 weeks when stored under the condition of 25° C./60% RH and 40° C./75% RH. Form CS11 has excellent stability, which can ensure that the quality of the drug will not be affected as polymorphic transition will not occur in the process of preparation, transportation and storage. It is of great significance to ensure the efficacy and safety of the drug and prevent the occurrence of adverse drug reactions.

3) Form CS11 has excellent solubility, especially, the solubility in SGF of Form CS11 is as high as 0.71 mg/mL at 1 hour, and real-time solubilities in FeSSIF at 1 hour, 4 hours and 24 hours are all higher than 0.26 mg/mL. Highly soluble crystalline forms are conducive to improving drug's blood concentration and bioavailability.

According to the objective of the present disclosure, crystalline form CS4 of apabetalone is provided (hereinafter referred to as Form CS4). Said Form CS4 is an anhydrate.

The X-ray powder diffraction pattern of Form CS4 shows characteristic peaks at 2theta values of 9.1°±0.2°, 14.5°±0.2°, 23.5°±0.2° and 24.2°±0.2° using CuKα radiation.

Furthermore, the X-ray powder diffraction pattern of Form CS4 shows one or two or three characteristic peaks at 2theta values of 10.3°±0.2°, 25.0°±0.2° and 26.3°±0.2°. Preferably, the X-ray powder diffraction pattern of Form CS4 shows characteristic peaks at 2theta values of 10.3°±0.2°, 25.0°±0.2° and 26.3°±0.2°.

Furthermore, the X-ray powder diffraction pattern of Form CS4 shows one or two or three characteristic peaks at 2theta values of 10.8°±0.2°, 11.6°±0.2° and 19.5°±0.2°. Preferably, the X-ray powder diffraction pattern of Form CS4 shows characteristic peaks at 2theta values of 10.8°±0.2°, 11.6°±0.2° and 19.5°±0.2°.

In a preferred embodiment, the X-ray powder diffraction pattern of Form CS4 shows characteristic peaks at 2theta values of 9.1°±0.2°, 14.5°±0.2°, 23.5°±0.2°, 24.2°±0.2°, 10.3°±0.2°, 25.0°±0.2°, 26.3°±0.2°, 10.8°±0.2°, 11.6°±0.2° and 19.5°±0.2° using CuKα radiation.

Without any limitation being implied, in a specific embodiment the X-ray powder diffraction pattern of Form CS4 is substantially as depicted in FIG. 9A.

According to the objective of the present disclosure, a process for preparing Form CS4 of apabetalone is also provided. The process comprises: Heating Form CS11 of apabetalone to 200-220° C., and then Form CS4 of apabetalone was obtained.

Form CS4 of the present disclosure has the following advantages:

1) At present, there is no patent or literature about apabetalone's crystalline forms. The inventor of the present disclosure has solved this difficult problem after a lot of experimental research and found Form CS4, which is suitable for drug development.

2) Form CS4 has good long-term stability and mechanical stability. Form CS4 is stable for at least 10 months when stored under the condition of 25° C./60% RH and 40° C./75% RH. The stability of crystalline form is very important for drug development. Form CS4 has excellent stability, which can ensure that the quality of the drug will not be affected as polymorphic transition will not occur in the process of preparation, transportation and storage. It is of great significance to ensure the efficacy and safety of the drug and prevent the occurrence of adverse drug reactions. In addition, Form CS4 doesn't change after manual grinding, which indicates that Form CS4 has good mechanical stability. The grinding of APIs is usually needed in production process. Good grinding stability can reduce the risk of crystallinity change and polymorphic transition of APIs during production process.

3) Form CS4 of the present disclosure is almost non hygroscopic. The weight gain of Form CS4 of the present disclosure at 80% RH is 0.12% and the crystalline form doesn't change after DVS test. For almost non hygroscopic crystalline forms, it is not necessary to control the environmental humidity in production process. There is no special strict requirements for packaging and storage conditions. It saves costs and is easy to industrialize production and long-term storage of drugs. Because the storage conditions are not demanding, the cost of material storage and quality control will be greatly reduced, which has strong economic value and is more suitable for medicinal use.

In the processes for preparation of Form CS2, Form CS8, Form CS13, Form CS20, Form CS1, Form CS7, Form CS9, Form CS11 and Form CS4 of the present disclosure:

Said "room temperature" is not an specific temperature value and refers to 10-30° C.

Said "evaporating" is accomplished by using a conventional method in the field. Slow evaporation is accomplished in a container covered by sealing film with pinholes. Rapid evaporation is accomplished in an open container.

Said "stirring" is accomplished by using a conventional method in the field such as magnetic stirring or mechanical stirring. The stirring speed is 50 to 1800 r/min, preferably is 300 to 900 r/min.

Said "cooling" is accomplished by using conventional methods in the field such as slow cooling and rapid cooling. Slow cooling is usually accomplished at a speed of 0.1° C./min. Rapid cooling is usually accomplished by transferring the sample directly from high temperature environment to low temperature environment.

In the present disclosure, "crystal" or "crystalline form" refers to the crystal or the crystalline form being identified by the X-ray diffraction pattern shown herein. Those skilled in the art are able to understand that physicochemical properties discussed herein can be characterized. The experimental errors depend on the instrument conditions, the sampling processes and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be taken into account. An error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exactly same X-ray diffraction pattern of the example shown herein. As used herein, "the same XRPD pattern" does not mean absolutely the same, the same peak positions may differ by ±0.2° and the peak intensity allows for some variability. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, Form CS2, Form CS8, Form CS13, Form CS20, Form CS1, Form CS7, Form CS9, Form CS11 and Form CS4 of the present disclosure are pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the number and the number range should not be understood as the number or number range themselves only. It should be understood by those skilled in the art that the specific number can be shifted at specific technical environment without departing from the spirit and principle of the present disclosure. In the present disclosure, the number of shift ranges expected by one of skilled in the art is represented by the term "about".

The present disclosure also provides a mixed crystalline form of apabetalone, which contains more than two crystalline forms of Form CS2, Form CS8, Form CS13, Form CS20, Form CS1, Form CS7, Form CS9, Form CS11 and Form CS4 in any proportion.

In addition, the present disclosure provides a pharmaceutical composition, said pharmaceutical composition comprises a therapeutically and/or prophylactically effective amount of Form CS2, Form CS8, Form CS13, Form CS20, Form CS1, Form CS7, Form CS9, Form CS11 and Form CS4 and at least one pharmaceutically acceptable carriers, diluents or excipients.

Furthermore, Form CS2, Form CS8, Form CS13, Form CS20, Form CS1, Form CS7, Form CS9, Form CS11 and Form CS4 can be used for preparing drugs treating cardiovascular, cholesterol or lipid-related disorders.

Furthermore, Form CS2, Form CS8, Form CS13, Form CS20, Form CS1, Form CS7, Form CS9, Form CS11 and Form CS4 can be used for preparing drugs preventing and treating cardiovascular diseases and diabetes, especially for preparing drugs treating atherosclerosis, acute coronary syndrome and predecessor diabetes.

DETAILED DESCRIPTION

Figure 1A:
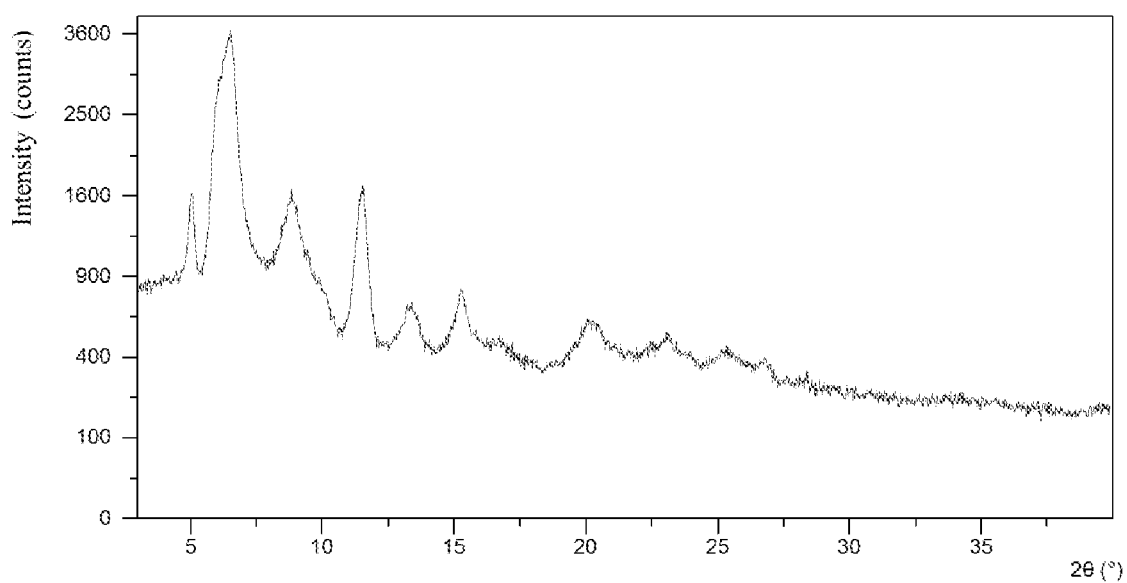
FIG. 1A shows an XRPD pattern of Form CS2 according to example 1 of the present disclosure.

The present disclosure is further illustrated by the following examples which describe the preparation and use of the crystalline forms of the present disclosure in detail. It is obvious to those skilled in the art that many changes in the materials and methods can be accomplished without departing from the scope of the present disclosure.

The abbreviations used in the present disclosure are explained as follows:

XRPD: X-ray Powder Diffraction
HPLC: High Performance Liquid Chromatography
DVS: Dynamic Vapor Sorption
TGA: Thermal Gravimetric Analysis
$^1$H NMR: Proton Nuclear Magnetic Resonance
RH: Relative Humidity Instruments and Methods Used for Data Collection:

X-ray powder diffraction patterns in the present disclosure were acquired by a Panalytical Empyrean X-ray powder diffractometer. The parameters of the X-ray powder diffraction method of the present disclosure were as follows:

X-ray Reflection: Cu, Kα
Kα1 (Å): 1.5400598; Kα2 (Å): 1.544426
Kα2/Kα1 intensity ratio: 0.50
Voltage: 45 (kV)
Current: 40 (mA)
Scan range: from 3.0 degree to 40.0 degree Differential scanning calorimetry (DSC) data in the present disclosure were acquired by a TA Instruments Q200 MDSC. Instrument control software is Thermal Advantage, and analysis software is Universal Analysis.

Heating rate: 10° C./min
Purge gas: nitrogen

Thermal gravimetric analysis (TGA) data in the present disclosure were acquired by a TA Instruments Q500 TGA. Instrument control software is Thermal Advantage, and analysis software is Universal Analysis.

Heating rate: 10° C./min
Purge gas: nitrogen

Proton nuclear magnetic resonance spectrum data ($^1$H NMR) were collected from a Bruker Avance II DMX 400M HZ NMR spectrometer. 1-5 mg of sample was weighed, and dissolved in 0.5 mL of deuterated dimethyl sulfoxide to obtain a solution with a concentration of 2-10 mg/mL.

Dynamic Vapor Sorption (DVS) was measured via a SMS (Surface Measurement Systems Ltd.) intrinsic DVS instrument. Its control software is DVS—Intrinsic control software, and its analysis software is DVS—Intrinsic Analysis software. Typical Parameters for DVS test are as follows:

Temperature: 25° C.
Gas and flow rate: $N_2$, 200 mL/min
dm/dt: 0.002%/min
RH range: 0% RH to 95% RH High Performance Liquid Chromatography (HPLC) data in the present disclosure were collected from an Agilent 1260 with Diode Array Detector (DAD). The HPLC method parameters for purity test in the present disclosure are as follows:

1. Column: Waters XBridge C18 150×4.6 mm, 5 μm
2. Mobile Phase: A: 0.1% TFA in $H_2O$
   B: 0.1% TFA in Acetonitrile
Gradient:

| Time (min) | % B |
|---|---|
| 0.0 | 20 |
| 5.0 | 30 |
| 6.0 | 80 |
| 8.0 | 80 |
| 8.1 | 20 |
| 10.0 | 20 |

3. Flow rate: 1.6 mL/min
4. Injection Volume: 5 μL
5. Detection wavelength: 260 nm
6. Column Temperature: 40° C.
7. Diluent: Acetonitrile/$H_2O$ (v/v, 1/1)

The dissolution testing in the present disclosure was performed on an Agilent 708-DS.

Unless otherwise specified, the following examples were conducted at room temperature.

Raw materials of apabetalone used in the following examples were prepared by known methods disclosed in CN101641339B.

Example 1

Preparation of Form CS2

Certain amount of apabetalone was weighed and dissolved in corresponding solvent of Table 1.1 at $T_1$. The solution was filtered and cooled to $T_2$ slowly or rapidly. When precipitation occurred, solids was obtained after centrifugation and drying.

TABLE 1.1

| Sample No. | Weight (mg) | Solvent (v/v) | Volume (mL) | Cooling rate | $T_1$ (° C.) | $T_2$ (° C.) |
|---|---|---|---|---|---|---|
| 1-a | 19.7 | Methanol | 1.0 | Rapid | 50 | −20 |
| 1-b | 10.2 | Methanol/methyl isobutyl ketone (1:1) | 1.0 | Slow | 50 | 5 |
| 1-c | 10.2 | Methanol/methyl isobutyl ketone (1:1) | 1.0 | Rapid | 50 | −20 |
| 1-d | 20.2 | Methanol/toluene (1:1) | 1.0 | Slow | 50 | 5 |
| 1-e | 20.2 | Methanol/toluene (1:1) | 1.0 | Rapid | 50 | −20 |
| 1-f | 11.3 | Methanol/2-methyl tetrahydrofuran (1:1) | 1.0 | Slow | 50 | 5 |
| 1-g | 11.3 | Methanol/2-methyl tetrahydrofuran (1:1) | 1.0 | Rapid | 50 | −20 |
| 1-h | 10.7 | Tetrahydrofuran/methyl tert-butyl ether (2:1) | 3.0 | Slow | 50 | 5 |
| 1-i | 19.9 | Methanol | 1.0 | Rapid | 100 | −20 |

Figure 1B:
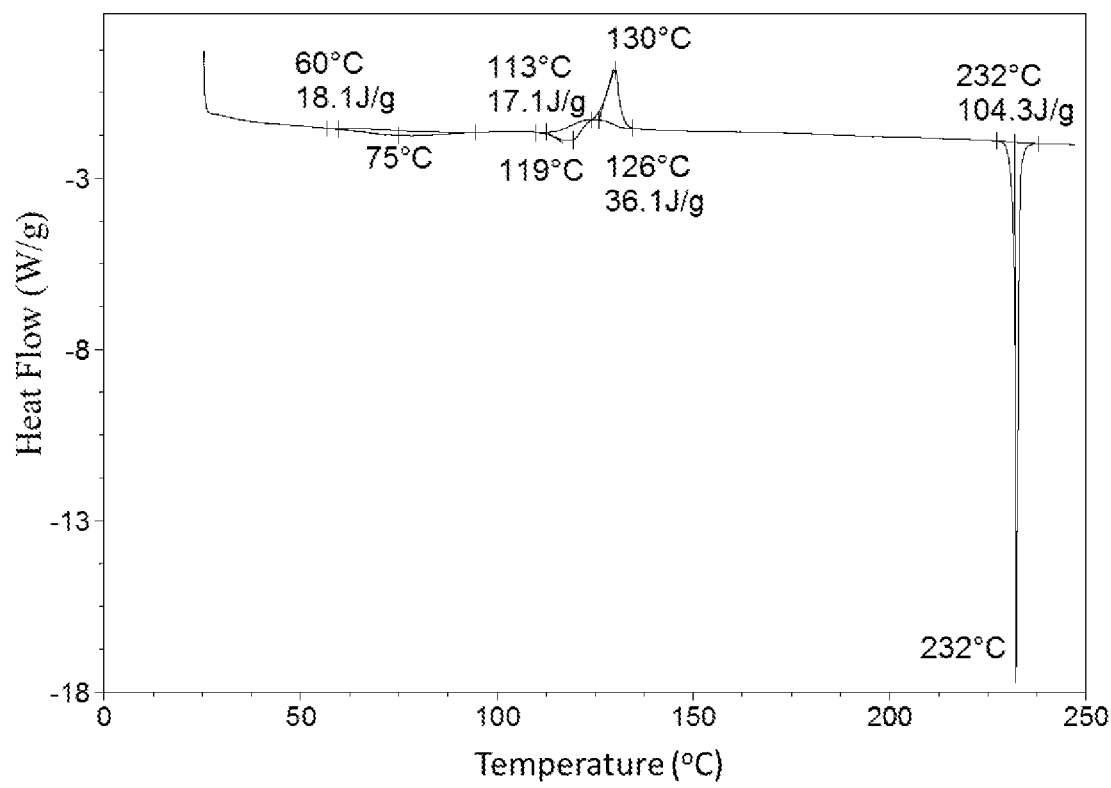
FIG. 1B shows a DSC curve of Form CS2 according to example 1 of the present disclosure.
Figure 1C:
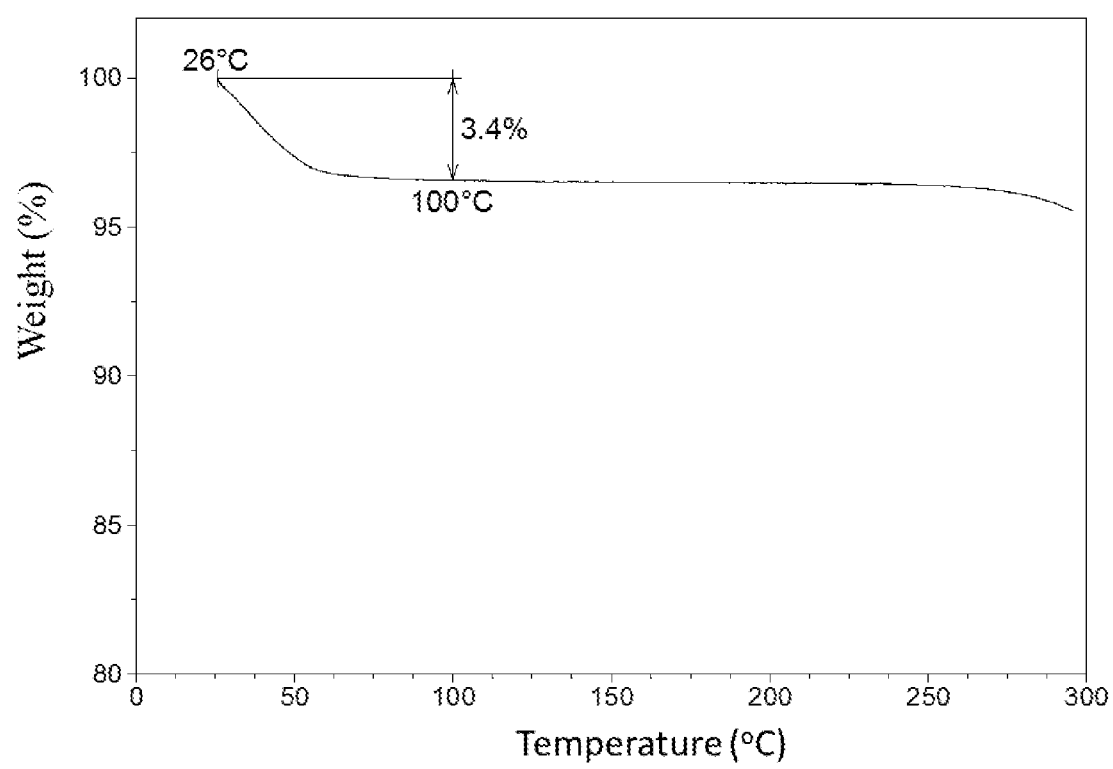
FIG. 1C shows a TGA curve of Form CS2 according to example 1 of the present disclosure.

Sample 1-a to 1-i were confirmed to be Form CS2 by XRPD. Sample 1-i was selected for characterization. The XRPD pattern is substantially as depicted in FIG. 1A, and the XRPD data are listed in Table 1.2. The DSC curve of Form CS2 is substantially as depicted in FIG. 1B, which shows the first endothermic peak at around 60° C., the second endothermic peak at around 113° C., the first exothermic peak at around 126° C. and the third endothermic peak at around 232° C. The TGA curve of Form CS2 is substantially as depicted in FIG. 1C, which shows about 3.4% weight loss when heated to 100° C.

TABLE 1.2

| 2 Theta | d spacing | Intensity % |
|---|---|---|
| 5.08 | 17.39 | 30.31 |
| 6.57 | 13.46 | 100.00 |
| 8.85 | 10.00 | 34.56 |
| 11.54 | 7.67 | 41.68 |
| 13.31 | 6.65 | 8.72 |
| 15.28 | 5.80 | 14.13 |
| 20.22 | 4.39 | 7.21 |
| 23.10 | 3.85 | 4.08 |
| 25.35 | 3.51 | 2.44 |

Solubility Study of Form CS2

The prepared apabetalone Form CS2 was suspended into SGF (simulated gastric fluids) and FeSSIF (fed state simulated intestinal fluids, pH=5.0) to obtain saturated solutions. After being equilibrated for 1 h and 24 h, concentrations of the saturated solutions were measured by HPLC. The results are listed in Table 1.3.

TABLE 1.3

| | Solubility (mg/mL) | |
|---|---|---|
| Time (h) | SGF | FeSSIF |
| 1 | 0.49 | 0.15 |
| 24 | 0.61 | 0.24 |

The above results show that Form CS2 of apabetalone has good solubility in SGF and FeSSIF, especially in SGF, the solubility at 24 h is as high as 0.61 mg/mL. Polymorph with high solubility is conducive to increasing the blood concentration of drugs in human body and improves the bioavailability of drugs, which is of great significance for drug research.

Example 2

Preparation of Form CS8

Certain amount of apabetalone was weighed and dissolved in corresponding solvent of Table 2.1 at $T_1$. The solution was filtered and cooled to $T_2$ slowly or rapidly. When precipitation occurred, solids was obtained after centrifugation and drying.

TABLE 2.1

| Sample No. | Weight (mg) | Solvent (v/v) | Volume (mL) | Cooling rate | $T_1$ (° C.) | $T_2$ (° C.) |
|---|---|---|---|---|---|---|
| 2-a | 9.8 | Dichloromethane | 1.5 | Slow | 50 | 5 |
| 2-b | 9.8 | Dichloromethane | 1.5 | Rapid | 50 | −20 |
| 2-c | 20.8 | Dichloromethane/isopropanol (4:1) | 1.0 | Slow | 50 | 5 |
| 2-d | 20.8 | Dichloromethane/isopropanol (4:1) | 1.0 | Rapid | 50 | −20 |

Figure 2A:
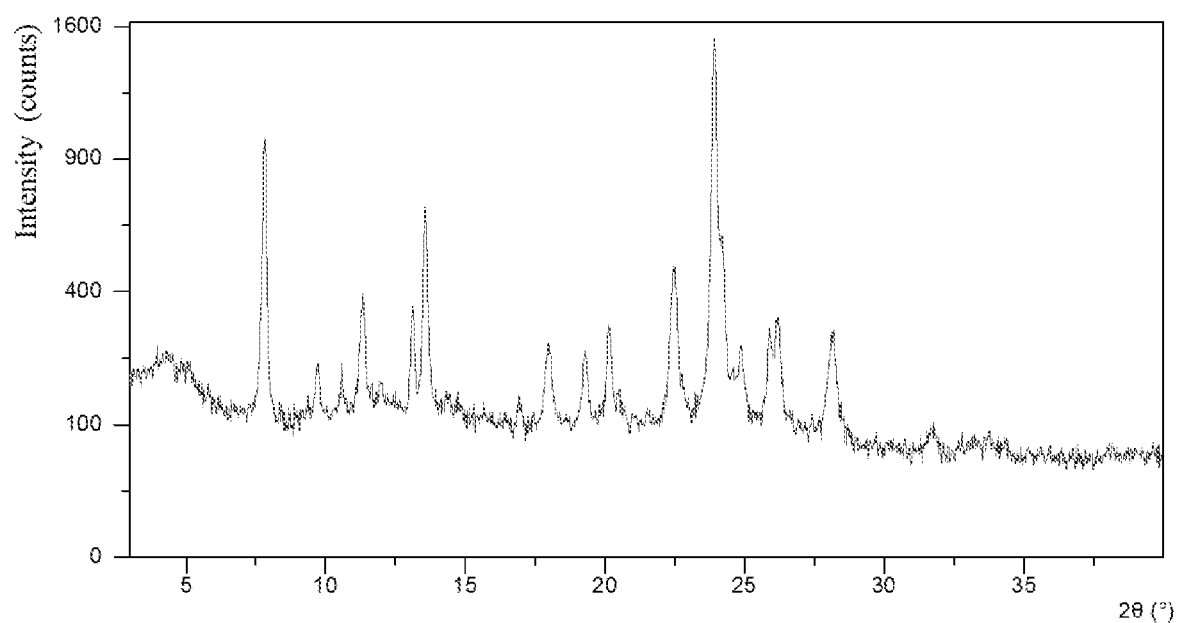
FIG. 2A shows an XRPD pattern of Form CS8 according to example 2 of the present disclosure.
Figure 2B:
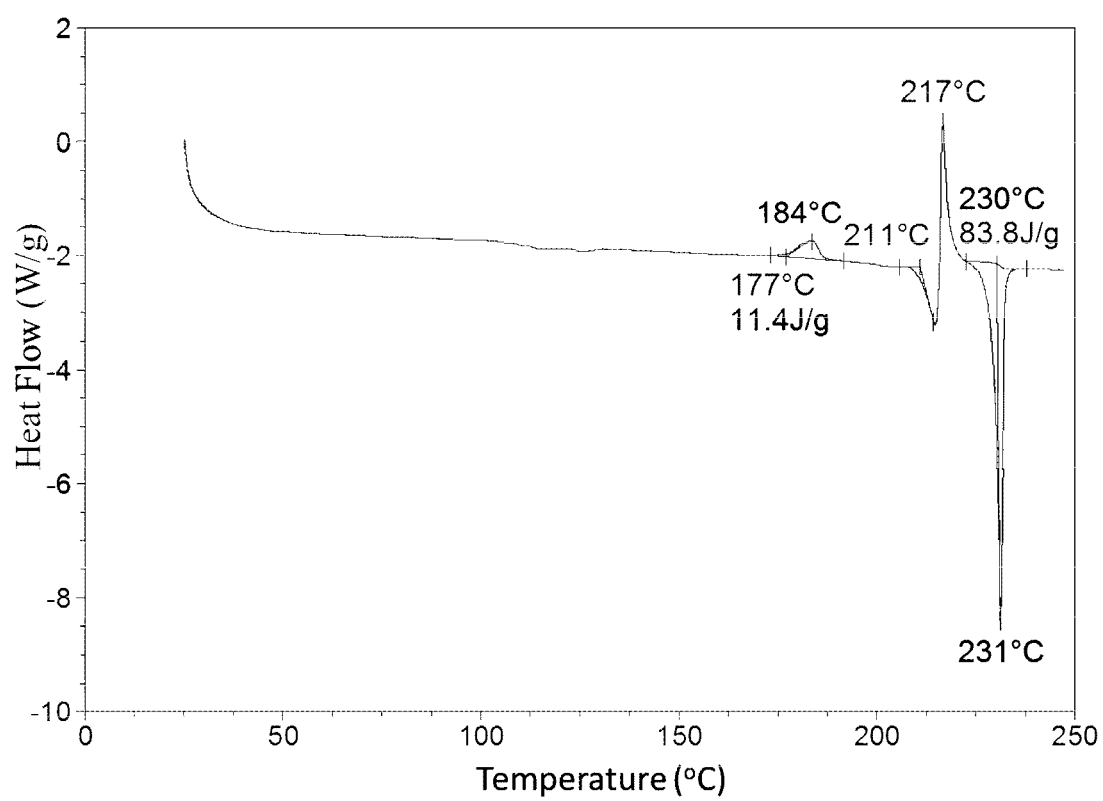
FIG. 2B shows a DSC curve of Form CS8 according to example 2 of the present disclosure.
Figure 2C:
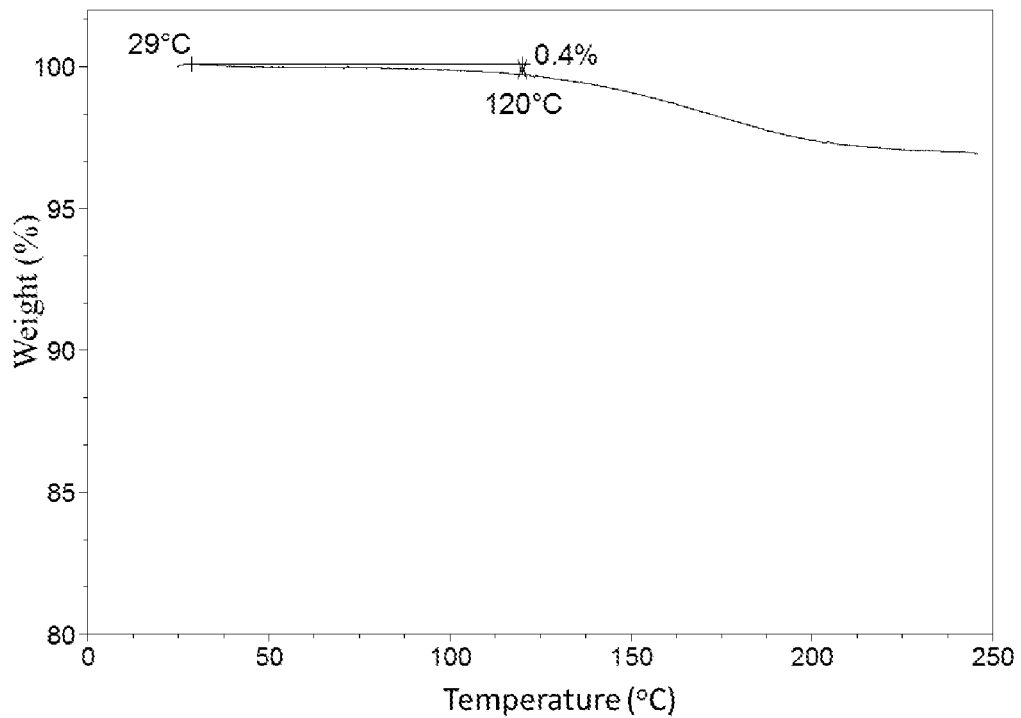
FIG. 2C shows a TGA curve of Form CS8 according to example 2 of the present disclosure.

Sample 2-a to 2-d were confirmed to be Form CS8 by XRPD. Sample 2-a was selected for characterization. The XRPD pattern is substantially as depicted in FIG. 2A, and the XRPD data are listed in Table 2.2. The DSC curve of Form CS8 is substantially as depicted in FIG. 2B, which shows the first exothermic peak at around 177° C., the first endothermic peak at around 211° C., the second exothermic peak at around 217° C. and the second endothermic peak at around 230° C. The TGA curve of Form CS8 is substantially as depicted in FIG. 2C, which shows about 0.4% weight loss when heated to 120° C.

TABLE 2.2

| 2 Theta | d spacing | Intensity % |
|---|---|---|
| 4.23 | 20.89 | 3.93 |
| 7.83 | 11.30 | 60.72 |
| 9.74 | 9.08 | 6.55 |
| 10.58 | 8.36 | 5.86 |
| 11.36 | 7.79 | 16.82 |
| 13.11 | 6.75 | 16.65 |
| 13.55 | 6.54 | 40.35 |
| 18.00 | 4.93 | 10.44 |
| 19.29 | 4.60 | 9.65 |
| 20.17 | 4.40 | 14.20 |
| 22.47 | 3.96 | 25.75 |
| 23.91 | 3.72 | 100.00 |
| 24.22 | 3.67 | 32.56 |
| 24.87 | 3.58 | 11.65 |
| 25.88 | 3.44 | 14.42 |
| 26.18 | 3.40 | 17.03 |
| 28.16 | 3.17 | 14.65 |
| 31.72 | 2.82 | 2.11 |

Stability Study of Form CS8
Stability Study of Apabetalone Form CS8

Figure 2D:
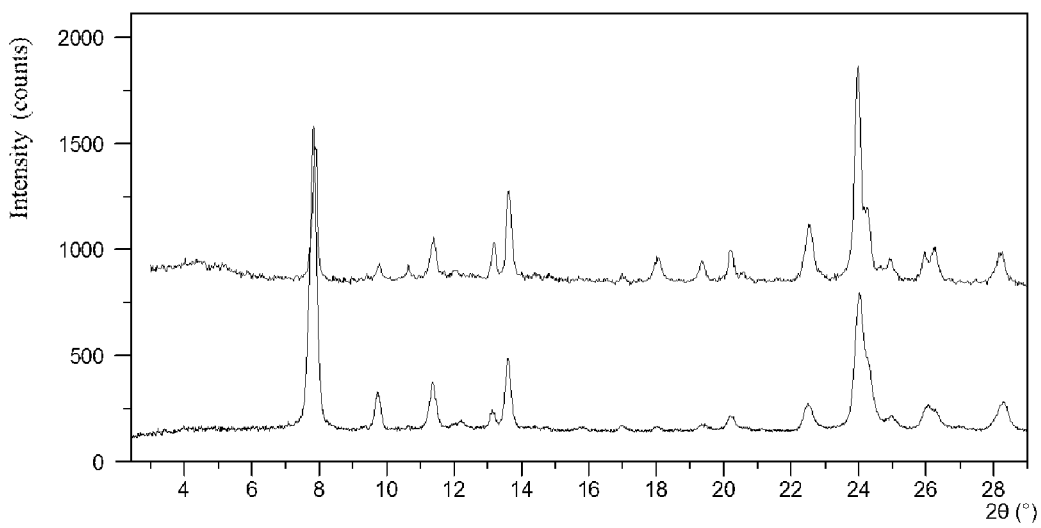
FIG. 2D shows an XRPD pattern overlay of Form CS8 before and after being stored under 25° C./60% RH for two weeks (from top to bottom: XRPD pattern before storage, XRPD pattern after being stored under 25° C./60% RH for two weeks).

Form CS8 was placed in a constant temperature and humidity chamber at 25° C./60% RH for 2 weeks in open dish. Crystalline form of the sample were tested by XRPD and impurity of the sample were checked. The results are shown in FIG. 2D (From top to bottom: XRPD pattern of Form CS8 before and after being stored under 25° C./60% RH for 2 weeks.)

No obvious form change and purity decrease was observed for Form CS8 after being stored under 25° C./60% RH for 2 weeks. The results show that Form CS8 has good stability.

Solubility Study of Form CS8

The prepared Form CS8 was suspended into SGF (simulated gastric fluids) and FeSSIF (fed state simulated intestinal fluids, pH=5.0) to obtain saturated solutions. After being equilibrated for 1 h, concentrations of the saturated solutions were measured by HPLC. The results are listed in Table 2.3.

TABLE 2.3

| | Solubility (mg/mL) | |
|---|---|---|
| Time (h) | SGF | FeSSIF |
| 1 | 0.43 | 0.28 |

The above results show that Form CS8 of apabetalone has good solubility in SGF and FeSSIF. Polymorph with high solubility is beneficial to increase the blood concentration of drugs in human body and improve the bioavailability of drugs, which is of great significance for drug research.

Hygroscopicity of Form CS8

Figure 2E:
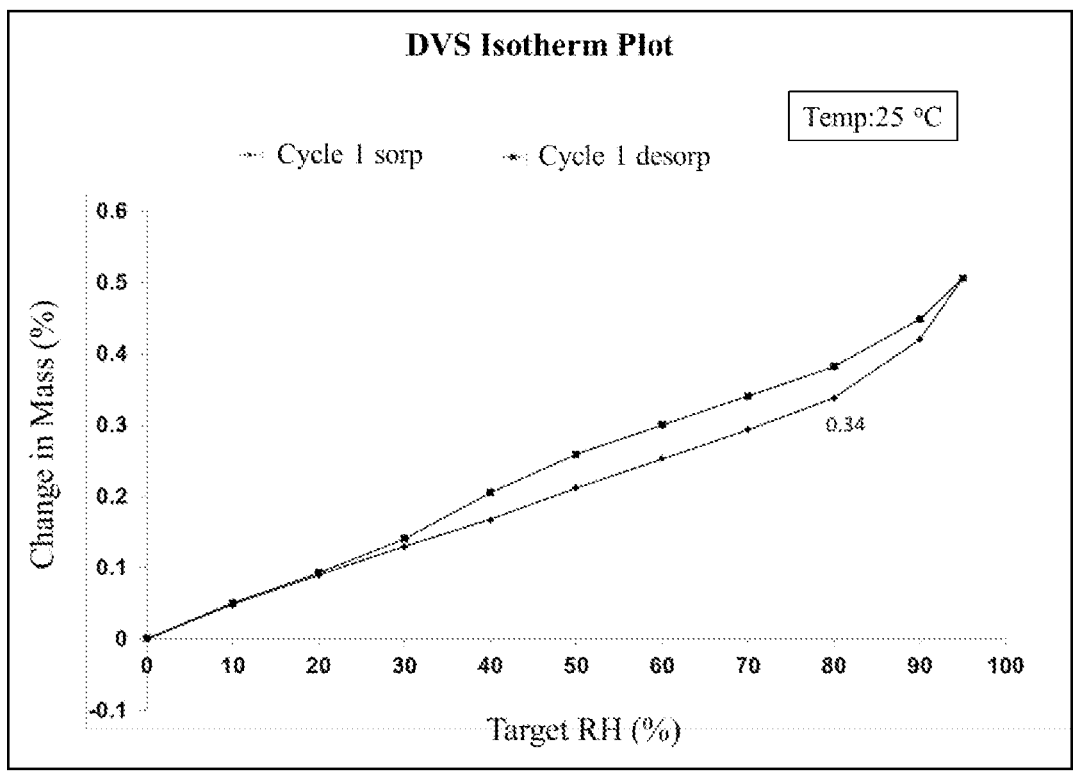
FIG. 2E shows a DVS plot of Form CS8 according to example 2 of the present disclosure.

Dynamic vapor sorption (DVS) was applied to test hygroscopicity of Form CS8 in the present disclosure with about 10 mg of sample. The result is listed in Table 2.4. The DVS plot of Form CS8 is substantially as depicted in FIG. 2E.

TABLE 2.4

| Form | Weight Gain under 80% Relative Humidity |
|---|---|
| Form CS8 | 0.34% |

Description and definition of hygroscopicity (Chinese Pharmacopoeia 2015 edition appendix 9103 drug hygroscopic test guidelines, test at 25° C.+/−1° C., 80% RH.).

deliquescent: Sufficient water is absorbed to form a liquid;
very hygroscopic: Increase in mass is equal to or greater than 15 percent;
hygroscopic: Increase in mass is less than 15 percent and equal to or greater than 2 percent;
slightly hygroscopic: Increase in mass is less than 2 percent and equal to or greater than 0.2 percent.
non hygroscopic or almost non hygroscopic: Increase in mass is less than 0.2%.

Figure 2F:
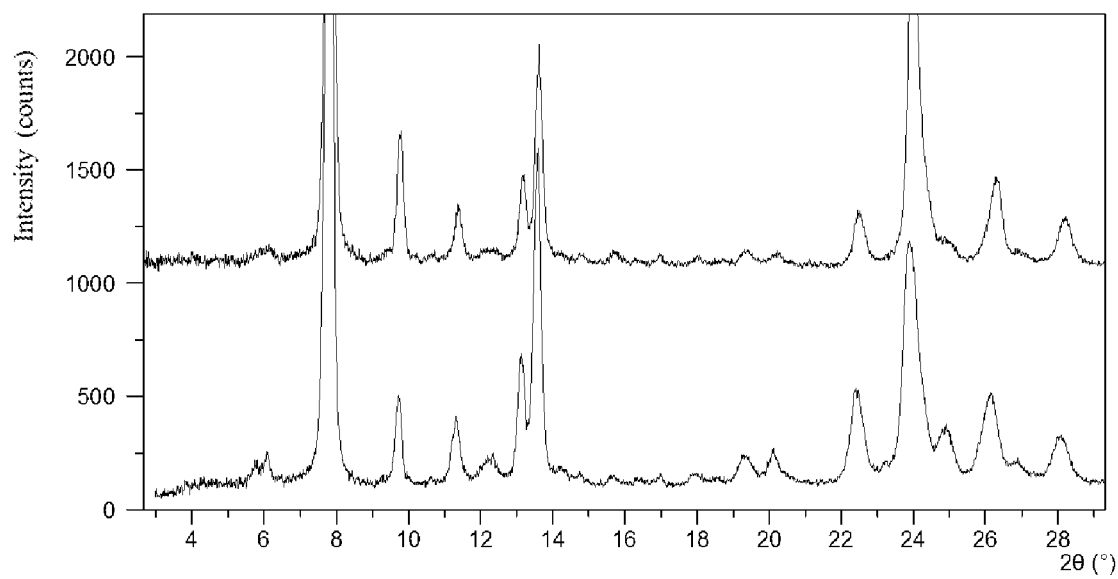
FIG. 2F shows an XRPD pattern overlay of Form CS8 according to example 2 of the present disclosure before and after DVS test.

The results indicates that the weight gain of Form CS8 under 80% RH is 0.34%. According to the definition of hygroscopicity, Form CS8 is slightly hygroscopic. The XRPD pattern of Form CS8 after DVS test is shown in FIG. 2F. No form change was observed for Form CS8 after DVS test, which indicates that Form CS8 is stable under the influence of humidity.

Form CS8 of the present disclosure shows low hygroscopicity and can avoid the problems such as crystal instability in the process of drug preparation and/or storage, as well as the unprocessability of the preparation caused by external factors such as environmental moisture, which is conducive to the accurate quantitative preparation and later transportation and storage.

Example 3

Preparation of Form CS13

Certain amount of apabetalone was weighed and dissolved in corresponding solvent shown in Table 3.1. The solution was filtered and evaporated slowly at room temperature with or without addition of polymer to obtain solid.

TABLE 3.1

| Sample No. | Weight (mg) | Solvent (v/v) | Volume (mL) | Whether to add polymer (Y/N) | T (° C.) |
|---|---|---|---|---|---|
| 3-a | 10.8 | Tetrahydrofuran/water (4:1) | 1.3 | N | 25 |
| 3-b | 10.5 | Acetone/water (9:1) | 3.3 | N | 25 |
| 3-c | 10.8 | Tetrahydrofuran/water (4:1) | 1.3 | Y | 25 |
| 3-d | 10.5 | Acetone/water (9:1) | 3.3 | Y | 25 |

Said polymer is a mixture of equal masses of polycaprolactone, polyethylene glycol, polymethyl methacrylate, sodium alginate and hydroxyethyl cellulose.

Figure 3A:
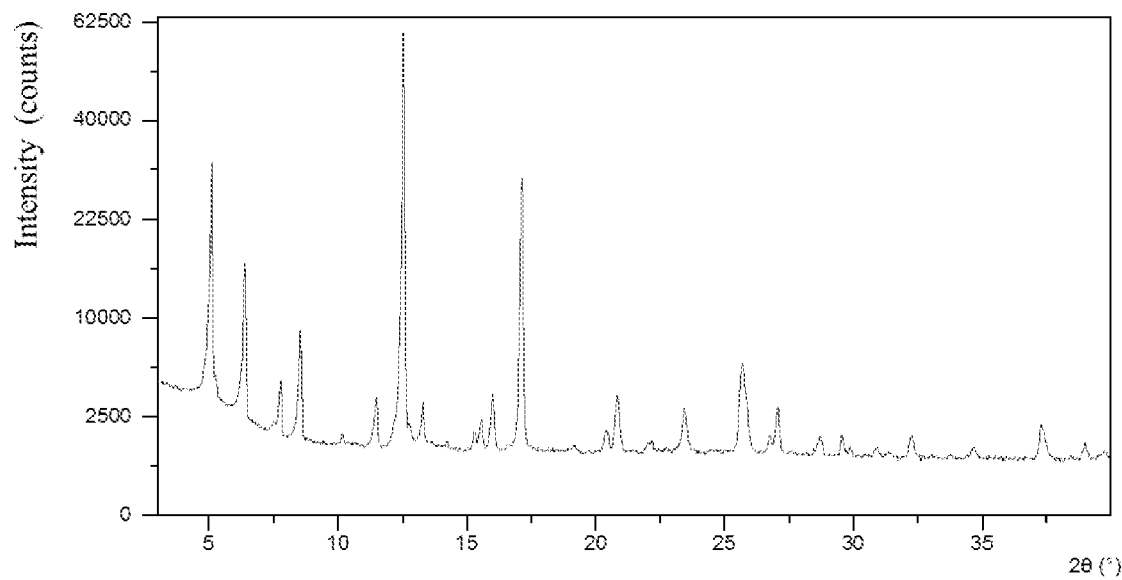
FIG. 3A shows an XRPD pattern of Form CS13 according to example 3 of the present disclosure.
Figure 3B:
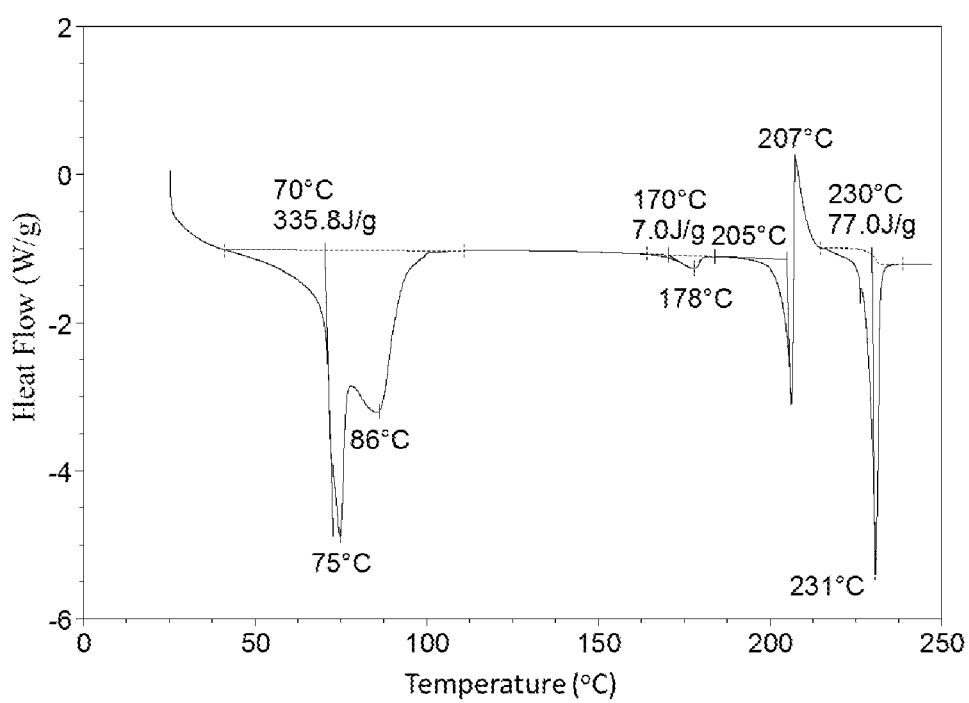
FIG. 3B shows a DSC curve of Form CS13 according to example 3 of the present disclosure.
Figure 3C:
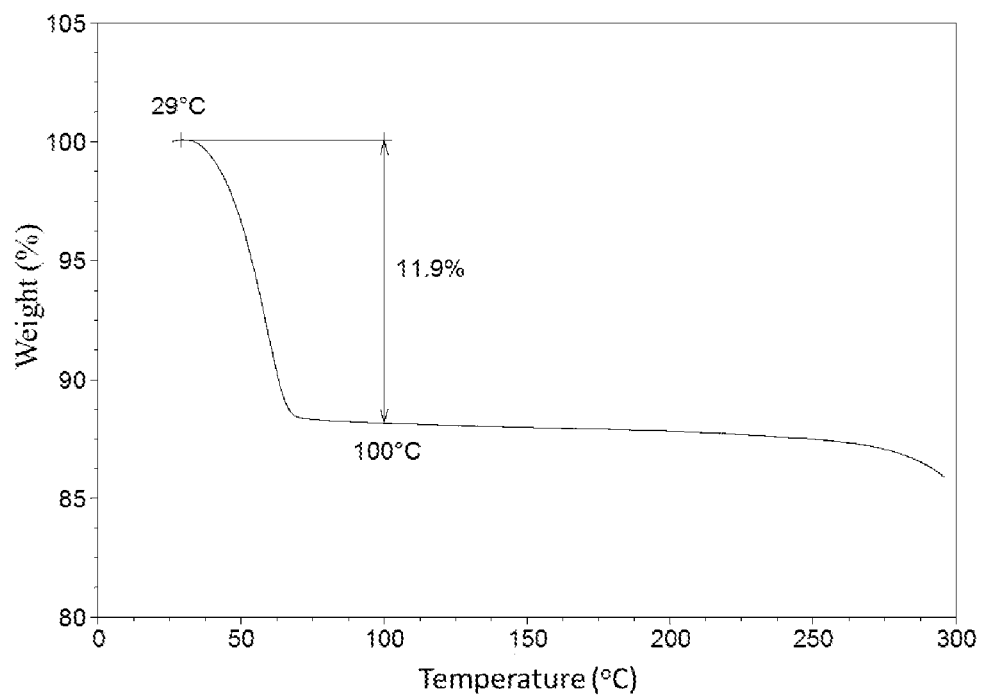
FIG. 3C shows a TGA curve of Form CS13 according to example 3 of the present disclosure.

Sample 3-a to 3-d were confirmed to be Form CS13 by XRPD. Sample 3-d was selected for characterization. The XRPD pattern is substantially as depicted in FIG. 3A, and the XRPD data are listed in Table 3.2. The DSC curve of Form CS13 is substantially as depicted in FIG. 3B, which shows the first endothermic peak at around 70° C., the second endothermic peak at around 86° C., the third endothermic peak at around 170° C., the fourth endothermic peak at around 205° C., the first exothermic peak at around 207° C. and the fifth endothermic peak at around 230° C. The TGA curve of Form CS13 is substantially as depicted in FIG. 3C, which shows about 11.9% weight loss when heated to 100° C.

TABLE 3.2

| 2 Theta | d spacing | Intensity % |
|---|---|---|
| 5.09 | 17.35 | 48.06 |
| 6.38 | 13.85 | 22.94 |
| 7.76 | 11.39 | 4.83 |
| 8.54 | 10.35 | 12.25 |
| 10.17 | 8.70 | 0.71 |
| 11.48 | 7.71 | 3.89 |
| 12.54 | 7.06 | 100.00 |
| 13.29 | 6.66 | 3.59 |
| 15.30 | 5.79 | 1.21 |
| 15.56 | 5.69 | 2.14 |
| 16.01 | 5.54 | 4.65 |
| 17.13 | 5.18 | 47.37 |
| 19.15 | 4.64 | 0.27 |
| 20.41 | 4.35 | 1.35 |
| 20.84 | 4.26 | 4.59 |
| 22.11 | 4.02 | 0.59 |
| 23.43 | 3.80 | 3.37 |
| 25.67 | 3.47 | 8.18 |
| 26.75 | 3.33 | 1.24 |
| 27.06 | 3.29 | 3.65 |
| 28.72 | 3.11 | 1.18 |
| 29.56 | 3.02 | 1.42 |
| 30.89 | 2.90 | 0.43 |
| 32.26 | 2.77 | 1.36 |
| 34.67 | 2.59 | 0.58 |
| 37.28 | 2.41 | 2.20 |
| 38.97 | 2.31 | 0.89 |

Solubility of Form CS13

The prepared Form CS13 was suspended into SGF (simulated gastric fluids) and FeSSIF (fed state simulated intestinal fluids, pH=5.0) to obtain saturated solutions. After being equilibrated for 1 h, 4 h and 24 h, concentrations of the saturated solutions were measured by HPLC. The results are listed in Table 3.3.

TABLE 3.3

| Time (h) | Solubility (mg/mL) | |
|---|---|---|
| | SGF | FeSSIF |
| 1 | 0.35 | 0.13 |
| 4 | 0.31 | 0.14 |
| 24 | 0.33 | 0.14 |

The above results show that Form CS13 of apabetalone has good solubility in SGF and FeSSIF.

Example 4

Preparation of Form CS20

Certain amount of apabetalone was weighed and dissolved in corresponding solvent of Table 4.1. The solution was filtered and evaporated slowly at room temperature to obtain a solid.

TABLE 4.1

| Sample No. | Weight (mg) | Solvent (v/v) | Volume (mL) | T (° C.) |
|---|---|---|---|---|
| 4-a | 10.5 | Acetonitrile/acetic acid (9:1) | 2.0 | 25 |
| 4-b | 10.3 | Ethyl acetate/acetic acid (4:1) | 1.7 | 25 |

Figure 4A:
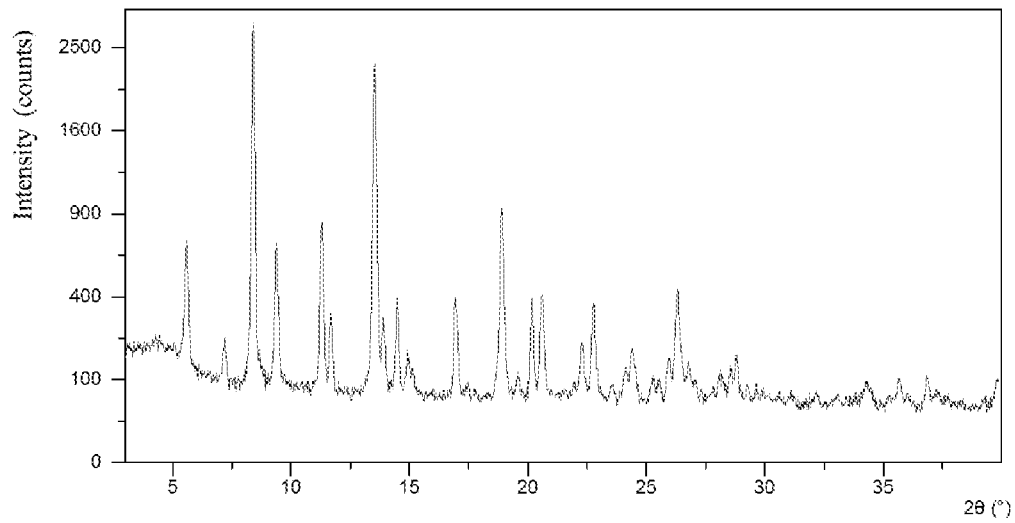
FIG. 4A shows an XRPD pattern of Form CS20 according to example 4 of the present disclosure.
Figure 4B:
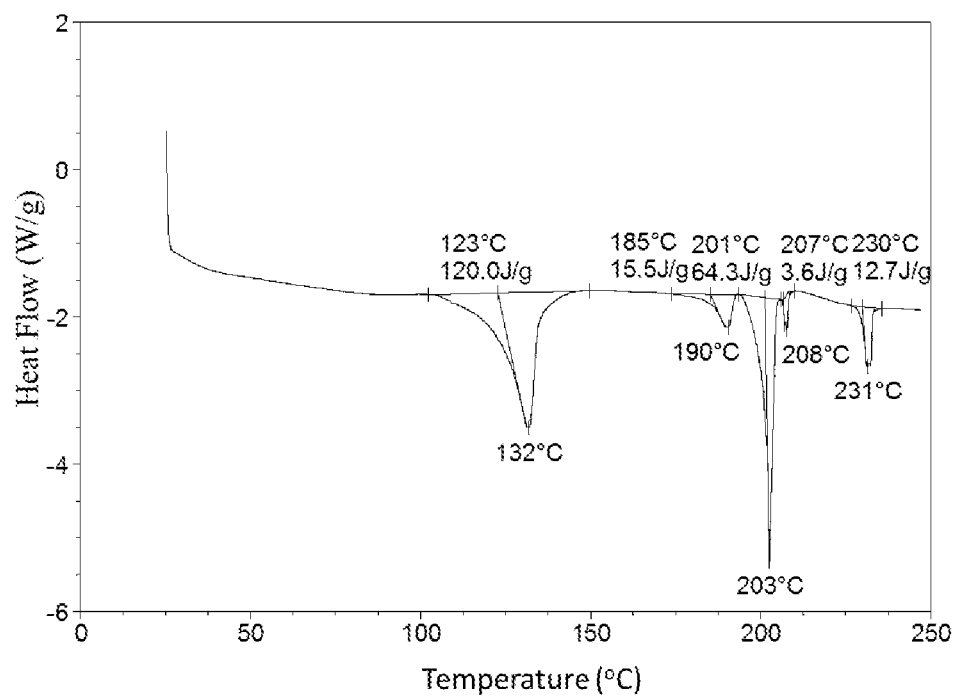
FIG. 4B shows a DSC curve of Form CS20 according to example 4 of the present disclosure.
Figure 4C:
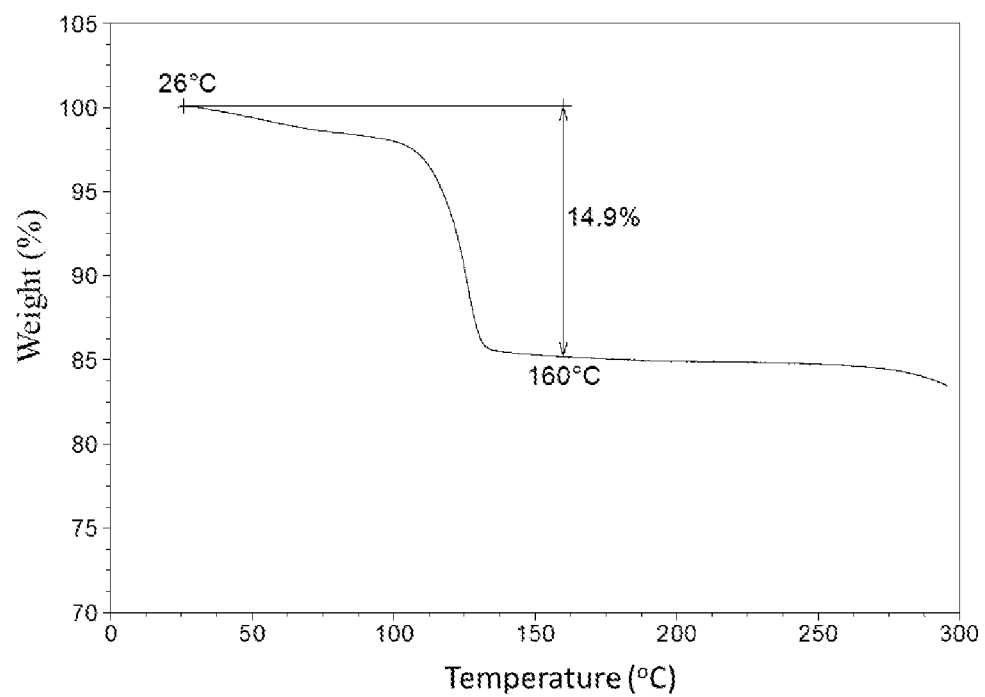
FIG. 4C shows a TGA curve of Form CS20 according to example 4 of the present disclosure.
Figure 4D:
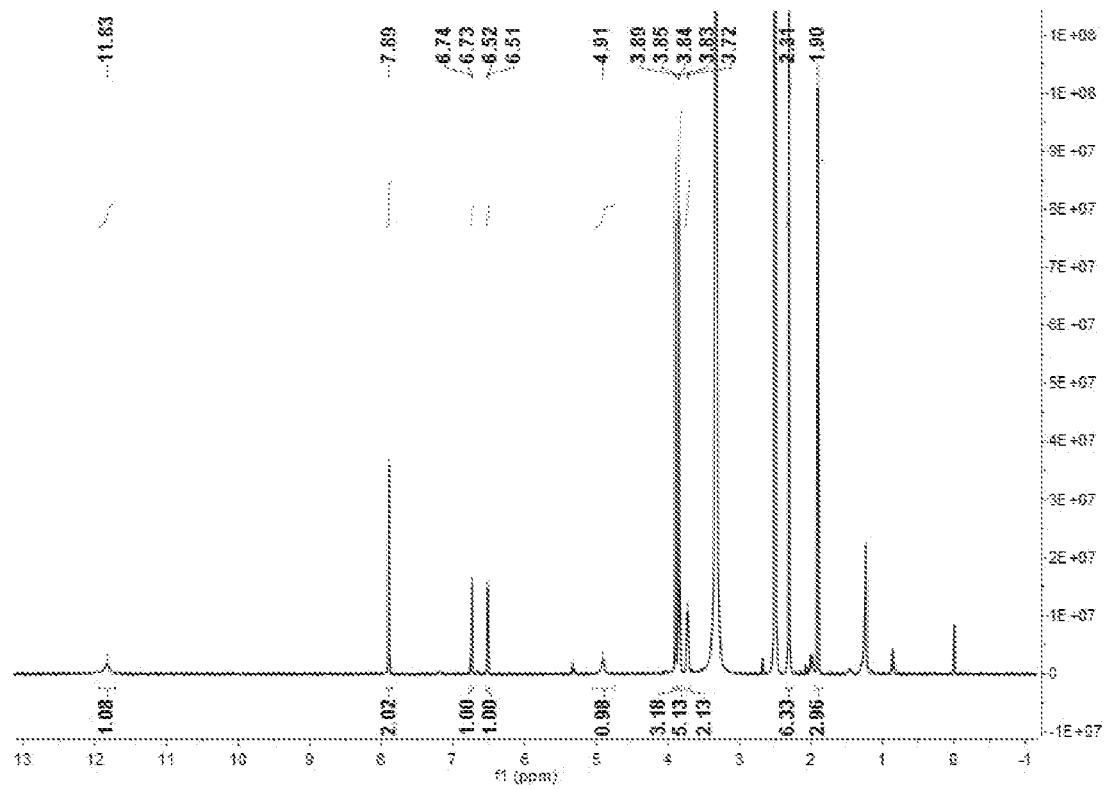
FIG. 4D shows a $^1$H NMR spectrum of Form CS20 according to example 4 of the present disclosure.

Sample 4-a to 4-b were confirmed to be Form CS20 of apabetalone by XRPD. Sample 4-a was selected for characterization. The XRPD pattern is substantially as depicted in FIG. 4A, and the XRPD data are listed in Table 4.2. The DSC curve of Form CS20 is substantially as depicted in FIG. 4B, which shows the first endothermic peak at around 123° C., the second endothermic peak at around 185° C., the third endothermic peak at around 201° C., the fourth endothermic peak at around 207° C. and the fifth endothermic peak at around 230° C. The TGA curve of Form CS13 is substantially as depicted in FIG. 4C, which shows about 14.9% weight loss when heated to 160° C. The $^1$H NMR spectrum of Form CS20 is substantially as depicted in FIG. 4D, and the corresponding data are: $^1$H NMR (400 MHz, DMSO) δ 11.83 (s, 1H), 7.89 (s, 2H), 6.74 (d, J=2.3 Hz, 1H), 6.52 (d, J=2.3 Hz, 1H), 4.91 (s, 1H), 3.89 (s, 3H), 3.87-3.81 (m, 5H), 3.72 (s, 2H), 2.31 (s, 6H), 1.90 (s, 3H).

TABLE 4.2

| 2 Theta | d spacing | Intensity % |
|---|---|---|
| 5.59 | 15.81 | 21.68 |
| 7.20 | 12.28 | 4.52 |
| 8.39 | 10.53 | 100.00 |
| 9.37 | 9.44 | 22.64 |
| 11.26 | 7.86 | 25.84 |
| 11.67 | 7.58 | 8.95 |
| 13.52 | 6.55 | 83.84 |
| 13.88 | 6.38 | 7.82 |
| 14.48 | 6.12 | 11.79 |
| 14.92 | 5.94 | 3.42 |
| 16.92 | 5.24 | 11.24 |
| 18.88 | 4.70 | 30.97 |
| 19.57 | 4.54 | 1.85 |
| 20.15 | 4.41 | 12.22 |
| 20.56 | 4.32 | 12.06 |
| 22.30 | 3.99 | 5.29 |
| 22.76 | 3.91 | 10.73 |
| 24.10 | 3.69 | 2.41 |
| 24.38 | 3.65 | 4.37 |

TABLE 4.2-continued

| 2 Theta | d spacing | Intensity % |
|---|---|---|
| 25.26 | 3.53 | 1.52 |
| 25.93 | 3.44 | 3.39 |
| 26.33 | 3.38 | 13.70 |
| 26.78 | 3.33 | 3.08 |
| 28.11 | 3.17 | 2.02 |
| 28.81 | 3.10 | 3.75 |
| 34.30 | 2.61 | 1.52 |
| 35.68 | 2.52 | 2.00 |
| 36.85 | 2.44 | 2.14 |

Stability Study of Form CS20

Figure 4E:
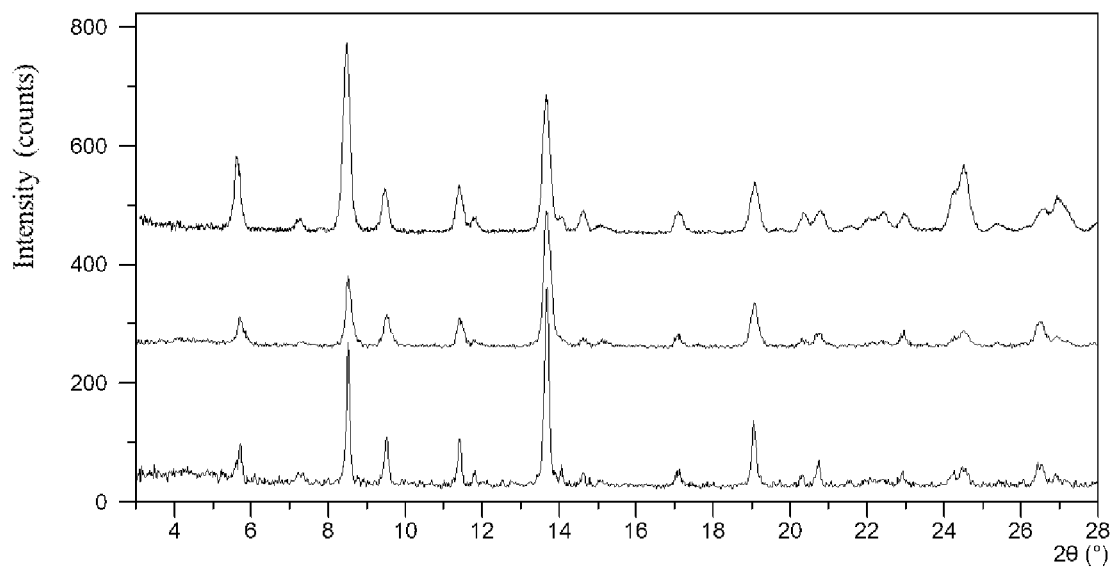
FIG. 4E shows an XRPD pattern overlay of Form CS20 before and after being stored under 25° C./60% RH and 40° C./75% RH for two weeks (from top to bottom: XRPD pattern before storage, XRPD pattern after being stored under 25° C./60% RH for two weeks, XRPD pattern after being stored under 40° C./75% RH for two weeks).

Two samples of apabetalone Form CS20 were placed in constant temperature and humidity chambers at 25° C./60% RH and 40° C./75% RH for 2 weeks in open dish. Crystalline form of the sample were tested by XRPD and impurity of the sample were checked. The XRPD pattern overlay is substantially as depicted in FIG. 4E (from top to bottom: XRPD pattern of Form CS20 before and after being stored under 25° C./60% RH and 40° C./75% RH for 2 weeks). No form change and obvious purity decrease was observed for Form CS20 after being stored at 25° C./60% RH and 40° C./75% RH for 2 weeks. It can be seen that Form CS20 has good stability.

Solubility Study of Form CS20

The prepared apabetalone Form CS20 was suspended into SGF (simulated gastric fluids) and FeSSIF (fed state simulated intestinal fluids, pH=5.0) to obtain saturated solutions. After being equilibrated for 1 h, 4 h and 24 h, concentrations of the saturated solutions were measured by HPLC. The results are listed in Table 4.3.

TABLE 4.3

| Time (h) | Solubility (mg/mL) | |
|---|---|---|
| | SGF | FeSSIF |
| 1 | 0.44 | 0.19 |
| 4 | 0.41 | 0.16 |
| 24 | 0.51 | 0.22 |

The above results show that Form CS20 of apabetalone of the present disclosure has good solubility in SGF and FeSSIF. Polymorph with high solubility is beneficial to increase the blood concentration of drugs in human body and improve the bioavailability of drugs, which is of great significance for drug research.

Example 5

Preparation of Form CS1 (Method 1)

The process of preparing Form CS1 of apabetalone comprises the following steps:

Dissolving step: About 10 mg of apabetalone solid was dissolve in corresponding solvent of Table 5.1, and a clear solution was obtained by filtering.

Precipitation step: The prepared solution was added to corresponding anti-solvent of Table 5.1 or corresponding anti-solvent was added to the prepared solution with stirring until a lot of precipitation was observed. The solid was collected by centrifugation and drying. The obtained solid was Form CS1 of apabetalone.

Furthermore, the reaction conditions, composition and amount of solvents and anti-solvents of the preparing process for said Form CS1 of apabetalone are listed in Table 5.1.

TABLE 5.1

| Sample No. | Weight (mg) | Solvent | Volume (mL) | Anti-solvent | Volume (mL) | Method |
|---|---|---|---|---|---|---|
| 5-a | 10.1 | Tetrahydrofuran | 2.125 | n-Heptane | 3.0 | Anti-solvent addition |
| 5-b | 10.1 | Tetrahydrofuran | 2.125 | n-Heptane | 3.0 | Reverse anti-solvent addition |
| 5-c | 10.1 | Tetrahydrofuran | 2.125 | Methyl tertiary butyl ether | 3.0 | Anti-solvent addition |
| 5-d | 10.1 | Tetrahydrofuran | 2.125 | Methyl tertiary butyl ether | 3.0 | Reverse anti-solvent addition |
| 5-e | 10.1 | Tetrahydrofuran | 2.125 | Toluene | 3.0 | Reverse anti-solvent addition |
| 5-f | 10.1 | Chloroform | 1.375 | Methyl tertiary butyl ether | 2.0 | Reverse anti-solvent addition |
| 5-g | 10.1 | Chloroform | 1.375 | Toluene | 3.0 | Anti-solvent addition |
| 5-h | 9.9 | Dimethyl sulfoxide | 1.0 | Water | 3.0 | Reverse anti-solvent addition |
| 5-i | 10.1 | Dimethylacetamide | 0.25 | Acetonitrile | 3.0 | Reverse anti-solvent addition |

Figure 5A:
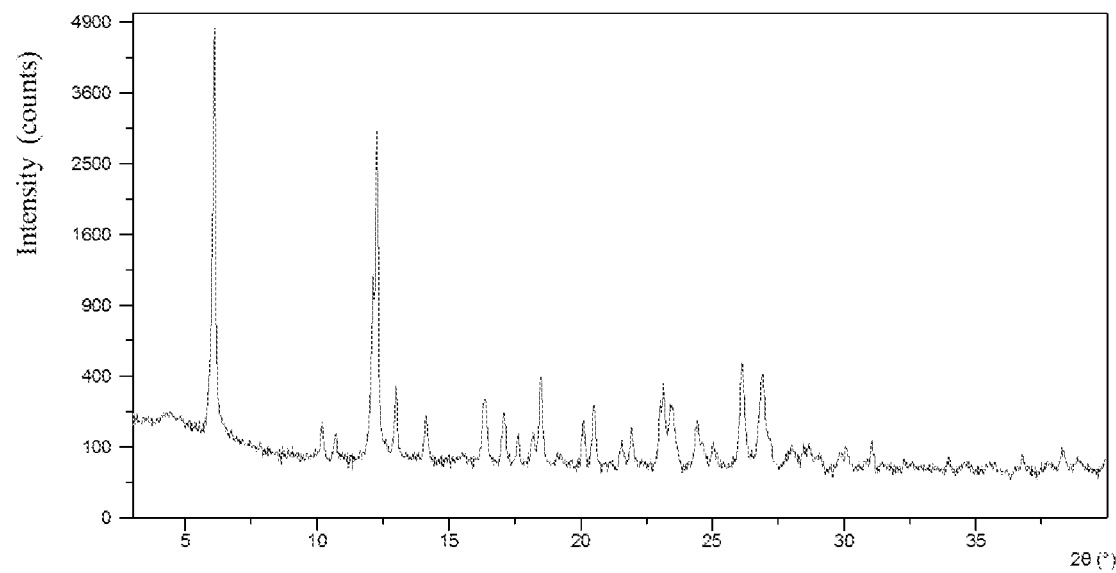
FIG. 5A shows an XRPD pattern of Form CS1 according to example 5 method 1 of the present disclosure.
Figure 5B:
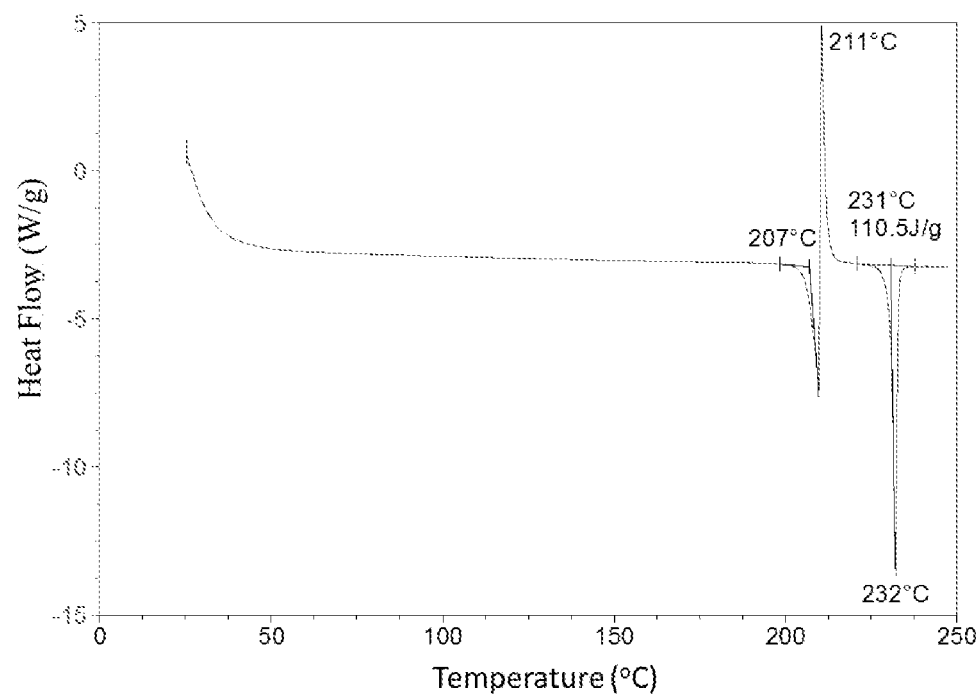
FIG. 5B shows a DSC curve of Form CS1 according to example 5 method 1 of the present disclosure.
Figure 5C:
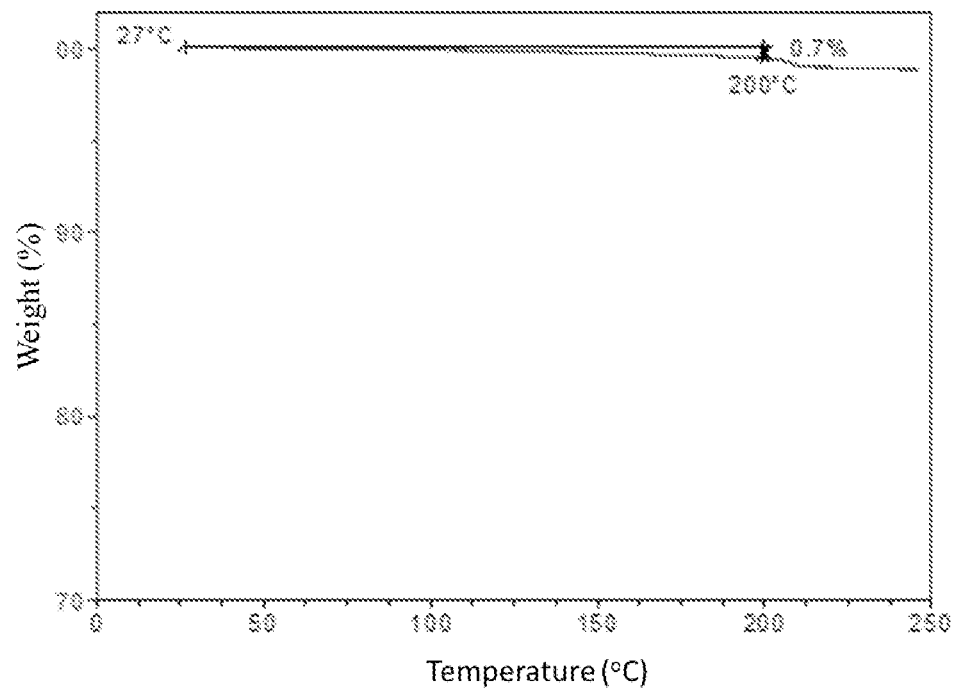
FIG. 5C shows a TGA curve of Form CS1 according to example 5 method 1 of the present disclosure.

Sample 5-a to 5-i were confirmed to be Form CS1 of apabetalone by XRPD. Sample 5-a was selected for characterization. The XRPD pattern is substantially as depicted in FIG. 5A, and the XRPD data are listed in Table 5.2. The DSC curve of Form CS1 is substantially as depicted in FIG. 5B, which shows the first endothermic peak at around 207° C., the first exothermic peak at around 211° C. and the second endothermic peak at around 231° C. The TGA curve of Form CS1 is substantially as depicted in FIG. 5C, which shows about 0.7% weight loss when heated to 200° C.

TABLE 5.2

| 2 Theta | d spacing | Intensity % |
|---|---|---|
| 4.38 | 20.19 | 1.10 |
| 6.11 | 14.47 | 100.00 |
| 10.19 | 8.68 | 2.41 |
| 10.70 | 8.27 | 1.40 |
| 12.11 | 7.31 | 21.04 |
| 12.27 | 7.21 | 62.62 |
| 12.99 | 6.82 | 5.91 |
| 14.12 | 6.27 | 3.01 |
| 16.37 | 5.41 | 4.60 |
| 17.09 | 5.19 | 3.31 |
| 17.63 | 5.03 | 1.77 |
| 18.18 | 4.88 | 1.63 |
| 18.48 | 4.80 | 7.06 |
| 20.12 | 4.41 | 2.93 |
| 20.49 | 4.33 | 4.18 |
| 21.55 | 4.12 | 1.12 |
| 21.93 | 4.05 | 2.34 |
| 23.16 | 3.84 | 5.71 |
| 23.45 | 3.79 | 4.16 |
| 24.45 | 3.64 | 2.64 |
| 25.02 | 3.56 | 1.26 |
| 26.11 | 3.41 | 8.67 |
| 26.84 | 3.32 | 7.12 |
| 28.00 | 3.19 | 0.96 |
| 28.60 | 3.12 | 0.96 |
| 30.04 | 2.98 | 0.86 |
| 31.04 | 2.88 | 1.25 |

TABLE 5.2-continued

| 2 Theta | d spacing | Intensity % |
|---|---|---|
| 35.60 | 2.52 | 0.25 |
| 36.80 | 2.44 | 0.50 |
| 38.30 | 2.35 | 0.89 |

Preparation of Form CS1 (Method 2)

The process of preparing Form CS1 comprises the following steps:

Dissolving step: Apabetalone solid was dissolved in corresponding solvent of Table 5.3 at 50° C. to obtain a clear solution.

Precipitation step: The solution was cooled to −20-5° C. rapidly or slowly until solid precipitated. The solid was collected by centrifugation and drying. The obtained solid was Form CS1 of apabetalone.

Figure 5D:
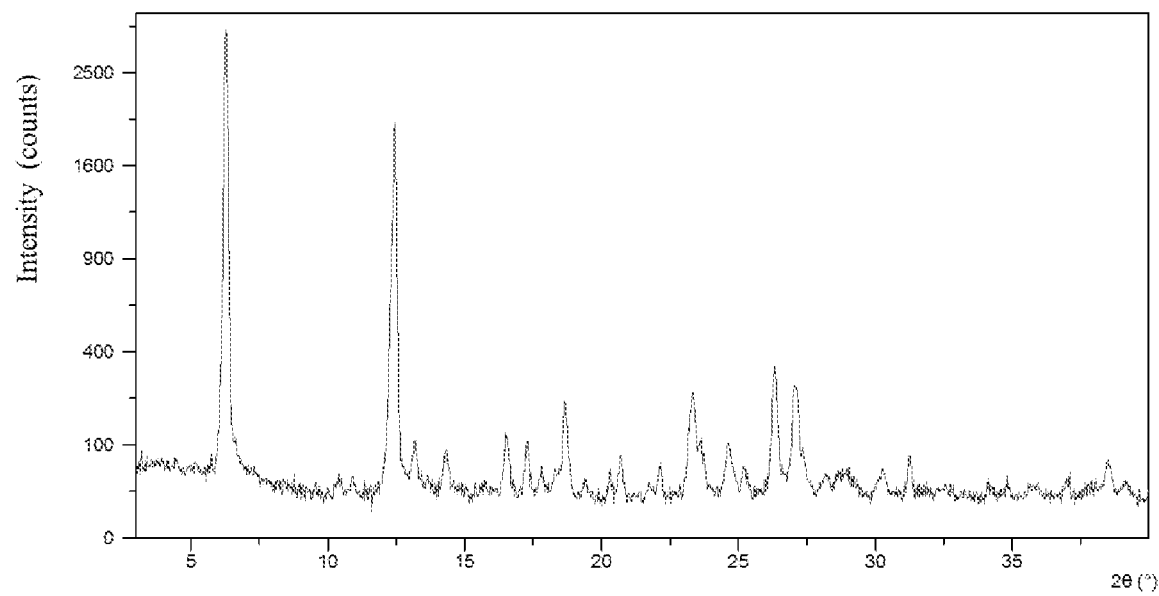
FIG. 5D shows an XRPD pattern of Form CS1 according to example 5 method 2 of the present disclosure.

Said reaction conditions, solvent composition and solvent amount of the preparation method of apabetalone Form CS1 are shown in Table 5.3. Sample 5-j to 5-n were confirmed to be Form CS1 of apabetalone by XRPD. The XRPD pattern of sample 5-j is substantially as depicted in FIG. 5D, and the XRPD data are listed in Table 5.4.

TABLE 5.3

| Sample No. | Weight (mg) | Solvent (v/v) | Volume (mL) | Method | T (° C.) |
|---|---|---|---|---|---|
| 5-j | 19.9 | Tetrahydrofuran | 1.0 | Slow cooling | 5 |
| 5-k | 19.9 | Tetrahydrofuran | 1.0 | Rapid cooling | −20 |
| 5-l | 10.8 | Acetone | 3.0 | Rapid cooling | −20 |
| 5-m | 10.2 | Ethyl acetate/acetone (1:1) | 3.0 | Rapid cooling | −20 |
| 5-n | 10.7 | Acetonitrile/N,N-dimethylformamide (9:1) | 3.0 | Rapid cooling | −20 |

TABLE 5.4

| 2 Theta | d spacing | Intensity % |
|---|---|---|
| 3.57 | 24.78 | 1.09 |
| 6.10 | 14.48 | 100.00 |
| 10.26 | 8.62 | 0.50 |
| 12.28 | 7.21 | 65.97 |
| 13.01 | 6.81 | 2.85 |
| 14.15 | 6.26 | 2.43 |
| 16.36 | 5.42 | 3.05 |
| 17.13 | 5.18 | 2.82 |
| 18.47 | 4.80 | 6.67 |
| 19.24 | 4.61 | 0.64 |
| 20.14 | 4.41 | 0.92 |
| 20.51 | 4.33 | 1.86 |
| 22.01 | 4.04 | 1.19 |
| 23.16 | 3.84 | 7.43 |
| 24.45 | 3.64 | 2.81 |
| 25.01 | 3.56 | 1.21 |
| 26.15 | 3.41 | 10.57 |
| 26.86 | 3.32 | 8.29 |
| 28.76 | 3.10 | 0.82 |
| 30.08 | 2.97 | 0.92 |
| 31.07 | 2.88 | 1.86 |
| 34.62 | 2.59 | 0.49 |
| 36.83 | 2.44 | 0.62 |
| 38.30 | 2.35 | 1.75 |

Long-Term Stability Study of Form CS1

Figure 5E:
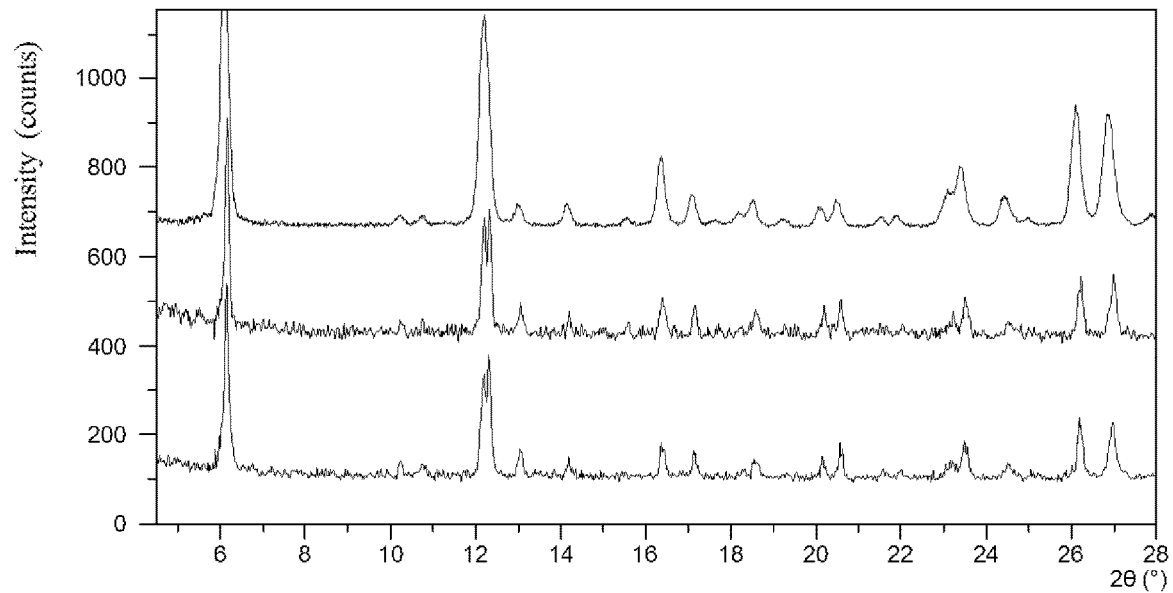
FIG. 5E shows an XRPD pattern overlay of Form CS1 before and after being stored under 25° C./60% RH and 40° C./75% RH for 10 months (from top to bottom: XRPD pattern before storage, XRPD pattern after being stored under 25° C./60% RH for 10 months, XRPD pattern after being stored under 40° C./75% RH for 10 months).

Two samples of apabetalone Form CS1 were placed in constant temperature and humidity chambers at 25° C./60% RH and 40° C./75% RH for 10 months in open dishes. The samples were characterized by XRPD and chemical impurity. The results are substantially as depicted in FIG. 5E (from top to bottom: XRPD pattern of Form CS1 before and after being stored under 25° C./60% RH and 40° C./75% RH for 10 months) and Table 5.5.

No form change and obvious purity decrease was observed for Form CS1 after being stored at 25° C./60% RH and 40° C./75% RH for 10 months. It can be seen that Form CS1 has good stability and high purity.

TABLE 5.5

| Condition | 1 week | 2 weeks | 5 weeks | 10 months |
|---|---|---|---|---|
| 25° C./60% RH | 99.27 | 99.23 | 99.25 | 99.24 |
| 40° C./75% RH | 99.20 | 99.20 | 99.25 | 99.21 |

Solubility Study of Form CS1

The prepared solid of apabetalone Form CS1 was suspended into SGF (simulated gastric fluids) and FeSSIF (fed state simulated intestinal fluids, pH=5.0) to obtain saturated solutions. After being equilibrated for 1 h, 4 h and 24 h, concentrations of the saturated solutions were measured by HPLC. The results are listed in Table 5.6.

TABLE 5.6

| Time (h) | Solubility (mg/mL) | |
|---|---|---|
| | SGF | FeSSIF |
| 1 | 0.31 | 0.14 |
| 4 | 0.29 | 0.11 |
| 24 | 0.33 | 0.14 |

The above results show that Form CS1 of apabetalone has good solubility in SGF and FeSSIF.

Hygroscopicity Study of Form CS1

Figure 5F:
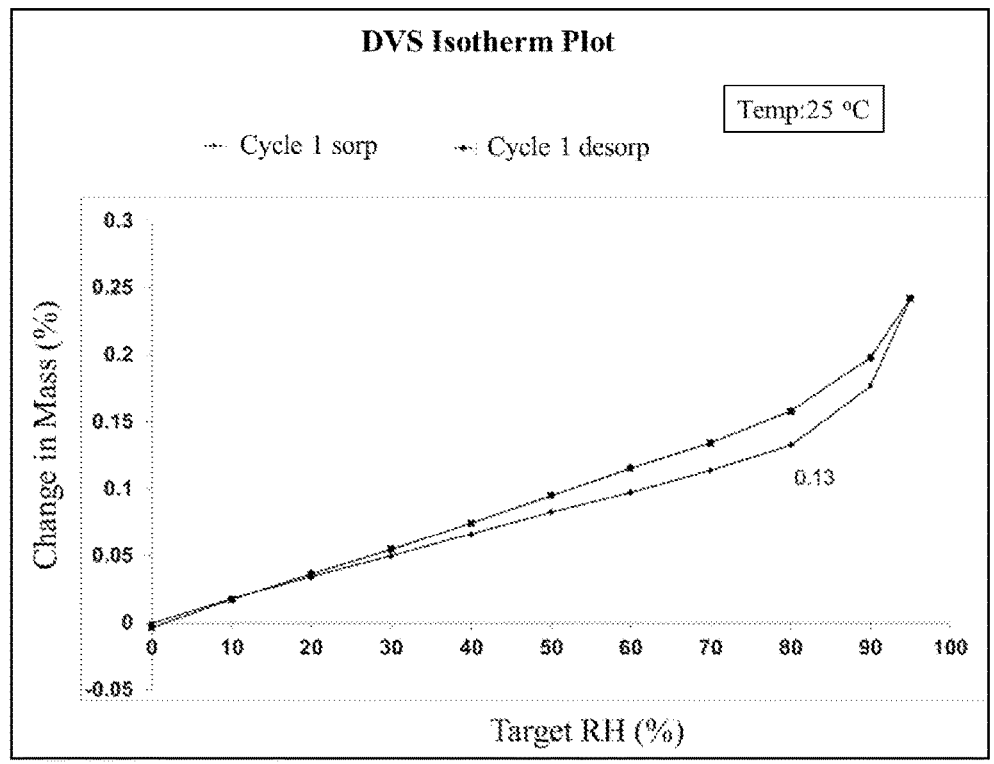
FIG. 5F shows a DVS plot of Form CS1 according to example 5 of the present disclosure.

Dynamic vapor sorption (DVS) was applied to test hygroscopicity of Form CS1 of the present disclosure with about 10 mg of sample. The result is listed in Table 5.7. The DVS plot of Form CS1 is substantially as depicted in FIG. 5F.

TABLE 5.7

| Form | Weight Gain under 80% Relative Humidity |
|---|---|
| Form CS1 | 0.13% |

Figure 5G:
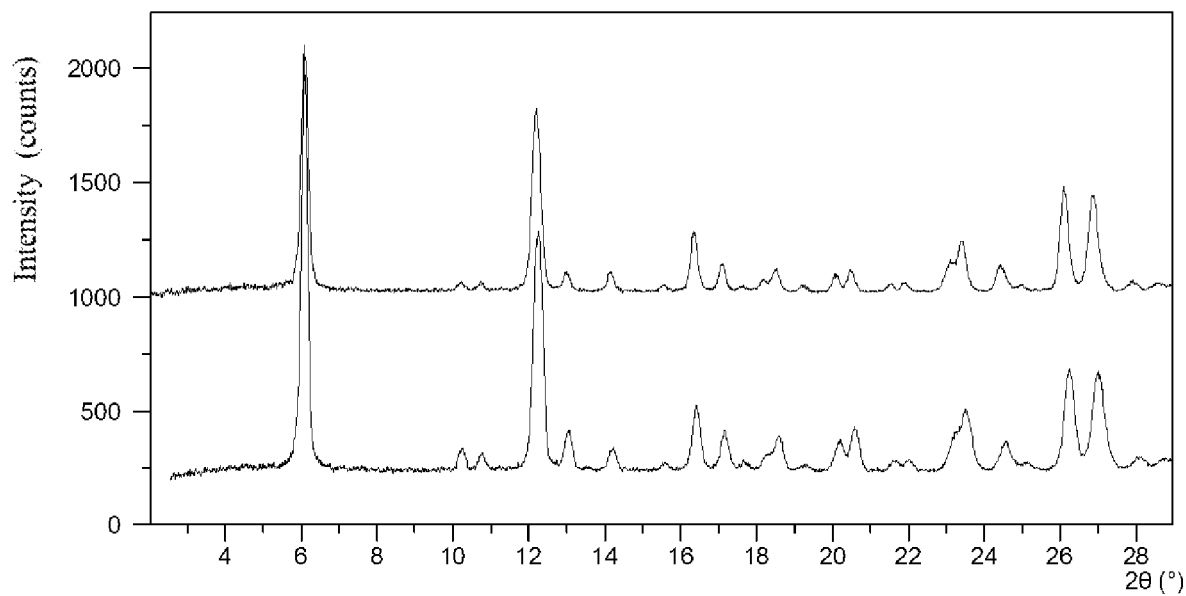
FIG. 5G shows an XRPD pattern overlay of Form CS1 according to example 5 of the present disclosure before and after DVS test.

The results showed that weight gain of Form CS1 under 80% RH is 0.13%. According to the hygroscopicity criteria, Form CS1 is almost non hygroscopic. The XRPD pattern of Form CS1 after DVS test is shown in FIG. 5G. No form change was observed for Form CS1 before and after DVS test, which indicates that Form CS1 is stable under the influence of humidity.

Form CS1 of the present disclosure shows low hygroscopicity and can avoid the problems such as crystal instability in the process of drug preparation and/or storage, as well as the unprocessability of the preparation caused by external factors such as environmental moisture, which is conducive to the accurate quantitative preparation and later transportation and storage.

Mechanical Stability of Form CS1

Figure 5H:
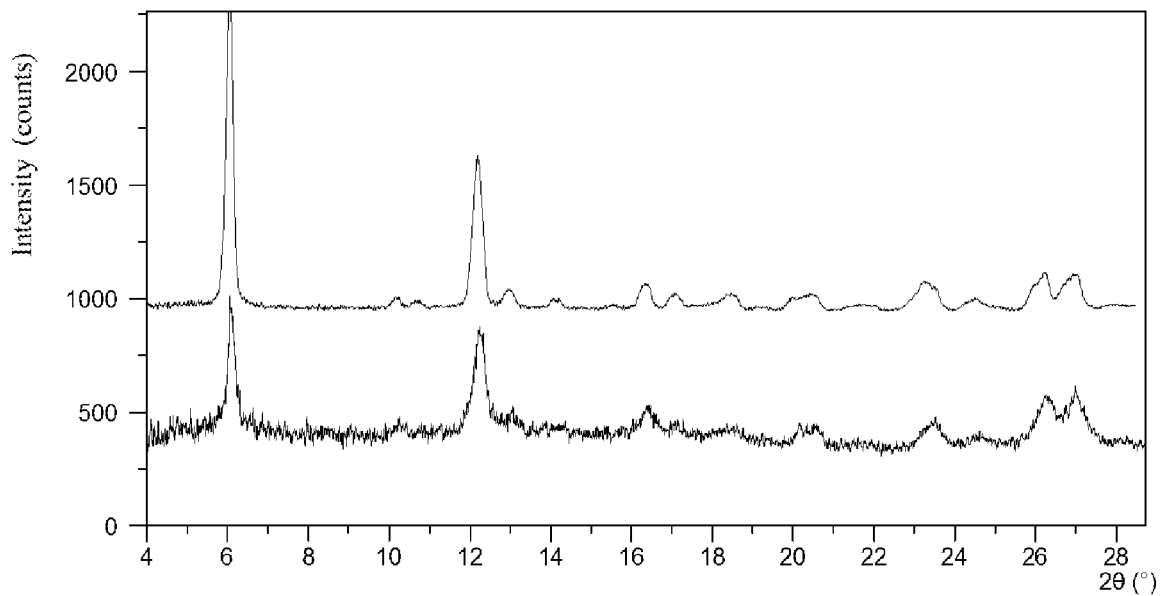
FIG. 5H shows an XRPD pattern overlay of Form CS1 according to example 5 of the present disclosure before and after grinding.

Certain amount of Form CS1 was placed in a mortar and ground manually for 5 minutes. XRPD of the solid obtained was tested. The results are shown in FIG. 5H.

The results showed that no form change and obvious crystallity decrease was observed for Form CS1 of apabetalone under certain mechanical stress, and it can still maintain stable physical and chemical properties, which is suitable for drug preparation and storage. Grinding of API is usually needed in the process of formulation, and good grinding stability will reduce the risk of crystallinity decrease and transformation of solid form of API.

Formulation Study of Form CS1

Certain amount of the API, microcrystalline cellulose, croscarmellose sodium according to Table 5.8 and 2 mg of magnesium stearate were weighted and blended for 2 minutes. Flakes were prepared using a manual tablet press at 5 KN pressure with a φ20 mm round tooling. The crushed flakes were manually sieved through 20 mesh sieve. 2 mg of magnesium stearate was added, and then the obtained powder was blended for 1 minute. The mixture was encapsulated into a 1# capsule shell, then the capsule was packed in 35 cc HDPE (high density polyethylene) bottle (one capsule per bottle) containing 1 g of desiccant. The bottle was then sealed by sealing machine. The composition of the formulation (per 200 mg) is shown in table 5.8 below. Form CS1 is stable in the preparations after testing.

TABLE 5.8

| Component | Quantity (mg/capsule) |
| --- | --- |
| API | 50 |
| Microcrystalline cellulose | 136 |
| Croscarmellose sodium | 10 |
| Magnesium stearate | 4 |

Dissolution test was performed on the obtained capsule. The conditions are as follows:
Medium: HCl (0.1 mol/L)
Method: Paddle
Volume: 900 mL
Speed: 75 rpm
Temperature: 37° C.

Figure 5I:
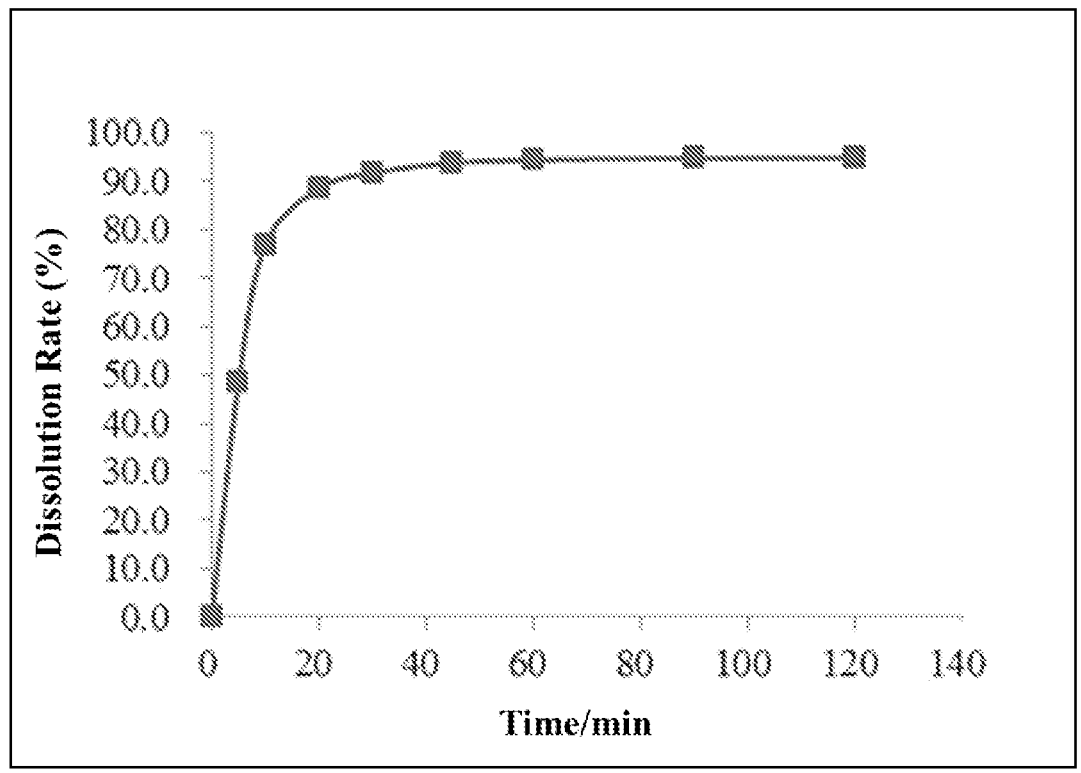
FIG. 5I shows a dissolution rate profile of Form CS1 according to example 5 of the present disclosure in formulations.

Dissolution results of Form CS1 are presented in FIG. 5I, which indicates that Form CS1 possesses favorable dissolution. The released amount can reach more than 90% at 20 minutes. In drug product development, rapid dissolution rate can speed up the dissolution of the drug in body. By adjusting the excipients, it is possible to control the rapid action of drugs in specific parts and get a short onset of action of the drugs.

Example 6

Preparation of Form CS7

The process of preparing Form CS7 of apabetalone comprises the following steps:

Dissolving step: 5.3 mg of apabetalone solid was dissolved in 1 mL of chloroform, and a clear solution was obtained by filtering.

Figure 6A:
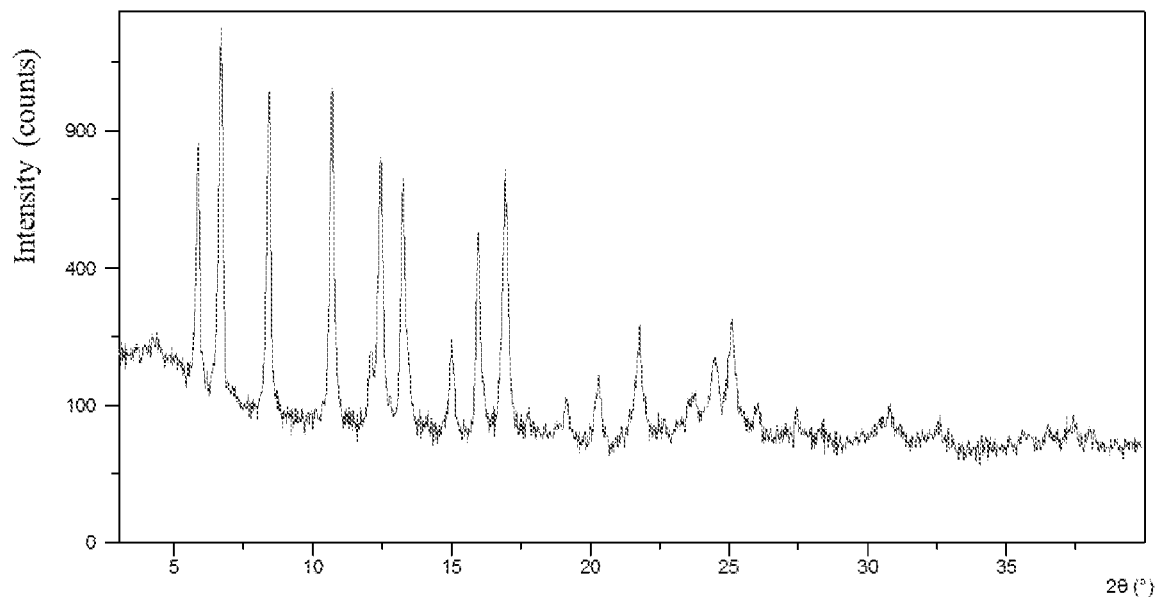
FIG. 6A shows an XRPD pattern of Form CS7 according to example 6 of the present disclosure.

Precipitation step: The solution was added to a 3-mL glass vial. The vial was put into a 20-mL glass vial containing 5 mL of methyl isobutyl ketone for liquid vapor diffusion. Then the 20-mL vial was sealed and left at room temperature until solid precipitated. The solid was collected by centrifugation and drying to obtain Form CS7 of apabetalone. The XRPD pattern of Form CS7 is substantially as depicted in FIG. 6A, and the XRPD data are listed in Table 6.1.

Figure 6B:
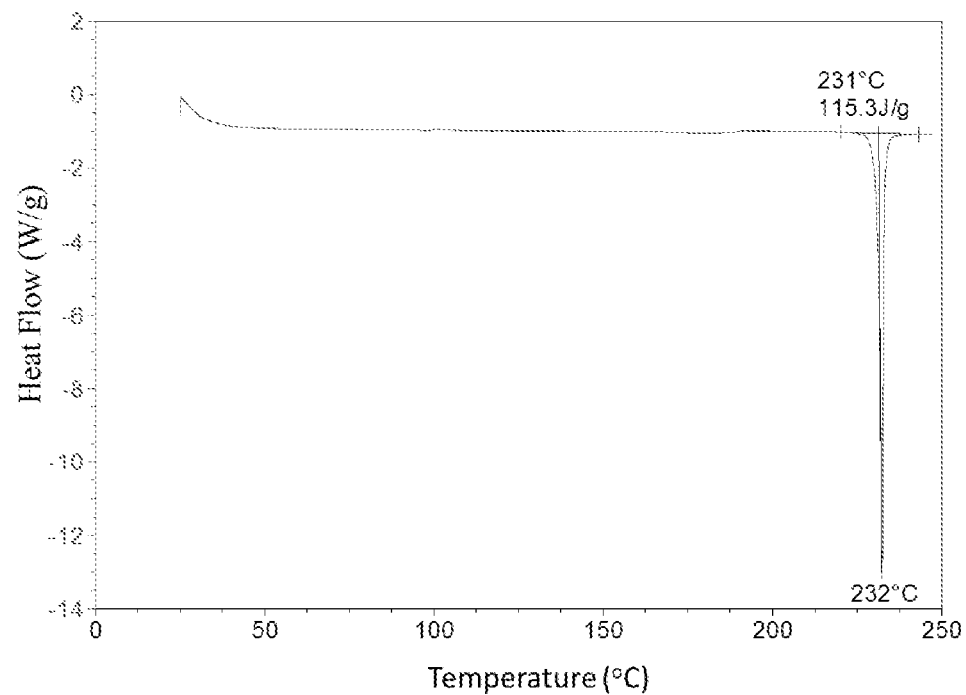
FIG. 6B shows a DSC curve of Form CS7 according to example 6 of the present disclosure.
Figure 6C:
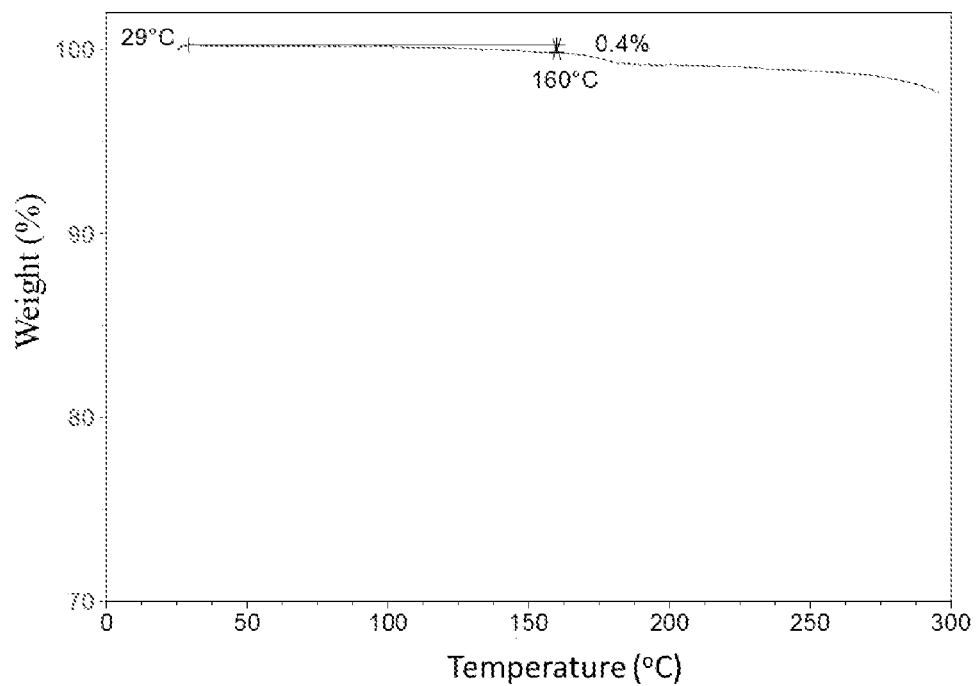
FIG. 6C shows a TGA curve of Form CS7 according to example 6 of the present disclosure

The DSC curve shows the first endothermic peak at around 231° C., which is substantially as depicted in FIG. 6B. The TGA curve shows about 0.4% weight loss when heated to 160° C., which is substantially as depicted in FIG. 6C.

TABLE 6.1

| 2 Theta | d spacing | Intensity % |
| --- | --- | --- |
| 4.27 | 20.68 | 3.98 |
| 5.87 | 15.06 | 55.68 |
| 6.69 | 13.21 | 100 |
| 8.43 | 10.50 | 77.7 |
| 10.70 | 8.27 | 80.13 |
| 12.08 | 7.32 | 9.24 |
| 12.46 | 7.10 | 53.68 |
| 13.25 | 6.68 | 49.94 |
| 14.99 | 5.91 | 9.73 |
| 15.96 | 5.55 | 34.89 |
| 16.94 | 5.23 | 53.34 |
| 19.16 | 4.63 | 3.48 |
| 20.32 | 4.37 | 6.07 |
| 21.76 | 4.08 | 15.6 |
| 23.67 | 3.76 | 4.6 |
| 24.47 | 3.64 | 9.66 |
| 25.09 | 3.55 | 15.93 |
| 26.01 | 3.43 | 3.31 |
| 27.42 | 3.25 | 2.99 |
| 30.79 | 2.90 | 3.25 |
| 32.57 | 2.75 | 1.7 |
| 36.50 | 2.46 | 1.75 |
| 37.45 | 2.40 | 1.96 |

Stability Study of Form CS7

Figure 6D:
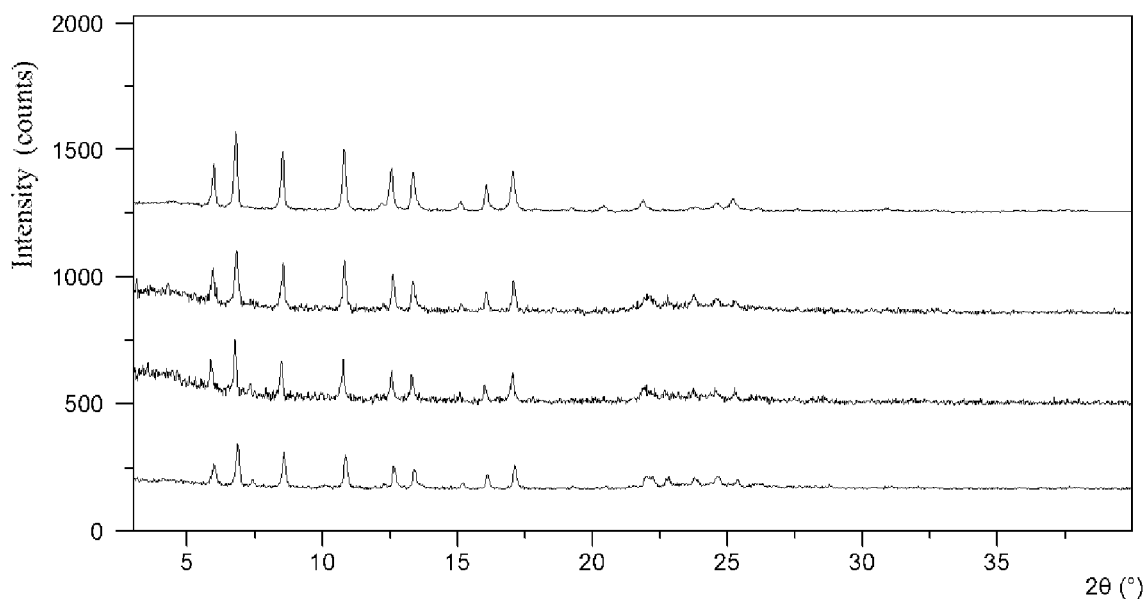
FIG. 6D shows an XRPD pattern overlay of Form CS7 before and after being stored under 25° C./60% RH and 40° C./75% RH for 4 weeks and 80° C. for one day (from top to bottom: XRPD pattern before storage, XRPD pattern after being stored under 25° C./60% RH for 4 weeks, XRPD pattern after being stored under 40° C./75% RH for 4 weeks, XRPD pattern after being stored under 80° C. for one day).

Three samples of apabetalone Form CS7 were placed in constant temperature and humidity chambers at 25° C./60% RH and 40° C./75% RH for 4 weeks and 80° C. for 1 day in open dishes. Crystalline form of the sample were tested by XRPD and impurity of the sample were checked. The XRPD pattern overlay is substantially as depicted in FIG. 6D (from top to bottom: XRPD pattern of Form CS7 before and after being stored under 25° C./60% RH and 40° C./75% RH for 4 weeks and 80° C. for 1 day).

No form change and obvious purity decrease was observed for Form CS7 after being stored at 25° C./60% RH and 40° C./75% RH for 4 weeks and 80° C. for 1 day. It can be seen that Form CS7 has good stability.

Solubility Study of Form CS7

The prepared solid of apabetalone Form CS7 was suspended into SGF (simulated gastric fluids) and FeSSIF (fed state simulated intestinal fluids, pH=5.0) to obtain saturated solutions. After being equilibrated for 1 h, 4 h and 24 h, concentrations of the saturated solutions were measured by HPLC. The results are listed in Table 6.2.

TABLE 6.2

| Time | Solubility (mg/mL) | |
| --- | --- | --- |
| (h) | SGF | FeSSIF |
| 1 | 0.38 | 0.19 |
| 4 | 0.42 | 0.17 |
| 24 | 0.58 | 0.29 |

The above results show that Form CS7 of apabetalone has good solubility in SGF and FeSSIF. Polymorph with high solubility is beneficial to increase the blood concentration of drugs in human body and improve the bioavailability of drugs, which is of great significance for drug research.

Hygroscopicity Study of Form CS7

Dynamic vapor sorption (DVS) was applied to test hygroscopicity of Form CS7 of the present disclosure with about 10 mg of samples. The result is listed in Table 6.3.

TABLE 6.3

| Form | Weight gain under 80% relative humidity |
|---|---|
| Form CS7 | 0.79% |

Figure 6E:
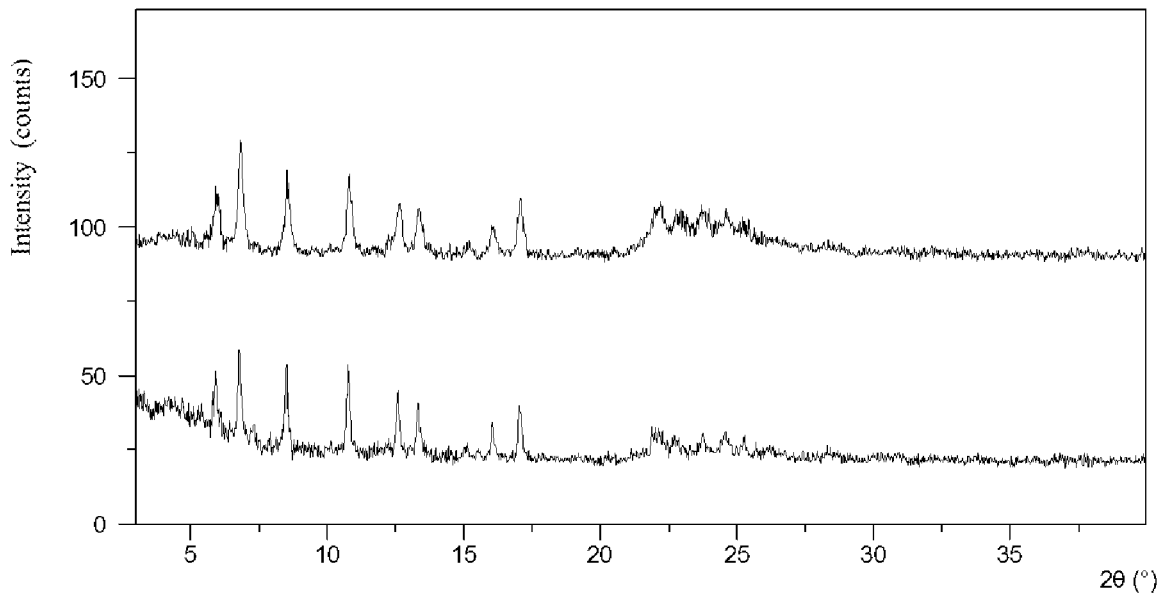
FIG. 6E shows an XRPD pattern overlay of Form CS7 according to example 6 of the present disclosure before and after DVS test.

The results showed that weight gain of Form CS7 under 80% RH is 0.79%. According to the hygroscopicity criteria, Form CS7 is slightly hygroscopic. The XRPD pattern of Form CS7 after DVS test was shown in FIG. 6E. No form change was observed for Form CS7 before and after DVS test, which indicates that Form CS7 has good humidity stability.

Form CS7 of the disclosure shows low hygroscopicity, which can well avoid the problems such as crystal instability in the process of drug preparation and/or storage, as well as the unprocessability of the preparation caused by external factors such as environmental moisture, which is conducive to the accurate quantitative preparation and later transportation and storage.

Example 7

Preparation of Form CS9

The process of preparing Form CS9 comprises the following steps:

Dissolving step: About 10 mg of apabetalone solid was dissolved in corresponding solvent of Table 7.1, and a clear solution was obtained by filtering.

Precipitation step: The prepared solution was left at room temperature for slow evaporation until solid precipitated. The obtained solid was Form CS9 of Apabetalone.

Said reaction conditions, solvent composition and solvent amount of the preparation method of apabetalone Form CS9 are shown in Table 7.1. The samples 7-a to 7-c were confirmed to be Form CS9 by XRPD.

TABLE 7.1

| Sample No. | Weight (mg) | Solvent (v/v) | Volume (mL) | Whether to add polymer or not (Y/N) | T (° C.) |
|---|---|---|---|---|---|
| 7-a | 10.0 | Tetrahydrofuran/isopropanol (1:1) | 2.7 | N | 25 |
| 7-b | 10.0 | Dichloromethane/isopropanol (4:1) | 1.7 | N | 25 |
| 7-c | 10.7 | Chloroform/acetonitrile (2:1) | 1.7 | Y | 25 |

Figure 7A:
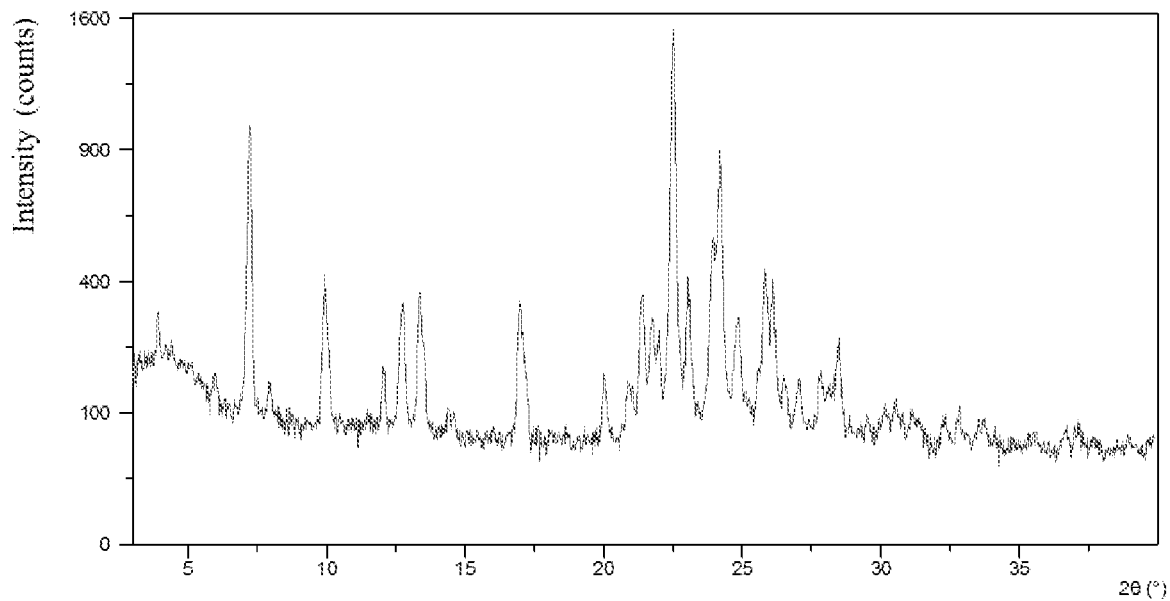
FIG. 7A shows an XRPD pattern of Form CS9 according to example 7 of the present disclosure.
Figure 7B:
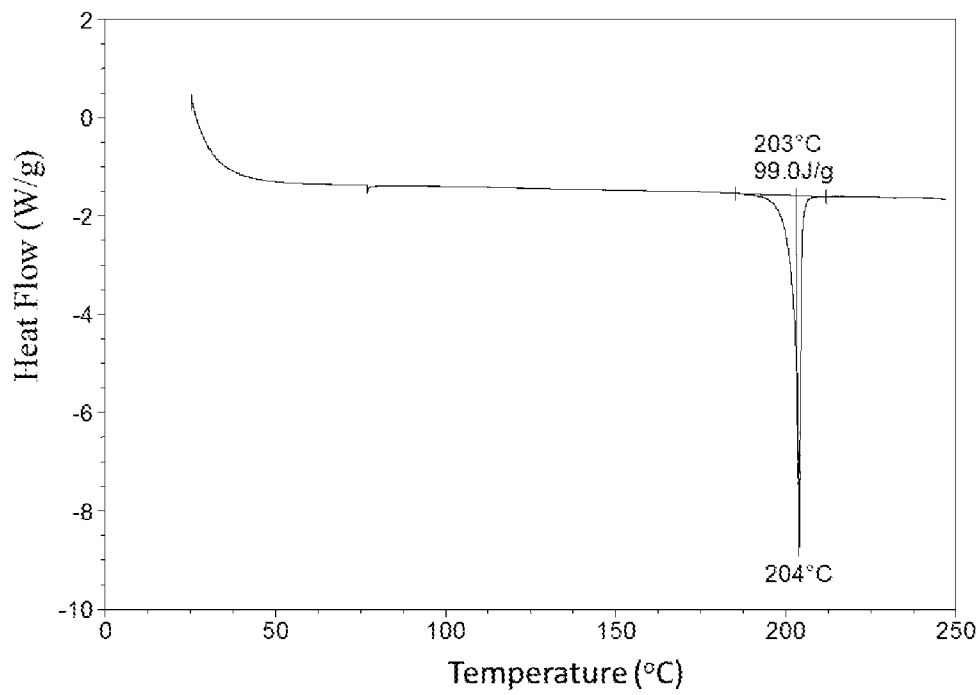
FIG. 7B shows a DSC curve of Form CS9 according to example 7 of the present disclosure.
Figure 7C:
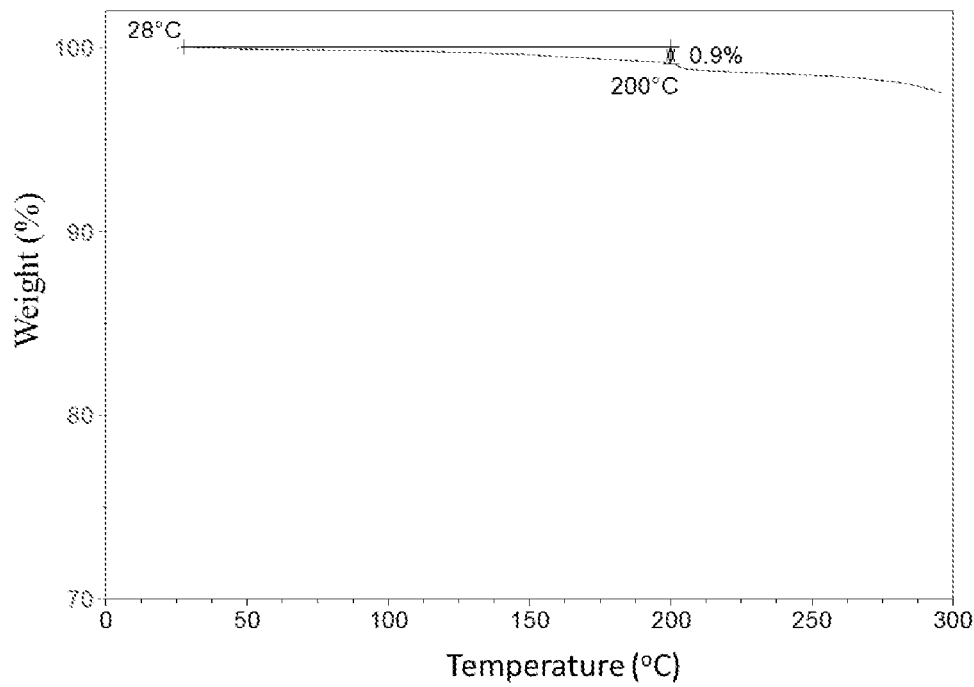
FIG. 7C shows a TGA curve of Form CS9 according to example 7 of the present disclosure.

Sample 7-b was selected for characterization. The XRPD pattern is substantially as depicted in FIG. 7A, and the XRPD data are listed in Table 7.2. The DSC curve is substantially as depicted in FIG. 7B, which shows the first endothermic peak at around 203° C. The TGA curve is substantially as depicted in FIG. 7C, which shows about 0.9% weight loss when heated to 200° C.

TABLE 7.2

| 2 Theta | d spcaing | Intensity % |
|---|---|---|
| 3.92 | 22.55 | 17.55 |
| 5.99 | 14.75 | 7.28 |
| 7.25 | 12.19 | 64.22 |
| 7.94 | 11.13 | 6.24 |
| 9.92 | 8.91 | 24.30 |
| 12.09 | 7.32 | 8.02 |
| 12.78 | 6.93 | 17.69 |
| 13.36 | 6.63 | 22.02 |
| 13.53 | 6.54 | 10.74 |
| 14.48 | 6.12 | 2.15 |
| 16.98 | 5.22 | 19.92 |
| 20.01 | 4.44 | 7.41 |
| 20.88 | 4.26 | 5.94 |
| 21.42 | 4.15 | 21.02 |
| 21.77 | 4.08 | 16.45 |
| 22.00 | 4.04 | 14.36 |
| 22.53 | 3.95 | 100.00 |
| 23.02 | 3.86 | 25.09 |
| 23.95 | 3.72 | 34.15 |
| 24.19 | 3.68 | 58.53 |
| 24.86 | 3.58 | 16.90 |
| 25.83 | 3.45 | 25.83 |
| 26.11 | 3.41 | 24.07 |
| 26.53 | 3.36 | 7.10 |
| 27.03 | 3.30 | 6.89 |
| 27.81 | 3.21 | 7.53 |
| 28.51 | 3.13 | 10.88 |
| 30.61 | 2.92 | 3.05 |
| 31.17 | 2.87 | 2.73 |
| 32.29 | 2.77 | 2.32 |
| 32.80 | 2.73 | 2.65 |
| 33.67 | 2.66 | 2.03 |
| 36.63 | 2.45 | 1.42 |
| 37.12 | 2.42 | 1.68 |

Stability Study of Form CS9

Figure 7D:
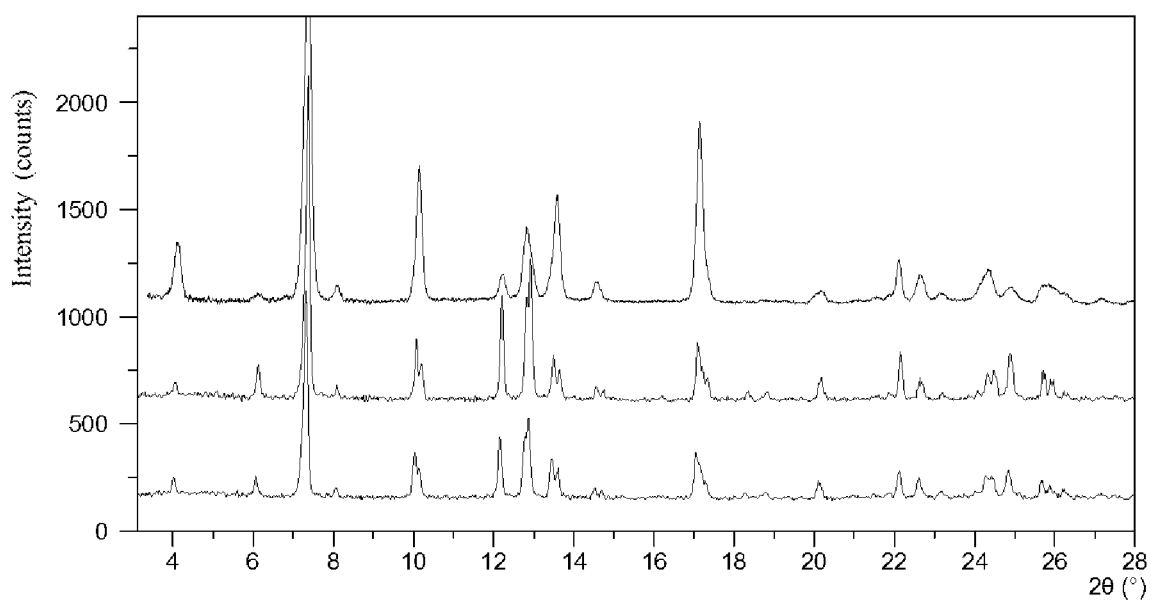
FIG. 7D shows an XRPD pattern overlay of Form CS9 before and after being stored under 25° C./60% RH and 40° C./75% RH for 10 months (from top to bottom: XRPD pattern before storage, XRPD pattern after being stored under 25° C./60% RH for 10 months, XRPD pattern after being stored under 40° C./75% RH for 10 months).

Two samples of apabetalone Form CS9 were placed in constant temperature and humidity chambers at 25° C./60% RH and 40° C./75% RH for 10 months in open dishes. Crystalline form of the sample were tested by XRPD and impurity of the sample were tested to check the stability of Form CS9. The XRPD pattern overlay pattern is substantially as depicted in FIG. 7D (from top to bottom: XRPD pattern of Form CS9 before and after being stored under 25° C./60% RH and 40° C./75% RH for 10 months).

No form change and obvious purity decrease was observed for Form CS9 after being stored at 25° C./60% RH and 40° C./75% RH for 10 months. It can be seen that Form CS9 has good stability.

Solubility Study of Form CS9

The prepared solid of apabetalone Form CS9 was suspended into SGF (simulated gastric fluids) and FeSSIF (fed state simulated intestinal fluids, pH=5.0) to obtain saturated solutions. After being equilibrated for 1 h, 4 h and 24 h, concentrations of the saturated solutions were measured by HPLC. The results are listed in Table 7.3.

TABLE 7.3

| Time (h) | Solubility (mg/mL) | |
|---|---|---|
| | SGF | FeSSIF |
| 1 | 0.30 | 0.17 |
| 4 | 0.31 | 0.13 |
| 24 | 0.37 | 0.20 |

The above results show that Form CS9 of apabetalone has good solubility in SGF and FeSSIF.

Hygroscopicity Study of Form CS9

Figure 7E:
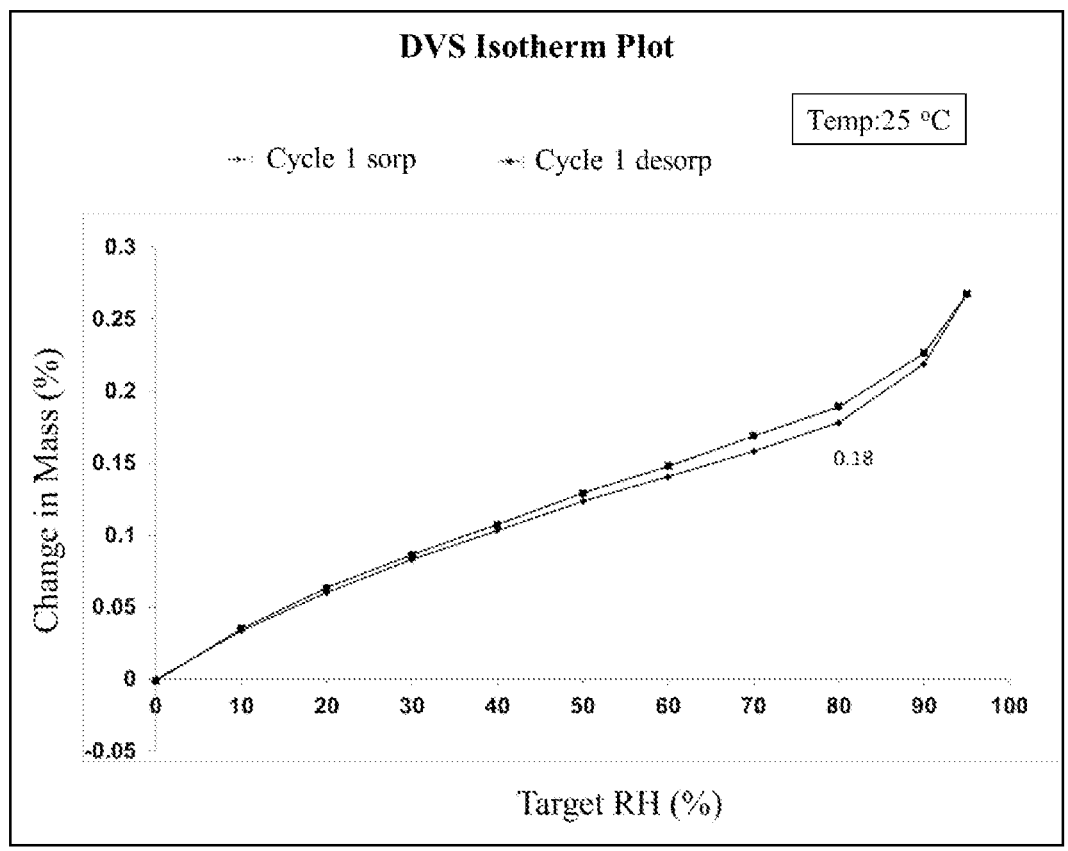
FIG. 7E shows a DVS plot of Form CS9 according to example 7 of the present disclosure.
Figure 7F:
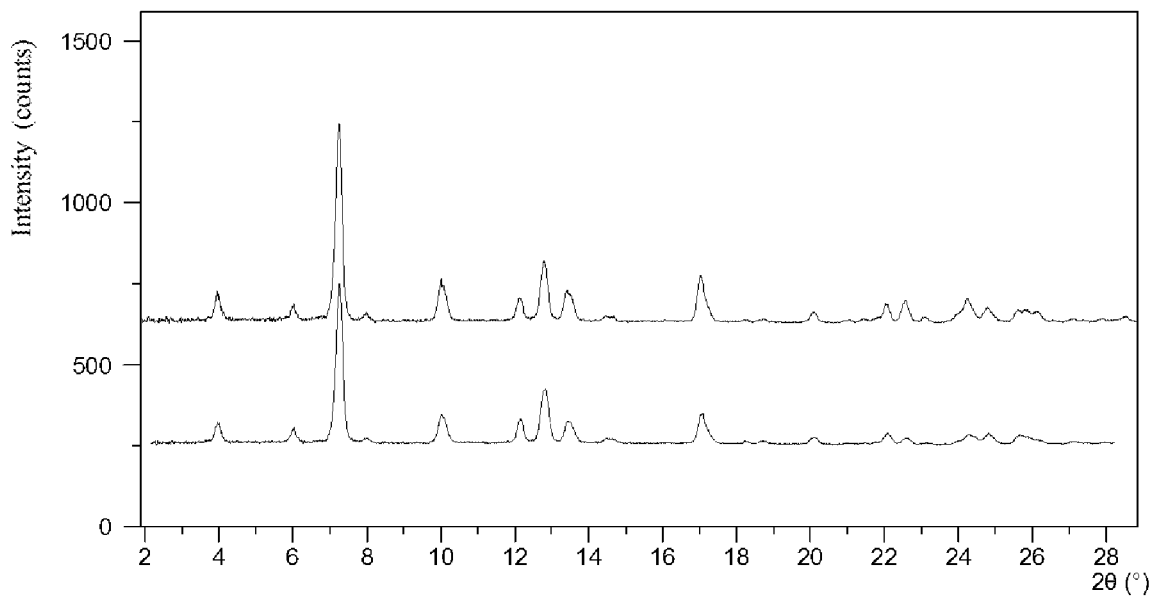
FIG. 7F shows an XRPD pattern overlay of Form CS9 according to example 7 of the present disclosure before and after DVS test

Dynamic vapor sorption (DVS) was applied to test hygroscopicity of Form CS9 of the present disclosure with about 10 mg of sample. The result is listed in Table 7.4. The DVS plot of Form CS9 is substantially as depicted in FIG. 7E. The XRPD pattern of Form CS9 after DVS test was shown in FIG. 7F. No form change was observed for Form CS9 before and after DVS test, which indicates that Form CS9 is stable under the influence of humidity.

TABLE 7.4

| Form | Weight gain under 80% relative humidity |
|---|---|
| Form CS9 | 0.18% |

The results showed that weight gain of Form CS9 under 80% RH is 0.18%. According to the hygroscopicity criteria, Form CS9 is almost non hygroscopic. Form CS9 of the present disclosure shows low hygroscopicity, which can well avoid the problems such as crystal instability in the process of drug preparation and/or storage, as well as the unprocessability of the preparation caused by external factors such as environmental moisture, which is conducive to the accurate quantitative preparation and later transportation and storage.

Example 8

Preparation of Form CS11 (Method 1)
The process of preparing Form CS11 comprises the following steps:
Dissolving step: about 10 mg of apabetalone solid was dissolved in 1.7 mL of methanol, and filtered to get a clear solution.
Precipitation step: The prepared solution was added to 3 mL of water or 3 mL of water was added to the prepared solution with stirring to obtain solid. Form CS11 was obtained by centrifugation and drying.
Said reaction conditions and amount of methanol and water of the preparation method of apabetalone Form CS11 are shown in Table 8.1. The samples 8-a to 8-b were confirmed to be Form CS11 by XRPD.

TABLE 8.1

| Sample No. | Weight (mg) | Volume of methanol (mL) | Volume of water (mL) | Method |
|---|---|---|---|---|
| 8-a | 10.0 | 1.7 | 3 | Antisolvent addition |
| 8-b | 10.0 | 1.7 | 3 | Reverse anti-solvent addition |

Figure 8A:
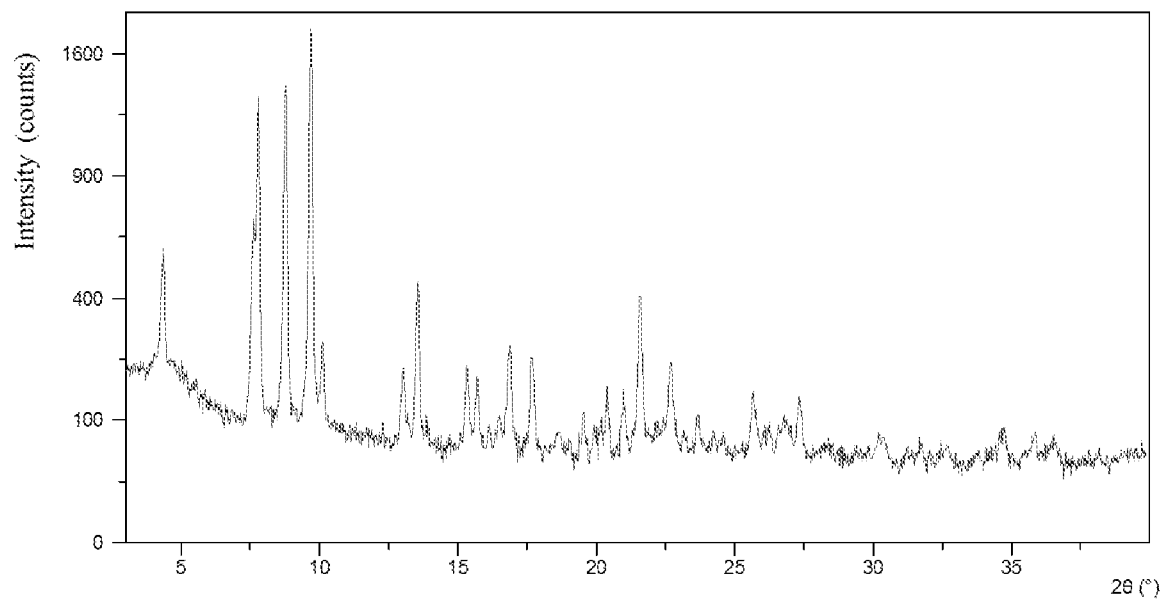
FIG. 8A shows an XRPD pattern of Form CS11 according to example 8 method 1 of the present disclosure
Figure 8B:
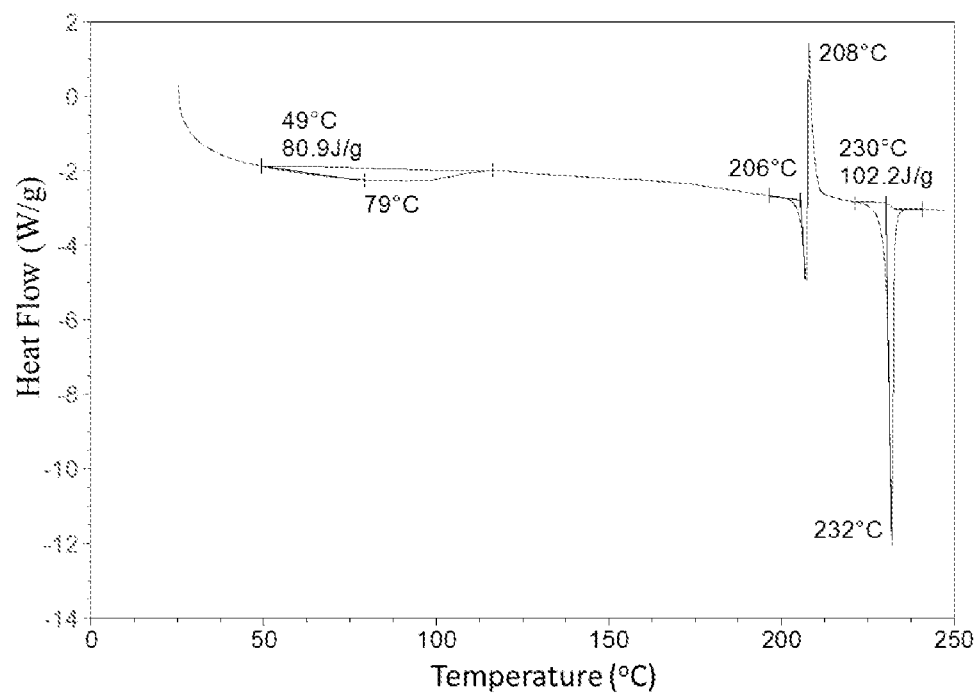
FIG. 8B shows a DSC curve of Form CS11 according to example 8 method 1 of the present disclosure
Figure 8C:
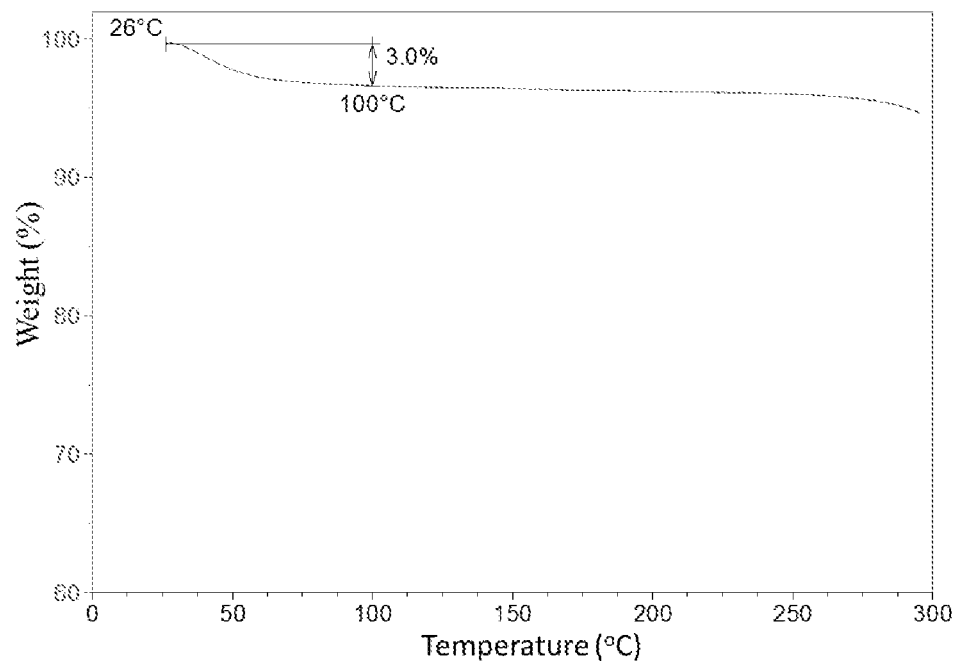
FIG. 8C shows a TGA curve of Form CS11 according to example 8 method 1 of the present disclosure

Sample 8-b was selected for characterization. The XRPD pattern is substantially as depicted in FIG. 8A, and the XRPD data are listed in Table 8.2. The DSC curve is substantially as depicted in FIG. 8B, which shows the first endothermic peak at around 49° C., the second endothermic peak at around 206° C., the first exothermic peak at 208° C. and the third endothermic peak at 230° C. The TGA curve is substantially as depicted in FIG. 8C, which shows about 3.0% weight loss when heated to 100° C.

TABLE 8.2

| 2 Theta | d spacing | Intensity % |
|---|---|---|
| 4.36 | 20.25 | 22.75 |
| 7.61 | 11.61 | 35.17 |
| 7.80 | 11.33 | 71.58 |
| 8.79 | 10.06 | 75.43 |
| 9.70 | 9.12 | 100.00 |
| 10.11 | 8.75 | 11.17 |

TABLE 8.2-continued

| 2 Theta | d spacing | Intensity % |
|---|---|---|
| 13.02 | 6.80 | 8.06 |
| 13.55 | 6.54 | 23.03 |
| 15.32 | 5.79 | 8.84 |
| 15.70 | 5.64 | 7.37 |
| 16.87 | 5.26 | 11.53 |
| 17.64 | 5.03 | 10.29 |
| 18.67 | 4.75 | 1.01 |
| 19.55 | 4.54 | 3.26 |
| 20.40 | 4.35 | 5.32 |
| 20.99 | 4.23 | 5.64 |
| 21.58 | 4.12 | 21.02 |
| 22.72 | 3.91 | 9.87 |
| 23.67 | 3.76 | 3.85 |
| 25.65 | 3.47 | 5.77 |
| 26.85 | 3.32 | 2.83 |
| 27.34 | 3.26 | 5.29 |
| 30.28 | 2.95 | 1.82 |
| 32.57 | 2.75 | 1.07 |
| 34.69 | 2.59 | 2.33 |
| 35.80 | 2.51 | 2.02 |
| 36.56 | 2.46 | 1.51 |

Figure 8D:
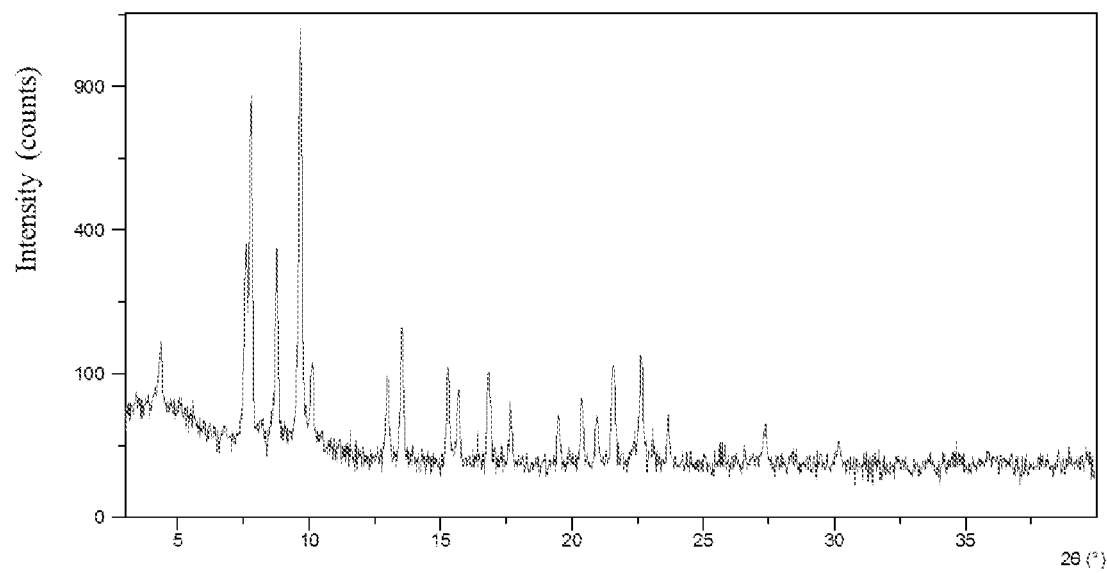
FIG. 8D shows an XRPD pattern of Form CS11 according to example 8 method 2 of the present disclosure

Preparation of Form CS11 (Method 2)
The process of preparing Form CS11 comprises the following steps:
Dissolving step: about 10 mg of apabetalone solid was dissolved in corresponding solvent of Table 8.3, and then filtered to get clear solutions.
Precipitation step: The prepared solution was left at room temperature for slow evaporation until solid precipitated. The obtained solid was Form CS11 of Apabetalone.
Said reaction conditions, solvent composition and solvent amount of the preparation method of apabetalone Form CS11 are shown in Table 8.3. The samples 8-c to 8-f were confirmed to be Form CS11 by XRPD. The XRPD pattern of sample 8-d is substantially as depicted in FIG. 8D, and the XRPD data are listed in Table 8.4.

TABLE 8.3

| Sample No | Weight (mg) | Solvent (v/v) | Volume (mL) | T (° C.) |
|---|---|---|---|---|
| 8-c | 10.4 | Chloroform | 2.0 | 25 |
| 8-d | 10.3 | Methanol/acetone (1:1) | 1.7 | 25 |
| 8-e | 10.1 | Methanol/methyl isobutyl ketone (2:1) | 1.7 | 25 |
| 8-f | 10.2 | Methanol/toluene (4:1) | 1.3 | 25 |

TABLE 8.4

| 2 Theta | d spacing | Intensity % |
|---|---|---|
| 4.36 | 20.26 | 9.4 |
| 7.60 | 11.64 | 29.25 |
| 7.79 | 11.34 | 74.56 |
| 8.78 | 10.07 | 28.33 |
| 9.68 | 9.14 | 100 |
| 10.13 | 8.73 | 8.22 |
| 13.00 | 6.81 | 6.84 |
| 13.54 | 6.54 | 13.96 |
| 15.29 | 5.80 | 8.47 |
| 15.68 | 5.65 | 5.67 |
| 16.83 | 5.27 | 7.76 |
| 17.65 | 5.02 | 4.52 |
| 19.48 | 4.56 | 3.39 |
| 20.37 | 4.36 | 4.97 |
| 20.97 | 4.24 | 3.31 |
| 21.60 | 4.11 | 8.44 |
| 22.65 | 3.93 | 9.42 |

TABLE 8.4-continued

| 2 Theta | d spacing | Intensity % |
|---|---|---|
| 23.08 | 3.85 | 2.33 |
| 23.67 | 3.76 | 3.29 |
| 25.65 | 3.47 | 0.78 |
| 27.34 | 3.26 | 2.23 |
| 30.18 | 2.96 | 1.12 |
| 32.46 | 2.76 | 0.27 |
| 34.67 | 2.59 | 0.62 |
| 36.15 | 2.48 | 0.32 |

Stability Study of Form CS11

Figure 8E:
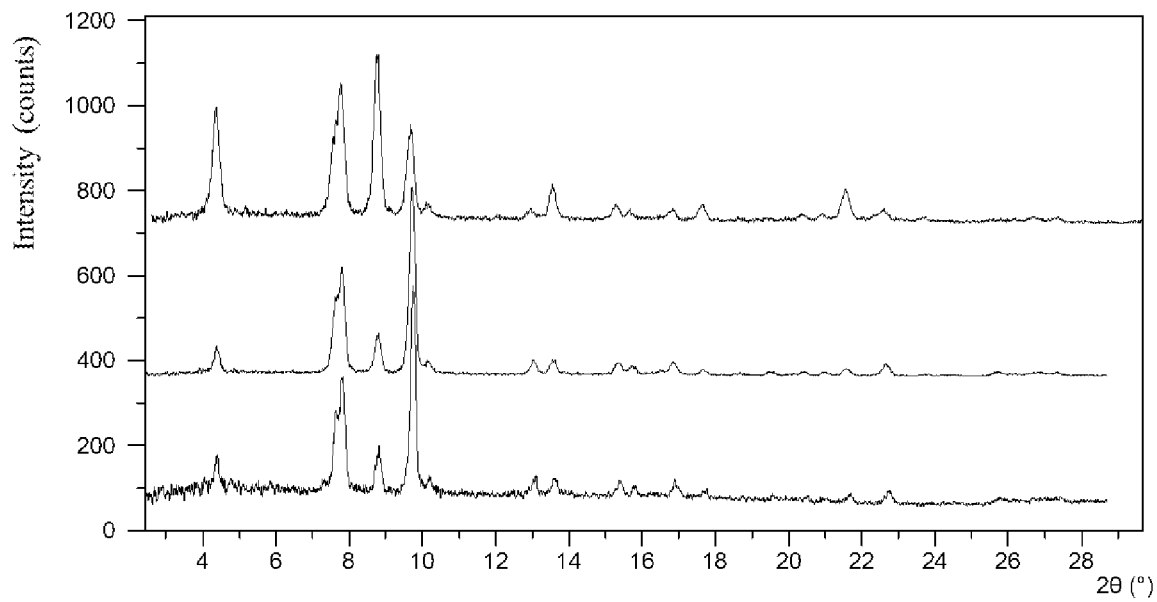
FIG. 8E shows an XRPD pattern overlay of Form CS11 before and after being stored under 25° C./60% RH and 40° C./75% RH for 6 weeks (from top to bottom: XRPD pattern before storage, XRPD pattern after being stored under 25° C./60% RH for 6 weeks, XRPD pattern after being stored under 40° C./75% RH for 6 weeks).

Two samples of apabetalone Form CS11 were placed in constant temperature and humidity chambers at 25° C./60% RH and 40° C./75% RH for 6 weeks in open dishes. Crystalline form of the sample were tested by XRPD and impurity of the sample were tested to check the stability of Form CS11. The XRPD pattern overlay was substantially as depicted in FIG. 8E (from top to bottom: XRPD pattern of Form CS11 before and after being stored under 25° C./60% RH and 40° C./75% RH for 6 weeks).

No form change and obvious purity decrease was observed for Form CS11 after being stored at 25° C./60% RH and 40° C./75% RH for 6 weeks. It can be seen that Form CS11 has good stability.

Solubility Study of Form CS11

The prepared solid of apabetalone Form CS11 was suspended into SGF (simulated gastric fluids) and FeSSIF (fed state simulated intestinal fluids, pH=5.0) to obtain saturated solutions. After being equilibrated for 1 h, 4 h and 24 h, concentrations of the saturated solutions were measured by HPLC. The results are listed in Table 8.5.

TABLE 8.5

| Time (h) | Solubility (mg/mL) | |
|---|---|---|
| | SGF | FeSSIF |
| 1 | 0.71 | 0.29 |
| 4 | 0.65 | 0.26 |
| 24 | 0.65 | 0.30 |

The above results show that Form CS11 of apabetalone has good solubility in SGF and FeSSIF. Polymorph with high solubility is beneficial to increase the blood concentration of drugs in human body and improve the bioavailability of drugs, which is of great significance for drug research.

Example 9

Preparation of Form CS4

Form CS4 was obtained by heating Form CS11 of apabetalone to 220° C.

Figure 9A:
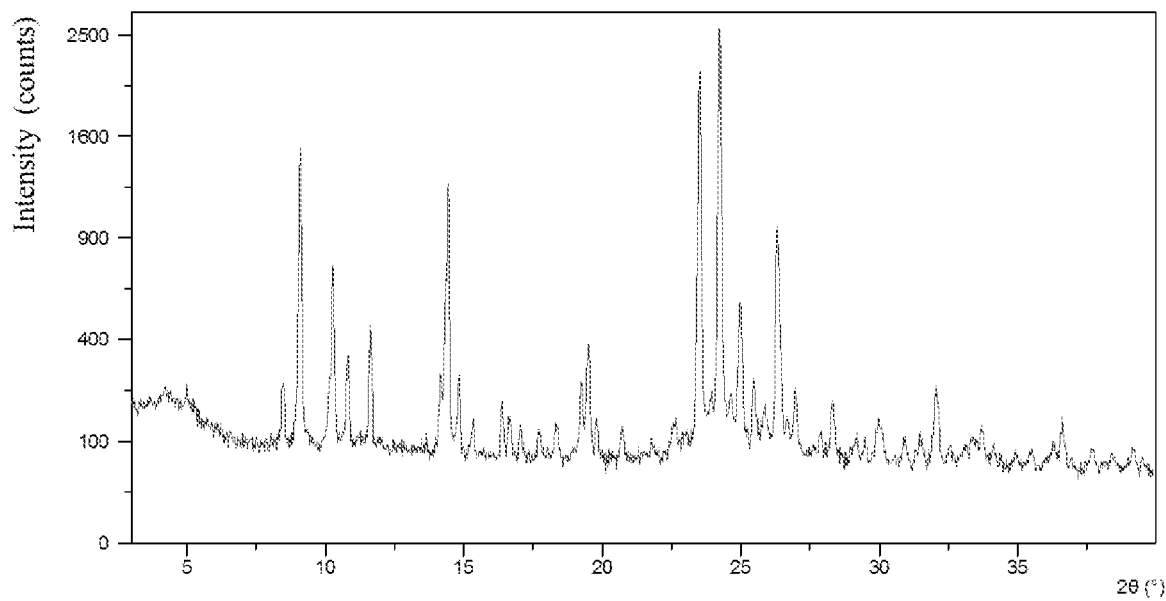
FIG. 9A shows an XRPD pattern of Form CS4 according to example 9 of the present disclosure
Figure 9B:
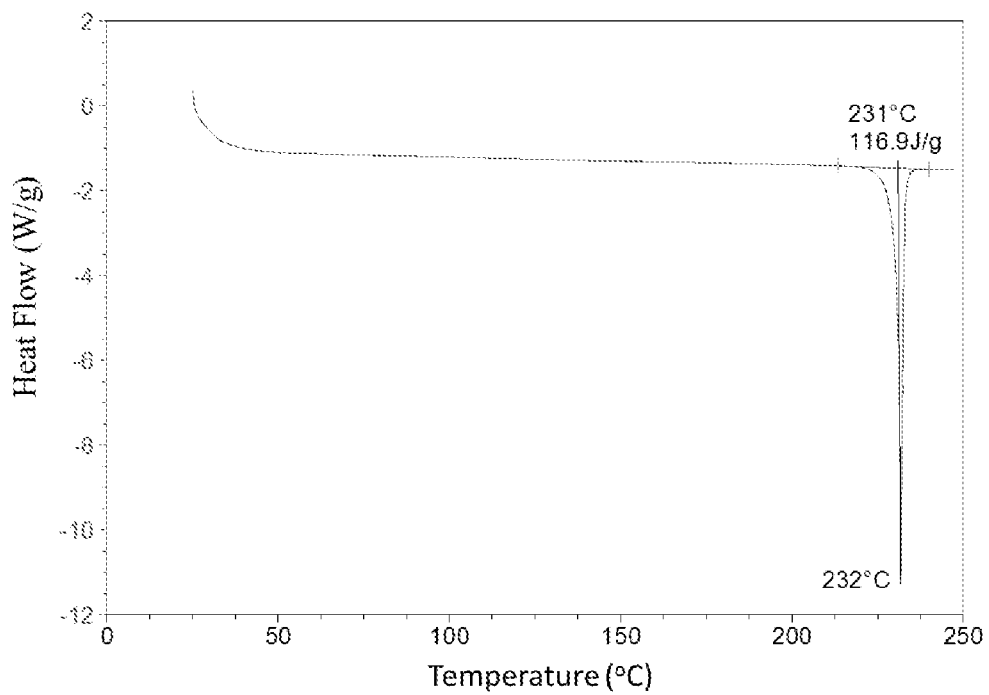
FIG. 9B shows a DSC curve of Form CS4 according to example 9 of the present disclosure
Figure 9C:
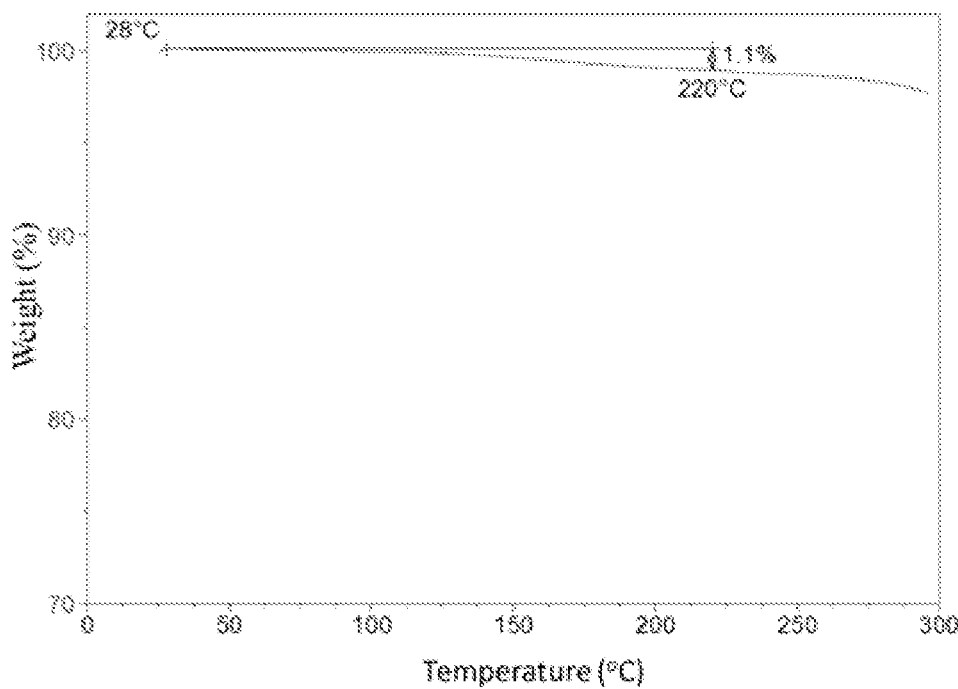
FIG. 9C shows a TGA curve of Form CS4 according to example 9 of the present disclosure

The XRPD pattern of Form CS4 is substantially as depicted in FIG. 9A, and the XRPD data are listed in Table 9.1. The DSC curve is substantially as depicted in FIG. 9B, which shows the first endothermic peak at around 231° C. The TGA curve is substantially as depicted in FIG. 9C, which shows about 1.1% weight loss when heated to 220° C.

TABLE 9.1

| 2 Theta | d spacing | Intensity % |
|---|---|---|
| 8.48 | 10.43 | 6.12 |
| 9.11 | 9.71 | 53.67 |
| 10.29 | 8.60 | 26.02 |
| 10.81 | 8.18 | 10.09 |
| 11.64 | 7.60 | 14.92 |
| 14.17 | 6.25 | 7.64 |
| 14.45 | 6.13 | 45.98 |
| 14.84 | 5.97 | 7.80 |
| 15.34 | 5.78 | 2.53 |
| 16.38 | 5.41 | 4.37 |
| 17.06 | 5.20 | 2.02 |
| 17.72 | 5.00 | 1.91 |
| 18.32 | 4.84 | 2.30 |
| 19.25 | 4.61 | 6.41 |
| 19.53 | 4.55 | 12.06 |
| 19.80 | 4.48 | 2.96 |
| 20.73 | 4.29 | 2.28 |
| 22.60 | 3.93 | 2.69 |
| 23.51 | 3.78 | 83.35 |
| 24.23 | 3.67 | 100.00 |
| 24.99 | 3.56 | 19.67 |
| 25.47 | 3.50 | 7.99 |
| 25.89 | 3.44 | 4.39 |
| 26.32 | 3.39 | 35.61 |
| 26.97 | 3.31 | 6.81 |
| 28.30 | 3.15 | 5.10 |
| 29.95 | 2.98 | 2.52 |
| 32.05 | 2.79 | 5.67 |
| 33.73 | 2.66 | 2.67 |
| 36.61 | 2.45 | 3.15 |
| 37.68 | 2.39 | 1.06 |

Long-Term Stability Study of Form CS4

Figure 9D:
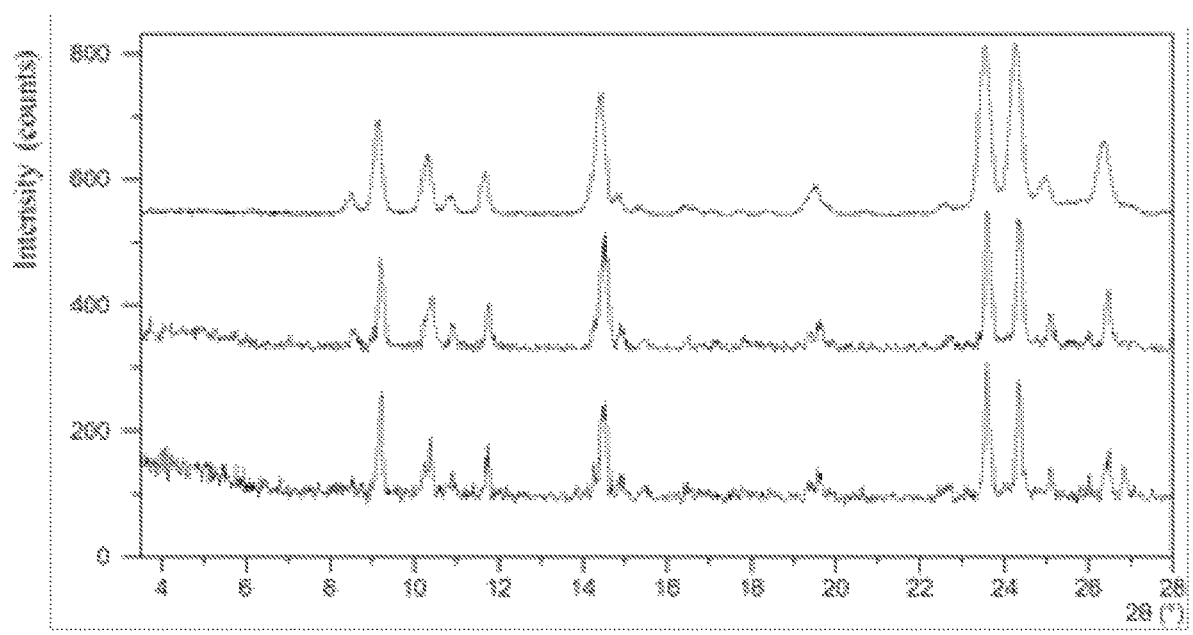
FIG. 9D shows an XRPD pattern overlay of Form CS4 before and after being stored under 25° C./60% RH and 40° C./75% RH for 10 months (from top to bottom: XRPD pattern before storage, XRPD pattern after being stored under 25° C./60% RH for 10 months, XRPD pattern after being stored under 40° C./75% RH for 10 months).

Two samples of apabetalone Form CS4 were placed in open dishes in constant temperature and humidity chambers at 25° C./60% RH and 40° C./75% RH for 10 months. Crystalline form of the sample were tested by XRPD and impurity of the sample were tested to check the stability of Form CS4. The stability results are substantially as depicted in FIG. 9D (from top to bottom: XRPD pattern of Form CS4 before and after being stored under 25° C./60% RH and 40° C./75% RH for 10 months) and Table 9.2.

No form change and obvious purity decrease was observed for Form CS4 after being stored at 25° C./60% RH and 40° C./75% RH for 10 months. It can be seen that Form CS4 has good stability.

TABLE 9.2

| Condition | 1 week | 2 weeks | 4 weeks | 10 months |
|---|---|---|---|---|
| 25° C./60% RH | 99.10 | 99.06 | 99.05 | 99.04 |
| 40° C./75% RH | 99.10 | 98.99 | 99.04 | 99.02 |

Solubility Study of Form CS4

The prepared solid of apabetalone Form CS4 was suspended into SGF (simulated gastric fluids) and FeSSIF (fed state simulated intestinal fluids, pH=5.0) to obtain saturated solutions. After being equilibrated for 1 h, 4 h and 24 h, concentrations of the saturated solutions were measured by HPLC. The results are listed in Table 9.3, which indicated that Form CS4 has good solubility.

TABLE 9.3

| Time (h) | Solubility (mg/mL) | |
| --- | --- | --- |
| | SGF | FeSSIF |
| 1 | 0.30 | 0.14 |
| 4 | 0.28 | 0.10 |
| 24 | 0.38 | 0.16 |

Hygroscopicity Study of Form CS4

Figure 9E:
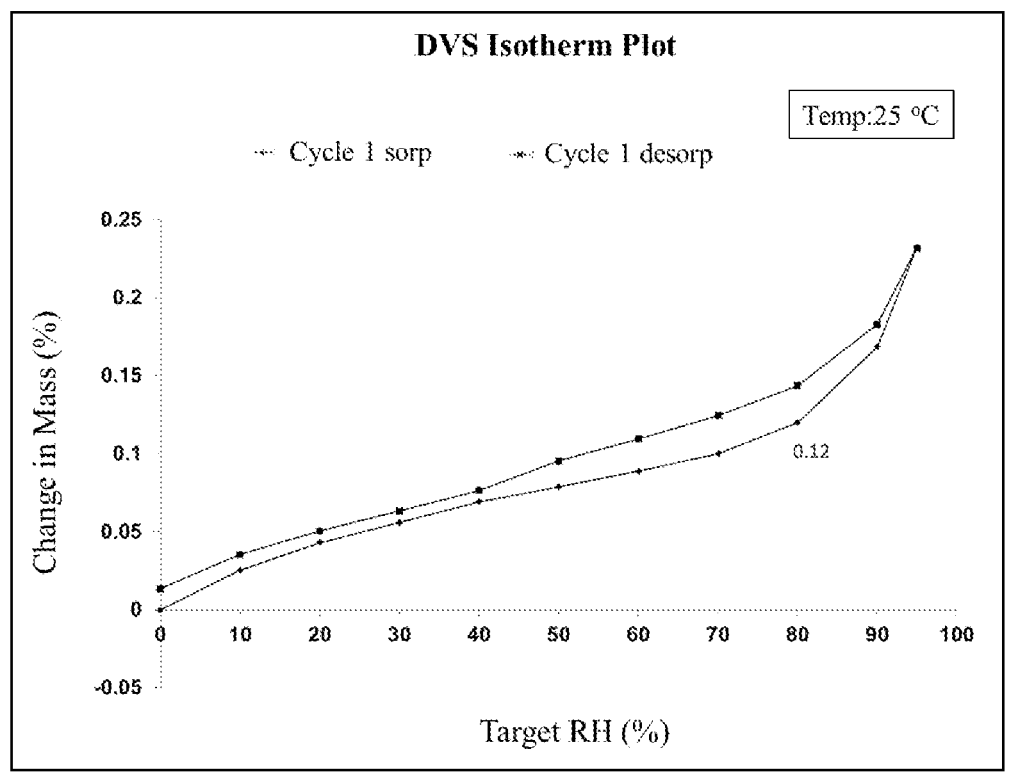
FIG. 9E shows a DVS plot of Form CS4 according to example 9 of the present disclosure

Dynamic vapor sorption (DVS) was applied to test hygroscopicity of Form CS4 of the present disclosure with about 10 mg of sample. The result was listed in Table 9.4. The DVS plot of Form CS4 is as depicted in FIG. 9E.

TABLE 9.4

| Form | Weight gain under 80% relative humidity |
| --- | --- |
| Form CS4 | 0.12% |

Figure 9F:
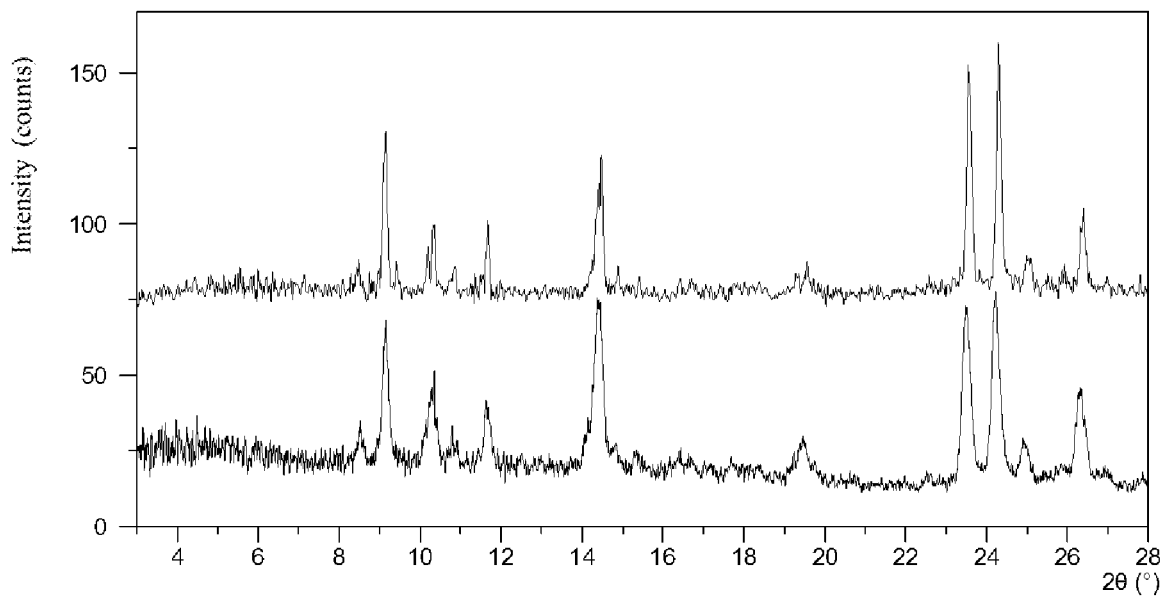
FIG. 9F shows an XRPD pattern overlay of Form CS4 according to example 9 of the present disclosure before and after DVS test.

The results showed that weight gain of Form CS4 under 80% RH is 0.12%. According to the hygroscopicity criteria, Form CS4 is almost non hygroscopic. The XRPD pattern of Form CS4 after DVS test is shown in FIG. 9F. No form change was observed for Form CS4 before and after DVS test, which indicates that Form CS4 is stable under the influence of humidity.

Form CS4 of the present disclosure shows low hygroscopicity, which can well avoid the problems such as crystal instability in the process of drug preparation and/or storage, as well as the unprocessability of the preparation caused by external factors such as environmental moisture, which is conducive to the accurate quantitative preparation and later transportation and storage.

Mechanical Stability of Form CS4

Figure 9G:
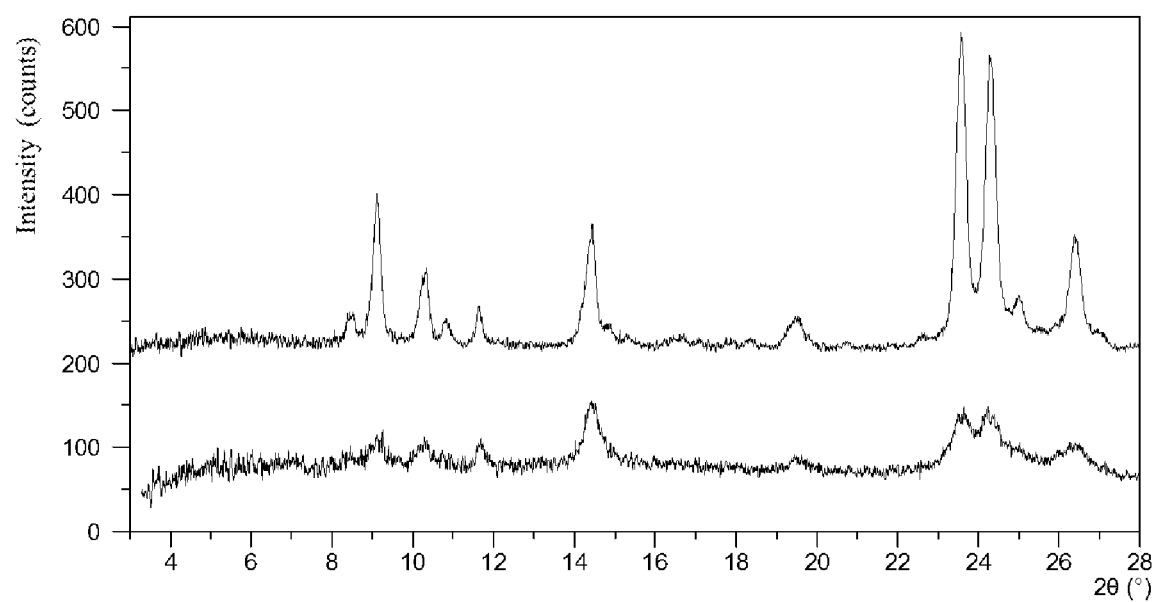
FIG. 9G shows an XRPD pattern overlay of Form CS4 according to example 9 of the present disclosure before and after grinding.

Certain amount of Form CS4 was placed in a mortar and ground manually for 5 minutes. Crystalline form of the sample was checked by XRPD. The results are shown in FIG. 9G.

The results showed that no form change and obvious crystalline decrease was observed for Form CS4 of apabetalone under certain mechanical stress. From CS4 can maintain stable physical and chemical properties under certain mechanical stress, which is suitable for drug preparation and storage. Grinding of API is usually needed in the process of formulation, and good mechanical stability will reduce the risk of crystallinity decreasing and transformation of solid form of API.

The examples described above are only for illustrating the technical concepts and features of the present disclosure, and intended to make those skilled in the art being able to understand the present disclosure and thereby implement it, and should not be concluded to limit the protective scope of the present disclosure. Any equivalent variations or modifications according to the spirit of the present disclosure should be covered by the protective scope of the present disclosure.

The invention claimed is:

1. A crystalline form CS1 of apabetalone, wherein the X-ray powder diffraction pattern shows characteristic peaks at 2theta values of 6.1°±0.2°, 12.3°±0.2°, 26.1°±0.2° and 26.8°±0.2° using CuKα radiation.

2. The crystalline form CS1 according to claim 1, wherein the X-ray powder diffraction pattern shows one or more characteristic peaks at 2theta values of 16.4°±0.2°, 18.5°±0.2°, 23.2°±0.2°, 13.0°±0.2°, 14.1°±0.2°, 17.1°±0.2° and 24.5°±0.2° using CuKα radiation.

3. A crystalline form CS2 of apabetalone, wherein the X-ray powder diffraction pattern shows characteristic peaks at 2theta values of 11.5°±0.2°, 6.6°±0.2° and 8.8°±0.2° using CuKα radiation.

4. The crystalline form CS2 according to claim 3, wherein the X-ray powder diffraction pattern shows one or two characteristic peaks at 2theta values of 5.1°±0.2° and 15.3°±0.2° using CuKα radiation.

5. A crystalline form CS8 of apabetalone, wherein the X-ray powder diffraction pattern shows characteristic peaks at 2theta values of 23.9°±0.2°, 13.5°±0.2°, 7.8°±0.2°, 22.5°±0.2° and 11.4°±0.2° using CuKα radiation.

6. The crystalline form CS8 according to claim 5, wherein the X-ray powder diffraction pattern shows one or more characteristic peaks at 2theta values of 25.9°±0.2°, 13.1°±0.2°, 28.1°±0.2° and 20.2°±0.2° using CuKα radiation.

7. A crystalline form CS13 of apabetalone, wherein the X-ray powder diffraction pattern shows characteristic peaks at 2theta values of 5.1°±0.2°, 12.5°±0.2° and 17.1°±0.2° using CuKα radiation.

8. The crystalline form CS13 according to claim 7, wherein the X-ray powder diffraction pattern shows one or more characteristic peaks at 2theta values of 6.4°±0.2°, 8.5°±0.2, 25.7°±0.2°, 7.8°±0.2° and 16.0°±0.2° using CuKα radiation.

9. A crystalline form CS20 of apabetalone, wherein the X-ray powder diffraction pattern shows characteristic peaks at 2theta values of 8.4°±0.2°, 18.9°±0.2° and 13.5°±0.2° using CuKα radiation.

10. The crystalline form CS20 according to claim 9, wherein the X-ray powder diffraction pattern shows one or more characteristic peaks at 2theta values of 11.3°±0.2°, 9.4°±0.2, 5.6°±0.2°, 26.3°±0.2°, 20.1°±0.2°, 20.6°±0.2° and 24.4°±0.2° using CuKα radiation.

11. A crystalline form CS7 of apabetalone, wherein the X-ray powder diffraction pattern shows characteristic peaks at 2theta values of 5.9°±0.2°, 6.7°±0.2°, 10.7°±0.2° and 12.5°±0.2° using CuKα radiation.

12. The crystalline form CS7 according to claim 11, wherein the X-ray powder diffraction pattern shows one or two or three characteristic peaks at 2theta values of 8.4°±0.2°, 16.9°±0.2, 13.3°±0.2°, 16.0°±0.2°, 25.1°±0.2°, 15.0°±0.2° and 21.8°±0.2° using CuKα radiation.

13. A crystalline form CS9 of apabetalone, wherein the X-ray powder diffraction pattern shows characteristic peaks at 2theta values of 7.3°±0.2°, 9.9°±0.2° and 17.0°±0.2° using CuKα radiation.

14. The crystalline form CS9 according to claim 13, wherein the X-ray powder diffraction pattern shows one or more characteristic peaks at 2theta values of 13.4°±0.2°, 3.9°±0.2, 12.8°±0.2°, 12.1°±0.2°, 24.9°±0.2°, 22.5°±0.2° and 24.2°±0.2° using CuKα radiation.

15. A crystalline form CS11 of apabetalone, wherein the X-ray powder diffraction pattern shows characteristic peaks at 2theta values of 7.8°±0.2°, 8.8°±0.2°, 9.7°±0.2° and 13.6°±0.2° using CuKα radiation.

16. The crystalline form CS11 according to claim 15, wherein the X-ray powder diffraction pattern shows one or more characteristic peaks at 2theta values of 4.4°±0.2°, 16.9°±0.2, 21.6°±0.2°, 13.0°±0.2° and 15.3°±0.2° using CuKα radiation.

17. A crystalline form CS4 of apabetalone, wherein the X-ray powder diffraction pattern shows characteristic peaks at 2theta values of 9.1°±0.2°, 14.5°±0.2°, 23.5°±0.2° and 24.2°±0.2° using CuKα radiation.

18. The crystalline form CS4 according to claim 17, wherein the X-ray powder diffraction pattern shows one or two or three characteristic peaks at 2theta values of 10.3°±0.2°, 25.0°±0.2, 26.3°±0.2°, 10.8°±0.2°, 11.6°±0.2° and 19.5°±0.2° using CuKα radiation.

19. A method for treating cardiovascular, cholesterol or lipid-related disorders, comprising administering to a patient in need thereof a therapeutically effective amount of the Form CS1 according to claim 1.

20. A method for treating cardiovascular, cholesterol or lipid-related disorders, comprising administering to a patient in need thereof a therapeutically effective amount of the Form CS7 according to claim 11.

21. A method for treating cardiovascular, cholesterol or lipid-related disorders, comprising administering to a patient in need thereof a therapeutically effective amount of the Form CS4 according to claim 17.

22. A method for treating cardiovascular, cholesterol or lipid-related disorders, comprising administering to a patient in need thereof a therapeutically effective amount of the Form CS9 according to claim 13.

\* \* \* \* \*